United States Patent
Soubrane et al.

(10) Patent No.: US 11,827,671 B2
(45) Date of Patent: Nov. 28, 2023

(54) METHODS FOR TREATING SYSTEMIC SCLEROSIS

(71) Applicant: Sanofi, Paris (FR)

(72) Inventors: Christina Soubrane, Levallois-Perret (FR); Corinne Esperet, Palaiseau (FR); Frederic Marrache, Paris (FR); Peter Wung, Sugar Land, TX (US)

(73) Assignee: SANOFI, Paris (FR)

( * ) Notice: Subject to any disclaimer, the term of this patent is extended or adjusted under 35 U.S.C. 154(b) by 597 days.

(21) Appl. No.: 16/881,863

(22) Filed: May 22, 2020

(65) Prior Publication Data

US 2020/0392224 A1    Dec. 17, 2020

Related U.S. Application Data

(60) Provisional application No. 62/979,875, filed on Feb. 21, 2020, provisional application No. 62/852,941, filed on May 24, 2019.

(30) Foreign Application Priority Data

Oct. 8, 2019   (EP) ..................... 19306309

(51) Int. Cl.
   *C07K 16/24*   (2006.01)
   *A61P 25/28*   (2006.01)
   *A61K 39/00*   (2006.01)
   *A61K 9/00*    (2006.01)
   *A61K 9/19*    (2006.01)
   *A61K 45/06*   (2006.01)

(52) U.S. Cl.
   CPC ............ *C07K 16/247* (2013.01); *A61P 25/28* (2018.01); *A61K 9/0019* (2013.01); *A61K 9/19* (2013.01); *A61K 45/06* (2013.01); *A61K 2039/505* (2013.01); *A61K 2039/545* (2013.01); *C07K 2317/31* (2013.01); *C07K 2317/565* (2013.01)

(58) Field of Classification Search
   CPC .................. C07K 16/247; C07K 16/244; C07K 2317/31; C07K 2317/565; C07K 2317/33; C07K 2317/76; A61P 17/00; A61P 37/00; A61P 25/28; A61P 11/00; A61K 9/0019; A61K 9/19; A61K 2039/54; A61K 2039/505; A61K 2039/545
   See application file for complete search history.

(56) References Cited

U.S. PATENT DOCUMENTS

| | | |
|---|---|---|
| 4,816,567 A | 3/1989 | Cabilly |
| 5,314,995 A | 5/1994 | Fell, Jr. |
| 5,807,715 A | 9/1998 | Morrison |
| 5,869,619 A | 2/1999 | Studnicka |
| 5,989,830 A | 11/1999 | Davis |
| 6,277,375 B1 | 8/2001 | Ward |
| 7,612,181 B2 | 11/2009 | Wu |
| 7,833,521 B2 | 11/2010 | Fleer et al. |
| 8,388,965 B2 | 3/2013 | Rao |
| 9,738,728 B2 | 8/2017 | Rao |
| 10,005,835 B2 | 6/2018 | Carayon |
| 11,008,389 B2 | 5/2021 | Bender et al. |
| 11,136,388 B2 | 10/2021 | Esperet et al. |
| 11,453,727 B2 | 9/2022 | Rao et al. |
| 2010/0226923 A1 | 9/2010 | Rao |
| 2013/0209469 A1 | 8/2013 | Rao |
| 2013/0236460 A1 | 9/2013 | Rao |
| 2013/0236461 A1 | 9/2013 | Rao |
| 2013/0236462 A1 | 9/2013 | Rao |
| 2013/0236463 A1 | 9/2013 | Rao |
| 2013/0251716 A1 | 9/2013 | Rao |
| 2013/0251717 A1 | 9/2013 | Rao |
| 2013/0251718 A1 | 9/2013 | Rao |
| 2013/0259866 A1 | 10/2013 | Rao |
| 2013/0344074 A1 | 12/2013 | Bender |
| 2016/0075777 A1* | 3/2016 | Carayon ............. C07K 16/468 530/387.3 |
| 2017/0029498 A1 | 2/2017 | Bender |
| 2017/0145089 A1 | 5/2017 | Esperet |
| 2019/0359703 A1 | 11/2019 | Esperet |
| 2020/0392224 A1 | 12/2020 | Soubrane et al. |
| 2021/0047437 A1 | 2/2021 | Rao et al. |
| 2021/0221882 A1 | 7/2021 | Bender et al. |

FOREIGN PATENT DOCUMENTS

| | | |
|---|---|---|
| EP | 0239400 A2 | 9/1987 |
| EP | 0239400 A3 | 4/1989 |
| EP | 0338745 A1 | 10/1989 |
| EP | 0413622 A1 | 2/1991 |
| EP | 0396387 A3 | 4/1991 |
| EP | 0332424 A3 | 7/1991 |
| WO | 198909622 A1 | 10/1989 |
| WO | 198912624 A3 | 4/1990 |

(Continued)

OTHER PUBLICATIONS

Wynn, T.A. Fibrotic disease and the T(H)1/T(H)2 paradigm. Nat Rev Immunol. Aug. 2004;4(8):583-94. doi: 10.1038/nri1412.*

(Continued)

*Primary Examiner* — Kimberly Ballard
*Assistant Examiner* — Stacey N MacFarlane
(74) *Attorney, Agent, or Firm* — MORRISON & FOERSTER LLP

(57) ABSTRACT

The invention provides methods for treating Systemic Sclerosis by administering a dual-V region bispecific antibody that specifically binds IL-4 and IL-13.

19 Claims, 8 Drawing Sheets

Specification includes a Sequence Listing.

(56) References Cited

FOREIGN PATENT DOCUMENTS

| WO | 199114438 A1 | 10/1991 |
|---|---|---|
| WO | 199208495 A1 | 5/1992 |
| WO | 199315199 A1 | 8/1993 |
| WO | 199315200 A1 | 8/1993 |
| WO | 199321319 A1 | 10/1993 |
| WO | 199733899 A1 | 9/1997 |
| WO | 199734631 A1 | 9/1997 |
| WO | 199734911 A1 | 9/1997 |
| WO | 199823289 A1 | 6/1998 |
| WO | 199923105 A1 | 5/1999 |
| WO | 200177137 A1 | 10/2001 |
| WO | 2003038041 A3 | 9/2003 |
| WO | 2006042333 A3 | 8/2006 |
| WO | 2003035847 A3 | 7/2007 |
| WO | 2009052081 A4 | 7/2009 |
| WO | 2012125775 A1 | 9/2012 |
| WO | 2014177568 A1 | 11/2014 |
| WO | 2015121318 A1 | 8/2015 |
| WO | 2015198146 A3 | 3/2016 |
| WO | 2020242989 A1 | 12/2020 |

OTHER PUBLICATIONS

Nikpour et al. Epidemiology of systemic sclerosis. Best Pract Res Clin Rheumatol. Dec. 2010;24(6):857-69. doi: 10.1016/j.berh.2010.10.007.*

Allanore, Y. et al. (Nov. 11, 2019). "Efficacy and Safety of Romilkimab in Diffuse Cutaneous Systemic Sclerosis (dcSSc): A Randomized, Double-Blind, Placebo-Controlled, 24-week, Proof of Concept Study," Arthritis Rheumatol 71(11): 2 pages.

Carter, P. (2001). "Bispecific Human IgG by Design," Immunol. Methods 248:7-15.

Carter, P. et al. (May 1992). "Humanization of an Anti-p185HER2 Antibody for Human Cancer Therapy," Proc. Natl. Acad. Sci. USA 89:4285-4289.

Carter, P. et al. (Oct. 1995). Toward The Production Of Bispecific Antibody Fragments For Clinical Applications. J. Hematotherapy 4:463-470.

Chothia, C. et al. (Aug. 20, 1987). "Canonical Structures for the Hypervariable Regions of Immunoglobulins," J. Mol. Biol. 196(4):901-917.

Elhai M., et al. (Jun. 2012). "Trends In Mortality In Patients With Systemic Sclerosis Over 40 Years: A Systematic Review And Meta-Analysis Of Cohort Studies," Rheumatology (Oxford) 51(6):1017-1026.

Gasparini, G. et al. (Aug. 7, 2019). "Interleukin-4brAnd Interleukin-13 As Possible TherapeuticbrTargets In Systemic Sclerosis," Cytokine, Academic Press Ltd, Philadelphia, PA, vol. 125, 5 pages.

Gillies, S.D. et al. (Dec. 20, 1989). "High-Level Expression Of Chimeric Antibodies Using Adapted cDNA Variable Region Cassettes," J. Immunol. Methods 125(1-2):191-202.

Heinzmann, A. el al. (Mar. 1, 2000). "Genetic Variants Of IL-13 Signalling And Human Asthma And Atopy," Hum Mol Genet. 9(4):549-559.

Khanna, D. et al. (Feb. 2016). "The American College Of Rheumatology Provisional Composite Response Index For Clinical Trials In Early Diffuse Cutaneous Systemic Sclerosis." Arthritis Care & Research 68(2):167-178.

Lazar, G.A. et al. (Mar. 2007, e-pub Oct. 31, 2006). "A Molecular Immunology Approach To Antibody Humanization And Functional Optimization." Molecular Immunology 44(8):1986-1998.

Leroy, E. et al. (Feb. 1988). "Scleroderma (Systemic Sclerosis): Classification, Subsets And Pathogenesis," The Journal of Rheumatology 15(2):202-205.

Liddiard, K. et al. (Nov. 29, 2006). "Interleukin-4 Induction Of The CC Chemokine TARC (CCL 17) In Murine Macrophages Is Mediated By Multiple STAT6 Sites In The TARC Gene Promoter," BMC Molecular Biology 7(45):1-18.

MacIntyre, N. et al. (2005). "Standardisation Of The Single-Breath Determination Of Carbon Monoxide Uptake In The Lung," European Respiratory Journal 26(4):720-735.

Manno, R. et al. (Nov. 1, 2010). "Immunotherapy of Systemic Sclerosis," Immunotherapy 2(6):863-878, 24 pages.

Miller, M.R. et al. (Aug. 2005). "Standardisation Of Spirometry," European Respiratory Journal 26(2):319-338.

Milstein, C. et al. (Oct. 6, 1983). "Hybrid Hybridomas and Their Use In Immunohistochemistry," Nature 305:537-540.

Monick, M.M. et al. (2007). "Respiratory syncytial virus synergizes with Th2 cytokines to induce optimal levels of TARC/CCL17." The Journal of Immunology 179(3):1648-1658.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Sep. 1985). "Transfectomas Provide Novel Chimeric Antibodies," Science 229(4719):1202-1207.

Ngoc, L. P. et al. "Cytokines, Allergy, and Asthma," Curr. Opin. Allergy Clin. Immunol. (2005) 5:161-166.

Nihtyanova, S.I. et al. (Feb. 2010, e-pub. Dec. 4, 2009). "Improved Survival In Systemic Sclerosis Is Associated With Better Ascertainment Of Internal Organ Disease: A Retrospective Cohort Study," QJM: An International Journal of Medicine 103(2):109-115.

Nikpour, M. (Mar. 2014). "Mortality In Systemic Sclerosis: Lessons Learned From Population-Based And Observational Cohort Studies," Current Opinion In Rheumatology 26(2):131-137.

Oi, V.T. et al. (1986). "Chimeric Antibodies," Bio Techniques 4(3):214-219.

Plückthun, A. et al. (Jun. 1997). "New Protein Engineering Approaches to Multivalent and Bispecific Antibody Fragments," Immunotechnology 3:83-105.

Presta, L.G. et al. (Sep. 1, 1993). "Humanization of an Antibody Directed Against IgE," J. Immunol. 151(5):2623-2632.

Raghu, G., et al. (Dec. 2018). "SAR156597 In Idiopathic Pulmonary Fibrosis: A Phase 2 Placebo-Controlled Study (DRI11772)," European Respiratory Journal 52(6):1-12.

Sims, M.J. et al. (Aug. 15, 1993). "A Humanized CD18 Antibody Can Block Function Without Cell Destruction," J. Immunol. 151(4):2296-2308.

Staerz, U.D. et al. (Apr. 1985). "Hybrid Antibodies Can Target Sites For Attack By T Cells," Nature 314(6012):628-631.

Steen, V.D. et al. (Nov. 1997). "The Value Of The Health Assessment Questionnaire And Special Patient-Generated Scales To Demonstrate Change In Systemic Sclerosis Patients Over Time," Arthritis & Rheumatism: Official Journal of the American College of Rheumatology 40(11):984-1991.

Studnicka, G.M. et al. (Jun. 1994). "Human-Engineered Monoclonal Antibodies Retain Full Specific Binding Activity By Preserving Non-CDR Complementarity-Modulating Residues," Protein Engineering 7(6):805-814. Abstract Submitted.

Takahashi, T. et al. (Oct. 1994). "Human Fas Ligand: Gene Structure, Chromosomal Location And Species Specificity," Int Immunol 6(10):1567-1574.

Todorovska, A. et al. (2001). "Design and Application of Diabodies, Triabodies and Tetrabodies for Cancer Targeting," J. of Immunological Methods 248 :47-66.

U.S. Appl. No. 15/985,414, filed May 21, 2018 by Carayon et al. brbr(pursuant to the waiver of 37 C.F.R. § 1.98 (a)(2)(iii) issued by the Office on Sep. 21, 2004.).

U.S. Appl. No. 16/250,868, filed Jan. 17, 2019 by Carayon et al. brbr(pursuant to the waiver of 37 C.F.R. § 1.98 (a)(2)(iii) issued by the Office on Sep. 21, 2004.).

U.S. Appl. No. 16/560,182, filed Sep. 4, 2019 by Carayon et al. brbr(pursuant to the waiver of 37 C.F.R. § 1.98 (a)(2)(iii) issued by the Office on Sep. 21, 2004.).

U.S. Appl. No. 17/524,427, filed Nov. 11, 2021 by Bender et al. brbr(pursuant to the waiver of 37 C.F.R. § 1.98 (a)(2)(iii) issued by the Office on Sep. 21, 2004.).

Van Den Hoogen, F. et al. (2013). "2013 Classification Criteria For Systemic Sclerosis: An American College Of Rheumatology/European League Against Rheumatism Collaborative Initiative," Arthritis & Rheumatism 65(11):2737-2747.

(56) References Cited

OTHER PUBLICATIONS

Volkmann, E.R. et al. (Feb. 22, 2019). "Emerging Targets Of Disease-Modifying Therapy For Systemic Sclerosis," Nature Reviews Rheumatology, Nature Publishing Group, GB, 15(4):208-224.
Winstone, T.A. et al. (Aug. 2014). "Predictors Of Mortality And Progression In Scleroderma-Associated Interstitial Lung Disease: A Systematic Review," Chest 146(2):422-436.
Wirnsberger, G. et al. (2006). "IL-4 Induces Expression Of TARC/CCL 17 Via Two STAT6 Binding Sites," European Journal Of Immunology 36(7):1882-1891.
International Preliminary Report on Patentability issued Nov. 16, 2021, dated Sep. 16, 2020, for PCT Patent Application No. PCT/US2020/034342, filed May 22, 2020, 9 pages.
International Search Report dated Sep. 16, 2020, for PCT Patent Application No. PCT/US2020/034342, filed May 22, 2020, 17 pages.

* cited by examiner

```
                       SEQUENCE LISTING

<160> NUMBER OF SEQ ID NOS: 23

<210> SEQ ID NO 1
<211> LENGTH: 111
<212> TYPE: PRT
<213> ORGANISM: Artificial Sequence
<220> FEATURE:
<223> OTHER INFORMATION: Synthetic Construct

<400> SEQUENCE: 1

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80
```

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser
        115

<210> SEQ ID NO 3
<211> LENGTH: 108
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Arg
            100                 105

<210> SEQ ID NO 4
<211> LENGTH: 124
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 5
<211> LENGTH: 124
<212> TYPE: PRT

```
<213> ORGANISM: Artificial Sequence
<220> FEATURE:
<223> OTHER INFORMATION: Synthetic Construct

<400> SEQUENCE: 5

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Ala Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala
        115                 120

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gly Gly Gly Gly Ser Gly Gly Gly Gly Ser
1               5                   10

<210> SEQ ID NO 7

<400> SEQUENCE: 7

000

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Arg Ala Ser Glu Ser Val Asp Ser Tyr Gly Gln Ser Tyr Met His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Leu Ala Ser Asn Leu Glu Ser
1               5

<210> SEQ ID NO 10
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 10

Gln Gln Asn Ala Glu Asp Ser Arg Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gly Phe Ser Leu Thr Asp Ser Ser Ile Asn
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Asp Gly Arg Ile Asp
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Asp Gly Tyr Phe Pro Tyr Ala Met Asp Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

His Ala Ser Gln Asn Ile Asp Val Trp Leu Ser
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Lys Ala Ser Asn Leu His Thr Gly
1               5

<210> SEQ ID NO 16
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 16

Gln Gln Ala His Ser Tyr Pro Phe Thr
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Gly Tyr Ser Phe Thr Ser Tyr Trp Ile His
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Ile Asp Pro Ser Asp Gly Glu Thr Arg
1               5

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Leu Lys Glu Tyr Gly Asn Tyr Asp Ser Phe Tyr Phe Asp Val
1               5                   10

<210> SEQ ID NO 20

<400> SEQUENCE: 20

000

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Ile Asp Ala Ser Asp Gly Glu Thr Arg
1               5

<210> SEQ ID NO 22
<211> LENGTH: 335
<212> TYPE: PRT
<213> ORGANISM: Artificial Sequence
<220> FEATURE:
<223> OTHER INFORMATION: Synthetic Construct

<400> SEQUENCE: 22

Asp Ile Val Leu Thr Gln Ser Pro Ala Ser Leu Ala Val Ser Leu Gly

```
1               5                   10                  15
Gln Arg Ala Thr Ile Ser Cys Arg Ala Ser Glu Ser Val Asp Ser Tyr
                20                  25                  30

Gly Gln Ser Tyr Met His Trp Tyr Gln Gln Lys Ala Gly Gln Pro Pro
                35                  40                  45

Lys Leu Leu Ile Tyr Leu Ala Ser Asn Leu Glu Ser Gly Val Pro Ala
                50                  55                  60

Arg Phe Ser Gly Ser Gly Ser Arg Thr Asp Phe Thr Leu Thr Ile Asp
65                      70                  75                  80

Pro Val Gln Ala Glu Asp Ala Ala Thr Tyr Tyr Cys Gln Gln Asn Ala
                    85                  90                  95

Glu Asp Ser Arg Thr Phe Gly Gly Gly Thr Lys Leu Glu Ile Lys Gly
                100                 105                 110

Gly Gly Gly Ser Gly Gly Gly Ser Asp Ile Gln Met Thr Gln Ser
                115                 120                 125

Pro Ala Ser Leu Ser Val Ser Val Gly Asp Thr Ile Thr Leu Thr Cys
                130                 135                 140

His Ala Ser Gln Asn Ile Asp Val Trp Leu Ser Trp Phe Gln Gln Lys
145                 150                 155                 160

Pro Gly Asn Ile Pro Lys Leu Leu Ile Tyr Lys Ala Ser Asn Leu His
                165                 170                 175

Thr Gly Val Pro Ser Arg Phe Ser Gly Ser Gly Ser Gly Thr Gly Phe
                180                 185                 190

Thr Leu Thr Ile Ser Ser Leu Gln Pro Glu Asp Ile Ala Thr Tyr Tyr
                195                 200                 205

Cys Gln Gln Ala His Ser Tyr Pro Phe Thr Phe Gly Gly Gly Thr Lys
                210                 215                 220

Leu Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
                260                 265                 270

Asn Ala Leu Gln Ser Gly Asn Ser Gln Glu Ser Val Thr Glu Gln Asp
                275                 280                 285

Ser Lys Asp Ser Thr Tyr Ser Leu Ser Ser Thr Leu Thr Leu Ser Lys
                290                 295                 300

Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335
```

<210> SEQ ID NO 23
<211> LENGTH: 577
<212> TYPE: PRT
<213> ORGANISM: Artificial Sequence
<220> FEATURE:
<223> OTHER INFORMATION: Synthetic Construct

<400> SEQUENCE: 23

```
Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
                20                  25                  30

Ser Ile Asn Trp Val Arg Gln Pro Pro Gly Lys Gly Leu Glu Trp Leu
```

-continued

```
                35                  40                  45
Gly Met Ile Trp Gly Asp Gly Arg Ile Asp Tyr Ala Asp Ala Leu Lys
 50                  55                  60
Ser Arg Leu Ser Ile Ser Lys Asp Ser Ser Lys Ser Gln Val Phe Leu
 65                  70                  75                  80
Glu Met Thr Ser Leu Arg Thr Asp Asp Thr Ala Thr Tyr Tyr Cys Ala
                 85                  90                  95
Arg Asp Gly Tyr Phe Pro Tyr Ala Met Asp Phe Trp Gly Gln Gly Thr
                100                 105                 110
Ser Val Thr Val Ser Ser Gly Gly Gly Ser Gly Gly Gly Gly Ser
                115                 120                 125
Gln Val Gln Leu Gln Gln Ser Gly Pro Glu Leu Val Lys Pro Gly Ala
                130                 135                 140
Ser Val Lys Ile Ser Cys Lys Ala Ser Gly Tyr Ser Phe Thr Ser Tyr
145                 150                 155                 160
Trp Ile His Trp Ile Lys Gln Arg Pro Gly Gln Gly Leu Glu Trp Ile
                165                 170                 175
Gly Met Ile Asp Pro Ser Asp Gly Glu Thr Arg Leu Asn Gln Arg Phe
                180                 185                 190
Gln Gly Arg Ala Thr Leu Thr Val Asp Glu Ser Thr Ser Thr Ala Tyr
                195                 200                 205
Met Gln Leu Arg Ser Pro Thr Ser Glu Asp Ser Ala Val Tyr Tyr Cys
210                 215                 220
Thr Arg Leu Lys Glu Tyr Gly Asn Tyr Asp Ser Phe Tyr Phe Asp Val
225                 230                 235                 240
Trp Gly Ala Gly Thr Leu Val Thr Val Ser Ser Ala Ser Thr Lys Gly
                245                 250                 255
Pro Ser Val Phe Pro Leu Ala Pro Cys Ser Arg Ser Thr Ser Glu Ser
                260                 265                 270
Thr Ala Ala Leu Gly Cys Leu Val Lys Asp Tyr Phe Pro Glu Pro Val
                275                 280                 285
Thr Val Ser Trp Asn Ser Gly Ala Leu Thr Ser Gly Val His Thr Phe
                290                 295                 300
Pro Ala Val Leu Gln Ser Ser Gly Leu Tyr Ser Leu Ser Ser Val Val
305                 310                 315                 320
Thr Val Pro Ser Ser Ser Leu Gly Thr Lys Thr Tyr Thr Cys Asn Val
                325                 330                 335
Asp His Lys Pro Ser Asn Thr Lys Val Asp Lys Arg Val Glu Ser Lys
                340                 345                 350
Tyr Gly Pro Pro Cys Pro Pro Cys Pro Ala Pro Glu Phe Glu Gly Gly
                355                 360                 365
Pro Ser Val Phe Leu Phe Pro Pro Lys Pro Lys Asp Thr Leu Met Ile
                370                 375                 380
Ser Arg Thr Pro Glu Val Thr Cys Val Val Val Asp Val Ser Gln Glu
385                 390                 395                 400
Asp Pro Glu Val Gln Phe Asn Trp Tyr Val Asp Gly Val Glu Val His
                405                 410                 415
Asn Ala Lys Thr Lys Pro Arg Glu Glu Gln Phe Asn Ser Thr Tyr Arg
                420                 425                 430
Val Val Ser Val Leu Thr Val Leu His Gln Asp Trp Leu Asn Gly Lys
                435                 440                 445
Glu Tyr Lys Cys Lys Val Ser Asn Lys Gly Leu Pro Ser Ser Ile Glu
450                 455                 460
```

```
Lys Thr Ile Ser Lys Ala Lys Gly Gln Pro Arg Glu Pro Gln Val Tyr
465                 470                 475                 480

Thr Leu Pro Pro Ser Gln Glu Glu Met Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Arg Leu Thr Val Asp
        530                 535                 540

Lys Ser Arg Trp Gln Glu Gly Asn Val Phe Ser Cys Ser Val Met His
545                 550                 555                 560

Glu Ala Leu His Asn His Tyr Thr Gln Lys Ser Leu Ser Leu Ser Leu
                565                 570                 575

Gly
```

METHODS FOR TREATING SYSTEMIC SCLEROSIS

CROSS-REFERENCE TO RELATED APPLICATIONS

This application claims the priority benefit of U.S. Provisional Application No. 62/852,941, filed May 24, 2019, European Patent Application No. EP19306309.6, filed Oct. 8, 2019, and U.S. Provisional Application No. 62/979,875, filed Feb. 21, 2020, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952031800SEQLIST.TXT, date recorded: May 21, 2020, size: 16 KB).

FIELD OF THE INVENTION

The present invention relates to bispecific anti-IL-4-anti-IL-13 antibodies for treating systemic sclerosis (also called scleroderma).

BACKGROUND

Systemic sclerosis (also called scleroderma) is a chronic, disabling condition characterized by three pivotal features: immune dysregulation, small vessel vasculopathy, and fibrosis. There are two major subgroups in the commonly accepted classification of systemic sclerosis (SSc): limited cutaneous SSc (lcSSc) and diffuse cutaneous SSc (dcSSc) (LeRoy E. C., et al., *J. Rheumatol.* 1988, 15(2):202-5). In lcSSc, fibrosis is restricted to the distal upper and lower extremities, with possible facial involvement. While the fibrosis will tend to stabilize within the first several years of development, the condition may continue to evolve in the internal organs particularly in the lungs resulting in the development of pulmonary arterial hypertension (PAH) which is the leading cause of mortality associated with lcSSc in its later stages. In contrast, dcSSc is a rapidly progressive disorder that affects a larger area of the skin beyond the limited form with truncal manifestation likely. These patients will often have early internal organ involvement and more significant systemic symptoms such as arthralgia, tendon friction rubs, and weight loss. Although skin fibrosis is the distinguishing hallmark, the pathological changes in the lungs, gastrointestinal tract, kidneys, and heart ultimately determine the clinical outcome. The extent of skin involvement and its rate of progression, however, may reflect the severity of the visceral organ complications, outcome, and survival (Domsic R. T., et al., *Ann. Rheum. Dis.* 2011, 70(1):104-9; Cottrell T. R., et al., *Ann. Rheum. Dis.* 2014, 73(6):1060-6). Survival in patients with dcSSc has improved over the last several decades; currently the average 10-year survival is estimated to be approximately 70% to 80%. Mortality associated with renal crisis has significantly declined during the last couple of decades with the use of angiotensin-converting enzyme (ACE) inhibitors while pulmonary involvement is the leading cause of death in these patients (Elhai M., et al, *Rheumatology (Oxford)* 2012, 51(6):1017-26; Nikpour M. and Baron M., *Curr. Opin. Rheumatol* 2014, 26(2):131-7; Nihtyanova S. I., et al., *QJM* 2010, 103(2):109-15; Winstone T. A., et al., *Chest* 2014, 146(2):422-36).

The prevalence of SSc in 2014 was estimated to be around 120,000 persons in the U.S. and EU5 (i.e., France, Germany, Italy, Spain, and United Kingdom) nations combined with over 60% of the cases being of the diffuse form. The prevalence may increase by as much as 20% in the future using the new American College of Rheumatology/European League Against Rheumatism (ACR/EULAR) 2013 classification criteria (van den Hoogen F., et al., *Ann. Rheum. Dis.* 2013, 72(11):1747-55), which is more sensitive than the previous ACR 1980 criteria. Overall, the disease is more frequence in women (3-6:1) and in certain races (e.g., black).

Currently, there is no approved therapy for SSc. The general therapeutic strategy is to address specific SSc manifestations (e.g., Raynaud's phenomenon, digital ulcers, gastrointestinal involvement, PAH, etc.) while controlling any underlying inflammatory process of the skin or internal organs with the use of potent immunosuppressive therapies (e.g., cyclophosphamide, mycophenolate mofetil, azathioprine, methotrexate, rituxzimab). Because these immunosuppressive therapies do not target specific pathways related to the fibrotic process, they are not particularly effective and are often fraught with significant side effects. Thus, there is an unmet need to find effective targeted therapies with limited side effect profile for this disease population.

All references cited herein, including patent applications and publications, are incorporated by reference in their entirety.

BRIEF SUMMARY OF THE INVENTION

In some aspects, the invention provides methods for treating systemic sclerosis (SSc) in a human subject with SSc, the methods comprising administering about 200 mg of a dual-V-region bispecific antibody or antigen-binding fragment that specifically binds IL-4 and IL-13 subcutaneously to the subject. In some embodiments, 200 mg of the bispecific antibody is administered to the subject about once per week or about every 5 to 9 days. In some embodiments, the treatment is given for at least about 24 weeks. In some embodiments, the bispecific antibody is in a pharmaceutical formulation. In some embodiments, the pharmaceutical formulation comprises about 100 mg/ml bispecific antibody, about 6.3 mM monobasic sodium phosphate, about 37 mM Tris, about 5% (w/v) sucrose, about 3% (w/v) proline, and about 0.2% (w/v) polysorbate 80, wherein the pH of the formulation is about 7.0. In some embodiments, the formulation is reconstituted from a lyophilized formulation. In some embodiments, the bispecific antibody is administered in combination with another agent. In some embodiments, the another agent is administered before, simultaneous with, or after administration of the bispecific antibody. In some embodiments, the systemic sclerosis is diffuse cutaneous systemic sclerosis.

In some embodiments of the invention, the bispecific antibody or bispecific antibody fragment thereof comprises a light chain polypeptide comprising a light chain variable domain $VL_{hB-B13}$ and a light chain variable domain $VL_{hBD4-8}$, and a heavy chain polypeptide comprising a heavy chain variable domain $VH_{hB-B13}$ and a heavy chain variable domain $VH_{hBD4-8}$; wherein: $VL_{hB-B13}$ comprises the three CDRs comprising the amino acid sequences RAS-ESVDSYGQSYMH (SEQ ID NO: 8), LASNLES (SEQ ID NO: 9), and QQNAEDSRT (SEQ ID NO: 10); $VL_{hBD4-8}$ comprises the three CDRs comprising the amino acid sequences HASQNIDVWLS (SEQ ID NO: 14), KASNLHTG (SEQ ID NO: 15), and QQAHSYPFT (SEQ ID NO: 16); $VH_{hB-B13}$ comprises the three CDRs comprising the amino acid sequences GFSLTDSSIN (SEQ ID NO: 11), DGRID (SEQ ID NO: 12), and DGYFPYAMDF (SEQ ID NO: 13); $VH_{hBD4-8}$ comprises the three CDRs comprising the amino acid sequences GYSFTSYWIH (SEQ ID NO: 17), IDPSDGETR (SEQ ID NO: 18) and LKEYGNY-DSFYFDV (SEQ ID NO: 19). In some embodiments, $VL_{hB-B13}$ comprises an amino acid sequence at least 95% identical to the amino acid sequence of SEQ ID NO:1; $VL_{hBD4-8}$ comprises an amino acid sequence at least 95% identical to the amino acid sequence of SEQ ID NO:3; $VH_{hB-B13}$ comprises an amino acid sequence at least 95% identical to the amino acid sequence of SEQ ID NO:2; $VH_{hBD4-8}$ comprises an amino acid sequence at least 95% identical to the amino acid sequence of SEQ ID NO:4. In some embodiments, $VL_{hB-B13}$ comprises the amino acid sequence of SEQ ID NO:1; $VL_{hBD4-8}$ comprises the amino acid sequence of SEQ ID NO:3; $VH_{hB-B13}$ comprises the amino acid sequence of SEQ ID NO:2, $VH_{hBD4-8}$ comprises the amino acid sequence of SEQ ID NO:4. In some embodiments, the light chain polypeptide comprises the structure N-$VL_{hB-B13}$-linker-$VL_{hBD4-8}$-CL-C and the heavy chain polypeptide comprises the structure N-$VH_{hB-B13}$-linker-$VH_{hBp4-8}$-CL-C. In some embodiments, the light chains comprise the structure N-$VL_{hB-B13}$-linker-$VL_{hBD4-8}$-CL-C and the heavy chains comprise the structure N-$VH_{hB-B13}$-linker-$VH_{hBp4-8}$-CH1-CH2-CH3-C. In some embodiments, the linker comprises the amino acid sequence of SEQ ID NO:6. In some embodiments, the bispecific antibody or bispecific antibody fragment thereof comprises two identical light chain polypeptides and two identical heavy chain polypeptides. In some embodiments, the light chain polypeptide comprises an amino acid sequence having at least about 90% identity to the amino acid sequence of SEQ ID NO:22 and the heavy chain polypeptide comprises an amino acid sequence having at least about 90% identity to the amino acid sequence of SEQ ID NO:23. In some embodiments, the light chain polypeptide comprises the amino acid sequence of SEQ ID NO:22 and the heavy chain polypeptide comprises the amino acid sequence of SEQ ID NO:23.

In some aspects, the invention provides methods of reducing sclerotic plaques in a human subject with SSc, the method comprising administering an effective amount of an anti-IL4/anti-IL13 bispecific antibody to said subject; wherein the sclerotic plaques are reduced by at least about 20%, 40%, 60%, 80% or 100% at about 24 weeks after initial administration of the bispecific antibody compared to baseline. In some embodiments, the baseline is determined prior to treatment. In some embodiments, the baseline is a normal control from individuals without scleroderma. In some embodiments, the baseline is a historical control. In some embodiments, a portion of the treated human subjects with SSC have an improved modified Rodnan Skin Score (mRSS) of at least about 20%, 40%, and 60% at about 24 weeks after initial administration of the bispecific antibody compared to baseline. In some embodiments, the improved mRSS is measured as the least square mean change from baseline. In some embodiments, the least square mean change from baseline is more than about any of −3.00, −3.5, −4.0, −4.5, −5.0, −5.5, or −6.0.

In some embodiments of the methods of reducing sclerotic plaques in a human subject with SSc, the anti-IL4/anti-IL13 antibody is RKB. In some embodiments, about 200 mg of the anti-IL4/anti-IL13 antibody is administered subcutaneously to the subject. In some embodiments, 200 mg of the bispecific antibody is administered to the subject about once per week or about every 5 to 9 days. In some embodiments, the treatment is given for at least about 24 weeks. In some embodiments, the bispecific antibody is in a pharmaceutical formulation. In some embodiments, the pharmaceutical formulation comprises about 100 mg/ml bispecific antibody, about 6.3 mM monobasic sodium phosphate, about 37 mM Tris, about 5% (w/v) sucrose, about 3% (w/v) proline, and about 0.2% (w/v) polysorbate 80, wherein the pH of the formulation is about 7.0. In some embodiments, the formulation is reconstituted from a lyophilized formulation. In some embodiments, the bispecific antibody is administered in combination with another agent. In some embodiments, the another agent is administered before, simultaneous with, or after administration of the bispecific antibody. In some embodiments, the systemic sclerosis is diffuse cutaneous systemic sclerosis.

In some embodiments of the methods of reducing sclerotic plaques in a human subject with SSc, the bispecific antibody or bispecific antibody fragment thereof comprises a light chain polypeptide comprising a light chain variable domain $VL_{hB-B13}$ and a light chain variable domain $VL_{hBD4-8}$, and a heavy chain polypeptide comprising a heavy chain variable domain $VH_{hB-B13}$ and a heavy chain variable domain $VH_{hBD4-8}$, wherein: $VL_{hB-B13}$ comprises the three CDRs comprising the amino acid sequences RAS-ESVDSYGQSYMH (SEQ ID NO: 8), LASNLES (SEQ ID NO: 9), and QQNAEDSRT (SEQ ID NO: 10); $VL_{hBD4-8}$ comprises the three CDRs comprising the amino acid sequences HASQNIDVWLS (SEQ ID NO: 14), KASNLHTG (SEQ ID NO: 15), and QQAHSYPFT (SEQ ID NO: 16); $VH_{hB-B13}$ comprises the three CDRs comprising the amino acid sequences GFSLTDSSIN (SEQ ID NO: 11), DGRID (SEQ ID NO: 12), and DGYFPYAMDF (SEQ ID NO: 13); $VH_{hBD4-8}$ comprises the three CDRs comprising the amino acid sequences GYSFTSYWIH (SEQ ID NO: 17), IDPSDGETR (SEQ ID NO: 18) and LKEYGNY-DSFYFDV (SEQ ID NO: 19). In some embodiments, $VL_{hB-B13}$ comprises an amino acid sequence at least 95% identical to the amino acid sequence of SEQ ID NO:1; $VL_{hBD4-8}$ comprises an amino acid sequence at least 95% identical to the amino acid sequence of SEQ ID NO:3; $VH_{hB-B13}$ comprises an amino acid sequence at least 95% identical to the amino acid sequence of SEQ ID NO:2; $VH_{hBD4-8}$ comprises an amino acid sequence at least 95% identical to the amino acid sequence of SEQ ID NO:4. In some embodiments, $VL_{hB-B13}$ comprises the amino acid sequence of SEQ ID NO:1; $VL_{hBD4-8}$ comprises the amino acid sequence of SEQ ID NO:3; $VH_{hB-B13}$ comprises the amino acid sequence of SEQ ID NO:2, $VH_{hBD4-8}$ comprises the amino acid sequence of SEQ ID NO:4. In some embodiments, the light chain polypeptide comprises the structure N-$VL_{hB-B13}$-linker-$VL_{hBD4-8}$-CL-C and the heavy chain polypeptide comprises the structure N-$VH_{hB-B13}$-linker-$VH_{hBD4-8}$-CH1-C. In some embodiments, the light chains comprise the structure N-$VL_{hB-B13}$-linker-$VL_{hBD4-8}$-CL-C and the heavy chains comprise the structure N-$VH_{hB-B13}$-linker-$VH_{hBD4-8}$-CH1-CH2-CH3-C. In some embodiments, the linker comprises the amino acid sequence of SEQ ID NO:6. In some embodiments, the bispecific antibody or bispecific antibody fragment thereof comprises two identical light chain polypeptides and two identical heavy chain polypeptides. In some embodiments, the light chain polypeptide comprises an amino acid sequence having at least about 90% identity to the amino acid sequence of SEQ ID NO:22 and the heavy chain polypeptide comprises an amino acid sequence having at least about 90% identity to the amino acid sequence of SEQ ID NO:23. In some embodiments, the light chain polypeptide comprises the amino acid sequence of SEQ ID NO:22 and the heavy chain polypeptide comprises the amino acid sequence of SEQ ID NO:23.

DETAILED DESCRIPTION

Figure 1:
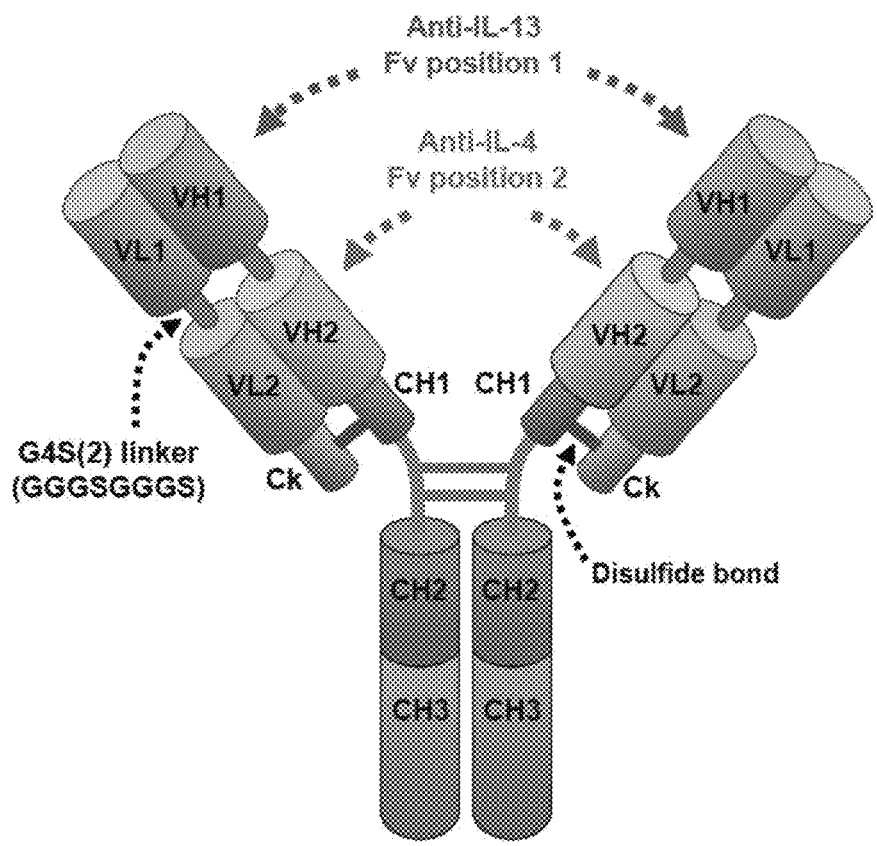
FIG. 1 is a diagram of an exemplary bispecific anti-IL-4/anti-IL-13 antibody comprising two light chain polypeptides and two heavy chain polypeptides. The two light chains comprise the moiety N-VL$_{hB-B13}$-linker-VL$_{hBD4-8}$-CL-C and the two heavy chain polypeptides comprise the moiety N-VH$_{hB-B13}$-linker-VH$_{hBD4-8}$-CH1-CH2-CH3-C. The linker sequence comprises (G$_4$S)$_2$; i.e., GGGGSGGGGS (SEQ ID NO:6).

Each publication, patent application, patent, and other reference cited herein is explicitly incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, New York (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The following non-limiting definitions of some terms and phrases are provided to guide the artisan.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P-NH2) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

"Interleukin-4" (IL-4) relates to the naturally occurring, or endogenous mammalian IL-4 proteins and to proteins having an amino acid sequence which is the same as that of a naturally occurring or endogenous corresponding mammalian IL-4 protein; e.g., recombinant proteins, synthetic proteins (i.e., produced using the methods of synthetic organic chemistry). Accordingly, as defined herein, the term includes mature IL-4 protein, polymorphic or allelic variants, and other isoforms of an IL-4 and modified or unmodified forms of the foregoing (e.g., lipidated, glycosylated). Naturally occurring or endogenous IL-4 includes wild type proteins such as mature IL-4, polymorphic or allelic variants and other isoforms and mutant forms which occur naturally in mammals (e.g., humans, non-human primates). Such proteins can be recovered or isolated from a source which naturally produces IL-4, for example. These proteins and proteins having the same amino acid sequence as a naturally occurring or endogenous corresponding IL-4, are referred to by the name of the corresponding mammal. For example, where the corresponding mammal is a human, the protein is designated as a human IL-4. Several mutant IL-4 proteins are known in the art, such as those disclosed in WO 03/038041.

"Interleukin-13" (IL-13) refers to naturally occurring or endogenous mammalian IL-13 proteins and to proteins having an amino acid sequence which is the same as that of a naturally occurring or endogenous corresponding mammalian IL-13 protein (e.g., recombinant proteins, synthetic proteins (i.e., produced using the methods of synthetic organic chemistry)). Accordingly, as defined herein, the term includes mature IL-13 protein, polymorphic or allelic variants, and other isoforms of IL-13 (e.g., produced by alternative splicing or other cellular processes), and modified or unmodified forms of the foregoing (e.g., lipidated, glycosylated). Naturally occurring or endogenous IL-13 include wild type proteins such as mature IL-13, polymorphic or allelic variants and other isoforms and mutant forms which occur naturally in mammals (e.g., humans, non-human primates). For example, as used herein IL-13 encompasses the human IL-13 variant in which Arg at position 110 of mature human IL-13 is replaced with Gln (position 110 of mature IL-13 corresponds to position 130 of the precursor protein) which is associated with asthma (atopic and nonatopic asthma) and other variants of IL-13. (Heinzmann el al., *Hum Mol Genet.* (2000) 9:549-559). Such proteins can be recovered or isolated from a source which naturally produces IL-13, for example. These proteins and proteins having the same amino acid sequence as a naturally occurring or endogenous corresponding IL-13 are referred to by the name of the corresponding mammal. For example, where the corresponding mammal is a human, the protein is designated as a human IL-13. Several mutant IL-13 proteins are known in the art, such as those disclosed in WO 03/035847.

In some aspects, the invention relates to the treatment of systemic sclerosis (SSc). In some embodiments, the invention relates to treatment of diffuse cutaneous systemic sclerosis (dcSSc). In some embodiments, the invention relates to the treatment of limited cutaneous SSc (lcSSc). IL-4 and IL-13 are therapeutically important cytokines based on their biological functions and play critical roles in many diseases, including asthma (*Curr Opin Allergy Clin Immunol* 2005, Vo. 5, 161-166). IL-4 has been shown to be able to inhibit autoimmune disease and IL-4 and IL-13 have both shown the potential to enhance anti-tumor immune responses. Since both cytokines are involved in the pathogenesis of allergic diseases or fibrotic diseases, inhibitors of these cytokines could provide therapeutic benefits.

The phrase "substantially identical" with respect to an antibody chain polypeptide sequence may be construed as an antibody chain exhibiting at least 70%, 80%, 90%, 95%, 96%, 97%, 98%, 99% or more sequence identity to the reference polypeptide sequence. The term with respect to a nucleic acid sequence may be construed as a sequence of nucleotides exhibiting at least about 85%, 90%, 95%, 96%, 97%, 98%, 99% or more sequence identity to the reference nucleic acid sequence. Identity can be determined by using any bioinformatics tool available to one skilled in the art. For example, Basic Local Alignment Search Tool (BLAST) is commonly employed to determine sequence identity (Altschul et al., *J. Mol. Biol.* (1990) 215:403-410).

The terms, "identity" or "homology" may mean the percentage of nucleotide bases or amino acid residues in the candidate sequence that are identical with the residue of a corresponding sequence to which it is compared, after aligning the sequences and introducing gaps, if necessary, to achieve the maximum percent identity for the entire sequence, and not considering any conservative substitutions as part of the sequence identity. Neither N-terminal or C-terminal extensions nor insertions shall be construed as reducing identity or homology. Methods and computer programs for the alignment are available and well known in the art. Sequence identity may be measured using sequence analysis software.

"Substitutional" variants are those that have at least one amino acid residue in a native sequence removed and replaced with a different amino acid inserted in its place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion. "Insertional" variants are those with one or more amino acids inserted immediately adjacent to an amino acid at a particular position in a native sequence. Immediately adjacent to an amino acid means connected to either the a-carboxyl or a-amino functional group of the amino acid. "Deletional" variants are those with one or more amino acids in the native amino acid sequence removed. Ordinarily, deletional variants will have one or two amino acids deleted in a particular region of the molecule.

The term "antibody" is used in the broadest sense, and specifically covers monoclonal antibodies (including full length monoclonal antibodies), polyclonal antibodies, multispecific antibodies (e.g., bispecific antibodies), antigen binding antibody fragments or synthetic polypeptides carrying one or more CDR or CDR-derived sequences so long as the polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity. The antibodies of the invention can be of any class (e.g., IgG, IgE, IgM, IgD, IgA and so on), or subclass (e.g., IgG1, IgG2, IgG2a, IgG3, IgG4, lgA1; lgA2and so on) ("type" and "class", and "subtype" and ""subclass", are used interchangeably herein). Native or wildtype, that is, obtained from a non-artificially manipulated member of a population, antibodies and immunoglobulins are usually heterotetrameric glycoproteins of about 150,000 daltons, composed of two identical light (L) chains and two identical heavy (H) chains. Each heavy chain has at one end a variable domain (VH) followed by a number of constant domains. Each light chain has a variable domain at one end (VL) and a constant domain at the other end. By "non-artificially manipulated" is meant not treated to contain or express a foreign antigen binding molecule. Wildtype can refer to the most prevalent allele or species found in a population or to the antibody obtained from a non-manipulated animal, as compared to an allele or polymorphism, or a variant or derivative obtained by a form of manipulation, such as mutagenesis, use of recombinant methods and so on to change an amino acid of the antigen-binding molecule.

As used herein, "anti-IL-4 antibody" means an antibody or polypeptide derived therefrom (a derivative) which binds specifically to IL-4 as defined herein, including, but not limited to, molecules which inhibit or substantially reduce the binding of IL-4 to its receptor or inhibit IL-4 activity.

As used herein, "anti-IL-13 antibody" means an antibody or polypeptide derived therefrom (a derivative) which binds specifically to IL-13 as defined herein, including, but not limited to, molecules which inhibit or substantially reduce the binding of IL-13 to its receptor or inhibit IL-13 activity.

As used herein, "anti-IL-4/anti-IL-13 bispecific antibody" means a bispecific antibody or polypeptide derived therefrom (a derivative) which binds specifically to IL-4 and/or IL-13 as defined herein, including, but not limited to, molecules which inhibit or substantially reduce the binding of IL-4 to its receptor or inhibit IL-4 activity and/or substantially reduce the binding of IL-13 to its receptor or inhibit IL-13 activity.

The term "variable" in the context of a variable domain of antibodies refers to certain portions of the pertinent molecule which differ extensively in sequence between and among antibodies and are used in the specific recognition and binding of a particular antibody for its particular target. However, the variability is not evenly distributed through the variable domains of antibodies. The variability is concentrated in three segments called complementarity determining regions (CDRs; i.e., CDR1, CDR2, and CDR3) also known as hypervariable regions, both in the light chain and the heavy chain variable domains. The more highly conserved portions of variable domains are called the framework (FR) regions or sequences. The variable domains of native heavy and light chains each comprise four FR regions, largely adopting a β-sheet configuration, connected by three CDRs, which form loops connecting, and in some cases forming part of, the β-sheet structure. The CDRs in each chain are held together often in proximity by the FR regions and, with the CDRs from the other chain, contribute to the formation of the target (epitope or determinant) binding site of antibodies (see Kabat et al. Sequences of Proteins of Immunological Interest, National Institute of Health, Bethesda, MD (1987)). As used herein, numbering of immunoglobulin amino acid residues is done according to the immunoglobulin amino acid residue numbering system of Kabat et al., unless otherwise indicated. One CDR can carry the ability to bind specifically to the cognate epitope.

The term "hinge" or "hinge region" as used in the present invention refers to the flexible polypeptide comprising the amino acids between the first and second constant domains of an antibody.

The phrases and terms "fragment," "functional fragment," "variant," "derivative," or "analog" and the like, as well as forms thereof, of an antibody, antigen, or antigen-binding protein is a compound or molecule having qualitative biological activity in common with a full-length antibody or antigen of interest. For example, a functional fragment or analog of an anti-IL-4 antibody is one that can bind to an IL-4 molecule, or that can prevent or substantially reduce the ability of a ligand, or an agonistic or antagonistic antibody, to bind to IL-4. In another example, a functional fragment or analog of an anti-IL-13 antibody is one that can bind to an IL-13 molecule, or that can prevent or substantially reduce the ability of a ligand, or an agonistic or antagonistic antibody, to bind to IL-13. In yet another example, a functional fragment or analog of an anti-IL-4/anti-IL-13 bispecific antibody is one that can bind to an IL-4 molecule and/or an IL-13 molecule, or that can prevent or substantially reduce the ability of a ligand, or an agonistic or antagonistic antibody, to bind to IL-4 and/or IL-13.

In addition, the terms "fragment" and "antibody fragment" refer to a portion of an intact or a full-length chain or an antibody, generally the target binding or variable region. In some examples, a fragment of antibody fragment of an antibody-like binding molecule comprises an antigen binding domain. With regard to a bispecific antibody-like binding molecule, the molecule comprises two or more antigen binding domains. For example, a fragment or analog of an anti-IL-4 and/or IL-13 antibody is one which can prevent or substantially reduce the ability of the receptor to bind to a ligand or to initiate signaling. As used herein, "fragment," "functional fragment," and "antibody fragment" generally refer to antibodies which can prevent or substantially reduce the ability of the receptor to bind to a ligand or to initiate signaling.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as they exhibit the desired biological activity of binding to IL-4 and/or IL-13 or impacting IL-4 and/or IL-13 activity or metabolism (U.S. Pat. No. 4,816,567; and Morrison et al. (1984), *Proc Natl Acad Sci USA* 81:6851). Thus, CDRs from one class of antibody can be grafted into the FR of an antibody of different class or subclass.

Monoclonal antibodies are highly specific, being directed against a specific target sites, epitopes or determinants. Furthermore, in contrast to conventional (polyclonal) antibody preparations which typically include different antibodies directed against different determinants (epitopes) of an antigen, each monoclonal antibody is directed against specific determinant on the target. In addition to their specificity, monoclonal antibodies are advantageous being synthesized by a host cell, uncontaminated by other immunoglobulins, and provides for cloning the relevant gene and mRNA encoding the antibody of chains thereof. The modifier "monoclonal" indicates the character of the antibody as being obtained from a substantially homogeneous population of antibodies, and is not to be construed as requiring production of the antibody by any particular method. The parent monoclonal antibodies to be used in accordance with the present invention may be made by the hybridoma method described by Kohler et al. (1975), *Nature* 256:495, or may be made by recombinant methods well known in the art.

The term "polyvalent antibody" as used in the present invention refers to an antibody comprising two or more antigen binding sites, thus being able to bind two or more antigens, which may have the same or a different structure, simultaneously. The term "bivalent" means that the antibody comprises two antigen binding sites. The term "tetravalent" means that the antibody comprises four antigen binding sites.

The term "antigen binding site" as used in the present invention refers to the part of the antibody which comprises the area which specifically binds to and is complementary to part or all of an antigen. Where an antigen is large, an antibody may only bind to a particular part of the antigen, which part is termed on epitope. An antigen binding domain may be provided by one or more antibody variable domains. Preferably, an antigen binding domain is made of the association of an antibody light chain variable domain (VL) and an antibody heavy chain variable domain (VH).

The term "antigen" as used in the present invention refers to a molecule or a portion of a molecule capable of being bound by the antibodies of the present invention. An antigen can have one or more than one epitope. Examples of antigens recognized by the antibodies of the present invention include, but are not limited to, serum proteins, e.g. cytokines such as IL-4, IL-5, IL-9 and IL-13, bioactive peptides, cell surface molecules, e.g. receptors, transporters, ion-channels, viral and bacterial proteins.

The term "monospecific" as used in the present invention means that the polyvalent antibody of the present invention recognizes only one antigen, all the antigen binding sites being identical.

The term "bispecific" as used in the present invention means that the polyvalent antibody of the present invention recognizes two different epitopes on the same or on two different antigens.

The term "bispecific antibody" (BsAb) refers to molecules which combine the antigen-binding sites of two antibodies within a single molecule. Thus, a bispecific antibody is able to bind two different antigens simultaneously. Besides applications for diagnostic purposes, BsAbs pave the way for new therapeutic applications by redirecting potent effector systems to diseased areas or by increasing neutralizing or stimulating activities of antibodies.

It has been of interest to produce bispecific antibodies (BsAbs) which combine the antigen-binding sites of two antibodies within a single molecule. Thus, such a molecule would be able to bind two different antigens simultaneously. Besides applications for diagnostic purposes, they pave the way for new therapeutic applications, e.g. by redirecting potent effector systems to diseased areas (where cancerous cells often develop mechanisms to suppress normal immune responses triggered by monoclonal antibodies, like antibody-dependent cellular cytotoxicity (ADCC) or complement-dependent cytotoxicity (CDC)), or by increasing neutralizing or stimulating activities of antibodies. Initial attempts to couple the binding specificities of two whole antibodies against different target antigens for therapeutic purposes utilized chemically fused heteroconjugate molecules (Staerz et al. (1985), *Nature* 314: 628-631).

Bispecific antibodies were originally made by fusing two hybridomas, each capable of producing a different immunoglobulin (Milstein and Cuello, 1983, 1984), but the complexity of species (up to ten different species) produced in cell culture makes purification difficult and expensive (George and Huston, 1997). Despite the promising results obtained using heteroconjugates or bispecific antibodies produced from cell fusions as cited above, several factors made them impractical for large scale therapeutic applications. Such factors include: rapid clearance of heteroconjugates in vivo, the laboratory intensive techniques required for generating either type of molecule, the need for extensive purification of heteroconjugates away from homoconjugates or mono-specific antibodies and generally low yields.

Genetic engineering has been used with increasing frequency to design, modify, and produce antibodies or antibody derivatives with a desired set of binding properties and effector functions. A variety of recombinant methods have been developed for efficient production of BsAbs, both as antibody fragments (Carter et al. (1995), *J. Hematotherapy* 4: 463-470; Pluckthun et al. (1997) *Immunotechology* 3: 83-105; Todorovska et al. (2001) *J. Immunol. Methods* 248: 47-66) and full length IgG formats (Carter (2001) *J. Immunol. Methods* 248: 7-15).

Abbott described in US patent U.S. Pat. No. 7,612,181 a murine Dual-Variable-Domain IgG (DVD-IgG) bispecific antibody, which is based on the dual-Fv format described in Unilever patent (U.S. Pat. No. 5,989,830). A humanized bispecific format was described in WO2009/052081 (TBTI) which is incorporated herein by reference in its entirety. The addition of constant domains to respective chains of the Dual-Fv (CHI-Fc to the heavy chain and kappa or lambda constant domain to the light chain) led to functional bispecific dual-V-region antibody like binding proteins.

The term "multispecific" as used in the present invention means that the polyvalent antibody of the present invention recognizes multiple different epitopes on the same or on multiple different antigens.

The term "linker" as used in the present invention refers to a peptide adapted to connect the variable domains of the antibody constructs of the present invention. The peptide linker may contain any amino acids, the amino acids glycine (G) and serine (S) being preferred. The linkers may be equal or differ from each other between and within the heavy chain polypeptide and the light chain polypeptide. Furthermore, the linker may have a length of 1, 2, 3, 4, 5, 6, 7, 8, 9, 10, 11, 12, 13, 14, 15, 16, 17, 18, 19 or 20 amino acids. In some embodiments, the peptide linker unit for the heavy chain domains and for the light chain domains is GGGGS. The numbers of linker units of the heavy chain and of the light chain may be equal (symmetrical order) or differ from each other (asymmetrical order). In some embodiments, the peptide linker comprises two units for the heavy chain domains and for the light chain domains (e.g., GGGGSGGGGS; SEQ ID NO:6).

A peptide linker is preferably long enough to provide an adequate degree of flexibility to prevent the antibody moieties from interfering with each others activity, for example by steric hindrance, to allow for proper protein folding and, if necessary, to allow the antibody molecules to interact with two or more, possibly widely spaced, receptors on the same cell; yet it is preferably short enough to allow the antibody moieties to remain stable in the cell. Therefore, the length, composition and/or conformation of the peptide linkers can readily be selected by one skilled in the art in order to optimize the desired properties of the polyvalent antibody.

"Humanized" forms of non-human (e.g., murine) antibodies are chimeric immunoglobulins, immunoglobulin chains or fragments thereof which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region (Fc), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to IL-4 and/or IL-13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., *Prot Eng* 7(6)805-814, 1994; *Mol Imm* 44:1986-1988, 2007; Sims et al., *J Immunol* 151:2296 (1993); Chothia et al., *J Mot Biol* 196:901 (1987); Carter et al., *Proc Natl Acad Sci USA* 89:4285 (1992); Presta et al., *J Immunol* 151:2623 (1993), WO 2006/042333 and U.S. Pat. No. 5,869,619.

"Antibody homolog" or "homolog" when used in reference to IL-4 and/or IL-13 refers to any molecule which specifically binds IL-4 and/or IL-13 as taught herein. Thus, an antibody homolog includes native or recombinant antibody, whether modified or not, portions of antibodies that retain the biological properties of interest, such as binding IL-4 or IL-13, such as an Fab or Fv molecule, a single chain antibody, a polypeptide carrying one or more CDR regions and so on. The amino acid sequence of the homolog need not be identical to that of the naturally occurring antibody but can be altered or modified to carry substitute amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of a IL-4, IL-13 or bispecific IL-4/IL-13 antibody of the present invention. Preferably, homology is with the amino acid sequence of the variable regions of an antibody of the present invention. "Sequence homology" as applied to an amino acid sequence herein is defined as a sequence with at least about 90%, 91%, 92%, 93%, 94%, 95%, 96%, 97%, 98% or 99% sequence homology to another amino acid sequence, as determined, for example, by the FASTA search method in accordance with Pearson & Lipman, *Proc Natl Acad Sci USA* 85, 2444-2448 (1988).

A chimeric antibody is one with different portions of an antibody derived from different sources, such as different antibodies, different classes of antibody, different animal species, for example, an antibody having a variable region derived from a murine monoclonal antibody paired with a human immunoglobulin constant region and so on. Thus, a humanized antibody is a species of chimeric antibody. Methods for producing chimeric antibodies are known in the art, see, e.g., Morrison, 1985, *Science* 229:1202; Oi et al., 1986, *BioTechniques* 4:214; Gillies et al., 1989, *J Immunol Methods* 125:191-202; and U.S. Pat. Nos. 5,807,715, 4,816, 567, and 4,816,397.

Also included within the scope of the invention are functional equivalents of an antibody of interest. The term "functional equivalents" includes antibodies with homologous sequences, antibody homologs, chimeric antibodies, artificial antibodies and modified antibodies, for example, wherein each functional equivalent is defined by the ability to bind to IL-4 and/or IL-13, inhibiting IL-4 and/or IL-13 signaling ability or function, or inhibiting binding of IL-4 and/or IL-13 to its receptor. The skilled artisan will understand that there is an overlap in the group of molecules termed "antibody fragments" and the group termed "functional equivalents." Methods of producing functional equivalents which retain IL-4 and/or IL-13 binding ability are known to the person skilled in the art and are disclosed, for example, in WO 93/21319, EPO Ser. No. 239,400, WO 89/09622, EPO Ser. No. 338,745 and EPO Ser. No. 332,424.

The functional equivalents of the present application also include modified antibodies; e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein etc. The covalent attachment need not yield an antibody that is immune from generating an anti-idiotypic response. The modifications may be achieved by known techniques, including, but not limited to, specific chemical cleavage, acetylation, formylation, metabolic synthesis etc. Additionally, the modified antibodies may contain one or more non-classical amino acids.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5% or 1%, (by dry weight) of contaminating protein. When the antibody is recombinantly produced, it is also preferably substantially free of culture medium, i.e., culture medium represents less than about 20%, 10%, 5%, 2.5% or 1% of the volume of the protein preparation. When antibody is produced by chemical synthesis, it is preferably substantially free of chemical precursors or other chemicals and reagents, i.e., the antibody of interest is separated from chemical precursors or other chemicals which are involved in the synthesis of the protein. Accordingly, such preparations of the antibody have less than about 30%, 20%, 10%, 5% or 1% (by dry weight) of chemical precursors or compounds other than antibody of interest. In some embodiments of the present invention, antibodies are isolated or purified. In some embodiments, the invention provides compositions comprising an anti-IL-4/anti-IL-13 bispecific antibody, wherein greater than any of about 95%, 96%, 97%, 98%, 99%, of the polypeptides in the composition are the anti-IL-4/anti-IL-13 bispecific antibody.

As used herein, the terms "therapeutic agent" and "therapeutic agents" refer to any agent(s) which can be used in the treatment, management or amelioration of a disease, disorder, malady and the like associated with aberrant IL-4 and/or IL-13 metabolism and activity.

As used herein, "dose" refers to the quantity of any agent(s) which can be used in the treatment, management or amelioration of a disease, disorder, malady and the like associated with aberrant IL-4 and/or IL-13 metabolism and activity.

As used herein, "safe dose" refers to any agent(s) or dose of any agent(s) which can be used in the treatment, management or amelioration of a disease, disorder, malady and the like associated with aberrant IL-4 and/or IL-13 metabolism and activity while maintaining a clinically acceptable benefit/risk profile. A safe dose of the dual-V-region antibody-like binding proteins or fragments thereof disclosed herein is selected from the group consisting of 10 mg, 20 mg, 40 mg, 50 mg, 80 mg, 100 mg, 150 mg, 200 mg, and 300 mg. An embodiment of a safe dose is about 10 mg to about 300 mg. A further embodiment of a safe dose of a is any dose that is 200 mg, about 200 mg, up to 200 mg, or no greater than about 200 mg. In other embodiments, a safe dose is about 50 mg, or about 100 mg, or about 200 mg. In some embodiments, the safe dose is administered once weekly. In some embodiments, the safe dose is administered once every 7±2 days (i.e., every 5-9 days). In some embodiments, the safe dose is administered every other week (i.e. biweekly). In some embodiments, the safe dose is administered subcutaneously (SC). In some embodiments, the safe dose is administered subcutaneously (SC) over a period of at least about 24 weeks. In some embodiments, 200 mg of the bispecific antibody is administered once weekly. In some embodiments, 200 mg of the bispecific antibody is administered once every 7±2 days (i.e., every 5-9 days). In some embodiments, 200 mg of the bispecific antibody is administered every other week (i.e. biweekly). In some embodiments, 200 mg of the bispecific antibody is administered subcutaneously (SC). In some embodiments, 200 mg of the bispecific antibody is administered subcutaneously (SC) one weekly over a period of at least about 24 weeks.

Reference to "about" a value or parameter herein includes (and describes) embodiments that are directed to that value or parameter per se. For example, description referring to "about X" includes description of "X." The term "about" when used in connection with a numerical value is meant to encompass numerical values within a range having a lower limit that is 5%, 10%, or 15% smaller than the indicated numerical value and having an upper limit that is 5%, 10%, or 15% larger than the indicated numerical value and includes that indicated numerical value.

Anti-IL4-anti-IL13 Bispecific Antibodies

In some aspects, the invention provides methods for treating SSc by administering a bispecific antibody that binds IL-4 and IL-13. A bispecific dual-variable-region (dual-V-region) antibody-like binding protein having four binding sites that specifically bind to IL-4 and IL-13 has been reported in WO 2009/052081, WO 2012/125775, WO 2015/121318, WO 2014/177568 and WO 2015/198146, each of which are incorporated by reference herein in its entirety.

An embodiment of the invention is methods for treating SSc using a bispecific antibody that has been engineered to comprise a dual-V-region antibody-like protein or fragment thereof that specifically binds to two different epitopes on the same or on two different antigens.

In some embodiments, the light chain variable regions (VL) and heavy chain variable regions (VH) of the dual-V region antibody-like binding molecules have the following sequences (CDR sequences are shown in bold).

$VL_{hB-B13}$
(SEQ ID NO: 1)
DIVLTQSPAS LAVSLGQRAT ISCRASESVD SYGQSYMHWY

QQKAGQPPKL LIYLASNLES GVPARFSGSG SRTDFTLTID

PVQAEDAATY YCQQNAEDSR TFGGGTKLEI K $VH_{hB-B13}$
(SEQ ID NO: 2)
EVQLKESGPG LVAPGGSLSI TCTVSGFSLT DSSINWVRQP

PGKGLEWLGM IWGDGRIDYA DALKSRLSIS KDSSKSQVFL

EMTSLRTDDT ATYYCARDGY FPYAMDFWGQ GTSVTVSS $VL_{h8D4-8}$
(SEQ ID NO: 33)
DIQMTQSPAS LSVSVGDTIT LTCHASQNID VWLSWFQQKP

GNIPKLLIYK ASNLHTGVPS RFSGSGSGTG FTLTISSLQP

EDIATYYCQQ AHSYPFTFGG GTKLEIKR $VH_{h8D4-8}$
(SEQ ID NO: 4)
QVQLQQSGPE LVKPGASVKI SCKASGYSFT SYWIHWIKQR

PGQGLEWIGM IDPSDGETRL NQRFQGRATL TVDESTSTAY

MQLRSPTSED SAVYYCTRLK EYGNYDSFYF DVWGAGTLVT

VSSA
or
(SEQ ID NO: 5)
QVQLQQSGPE LVKPGASVKI SCKASGYSFT SYWIHWIKQR

PGQGLEWIGM IDASDGETRL NQRFQGRATL TVDESTSTAY

MQLRSPTSED SAVYYCTRLK EYGNYDSFYF DVWGAGTLVT

VSSA

In some aspects, the invention provides methods for treating SSc by administering a bispecific antibody or bispecific antigen binding antibody fragment thereof that specifically binds IL-13 and IL-4 to a subject, wherein the bispecific antibody or bispecific antigen binding antibody fragment comprises a light chain polypeptide comprising a light chain variable domain $VL_{hB-B13}$ and a light chain variable domain $VL_{hBD4-8}$; an a heavy chain polypeptice comprising a heavy chain variable domain $VH_{hB-B13}$ and a heavy chain variable domain $VH_{hBD4-8}$; wherein:

$VL_{hB-B13}$ comprises three CDRs comprising the amino acid sequences

```
                                       (SEQ ID NO: 8)
RASESVDSYGQSYMH,
                                       (SEQ ID NO: 9)
LASNLES,
and
                                       (SEQ ID NO: 10)
QQNAEDSRT;
```

$VL_{hBD4-8}$ comprises three CDRs comprising the amino acid sequences

```
                                       (SEQ ID NO: 14)
HASQNIDVWLS,
                                       (SEQ ID NO: 15)
KASNLHTG,
and
                                       (SEQ ID NO: 16)
QQAHSYPFT;
```

$VH_{hB-B13}$ comprises three CDRs comprising the amino acid sequences GFSLTDSSIN (SEQ ID NO: 11), DGRID (SEQ ID NO: 12), and DGYFPYAMDF (SEQ ID NO: 13); and $VH_{hBD4-8}$ comprises three CDRs comprising the amino acid sequences GYSFTSYWIH (SEQ ID NO: 17), IDPSDGETR (SEQ ID NO: 18) and LKEYGNYDSFYFDV (SEQ ID NO: 19) or the amino acid sequences GYSFTSYWIH (SEQ ID NO: 17), IDASDGETR (SEQ ID NO: 21), and LKEYGNYDSFYFDV (SEQ ID NO: 19).

In some embodiments, the invention provides methods for treating SSc by administering a bispecific antibody or bispecific antigen binding antibody fragment thereof that specifically binds IL-13 and IL-4 to a subject, wherein the bispecific antibody or bispecific antigen binding antibody fragment comprises a light chain polypeptide comprising a light chain variable domain $VL_{hB-B13}$ and a light chain variable domain $VL_{hBD4-8}$ and a heavy chain polypeptide comprising a heavy chain variable domain $VH_{hB-B13}$ and a heavy chain variable domain $VH_{hBD4-8}$; wherein:

$VL_{hB-B13}$ comprises CDRs comprising the amino acid sequences RASESVDSYGQSYMH (SEQ ID NO: 8), LASNLES (SEQ ID NO: 9), and QQNAEDSRT (SEQ ID NO: 10) and VLhB-B13 comprises an amino acid sequence at least 95% identical to the amino acid sequence of SEQ ID NO:1;

$VL_{hBD4-8}$ comprises CDRs comprising the amino acid sequences HASQNIDVWLS (SEQ ID NO: 14), KASNLHTG (SEQ ID NO: 15), and QQAHSYPFT (SEQ ID NO: 16) and VLhBD4-8 comprises an amino acid sequence at least 95% identical to the amino acid sequence of SEQ ID NO:3;

$VH_{hB-B13}$ comprises CDRs comprising the amino acid sequences GFSLTDSSIN (SEQ ID NO: 11), DGRID (SEQ ID NO: 12), and DGYFPYAMDF (SEQ ID NO: 13) and VHhB-B13 comprises an amino acid sequence at least 95% identical to the amino acid sequence of SEQ ID NO:2; and $VH_{hBD4-8}$ comprises CDRs comprising the amino acid sequences GYSFTSYWIH (SEQ ID NO: 17), IDPSDGETR (SEQ ID NO: 18) and LKEYGNYDSFYFDV (SEQ ID NO: 19) and VHhBD4-8 comprises an amino acid sequence at least 95% identical to the amino acid sequence of SEQ ID NO:4, or $VH_{hBD4-8}$ comprises CDRs comprising the amino acid sequences the amino acid sequences GYSFTSYWIH (SEQ ID NO: 17), IDASDGETR (SEQ ID NO: 21), and LKEYGNYDSFYFDV (SEQ ID NO: 19) and VHhBD4-8 comprises an amino acid sequence at least 95% identical to the amino acid sequence of SEQ ID NO:5.

In some embodiments, the invention provides methods for treating SSc by administering a bispecific antibody or bispecific antigen binding antibody fragment thereof that specifically binds IL-13 and IL-4 to a subject, wherein the bispecific antibody or bispecific antigen binding antibody fragment comprises a light chain polypeptide comprising a light chain variable domain $VL_{hB-B13}$ and a light chain variable domain $VL_{hBD4-8}$; and a heavy chain polypeptide comprising a heagy chain variable domain $VH_{hB-B13}$ and a heavy chain variable domain $VH_{hBD4-8}$; wherein:

$VL_{hB-B13}$ comprises the amino acid sequence of SEQ ID NO:1, $VL_{hBD4-8}$ comprises the amino acid sequence of SEQ ID NO:3, $VH_{hB-B13}$ comprises the amino acid sequence of SEQ ID NO:2, $VH_{hBD4-8}$ comprises the amino acid sequence of SEQ ID NO:4 or SEQ ID NO:5.

In some embodiments of the bispecific antibody or bispecific antigen binding antibody fragment thereof described above, the light chain polypeptides comprise the structure N-$VL_{hB-B13}$-linker-$VL_{hBD4-8}$-CL-C and the heavy chain polypeptides comprise the structure N-$VH_{hB-B13}$-linker-$VH_{hBp4-8}$-CH1-C. In some embodiments of the bispecific antibody or bispecific antigen binding antibody fragment thereof described above, the light chain polypeptides comprise the structure N-$VL_{hB-B13}$-linker-$VL_{hBD4-8}$-CL-C and the heavy chain polypeptides comprise the structure N-$VH_{hB-B13}$-linker-$VH_{hBp4-8}$-CH1-CH2-CH3-C. In some embodiments, the linker comprises the amino acid sequence of SEQ ID NO:6.

In some embodiments of the bispecific antibody or bispecific antigen binding antibody fragment thereof described above, the light chain polypeptides comprise the sequence:

```
                                              (SEQ ID NO: 22)
DIVLTQSPAS LAVSLGQRAT ISCRASESVD SYGQSYMHWY

QQKAGQPPKL LIYLASNLES GVPARFSGSG SRTDFTLTID

PVQAEDAATY YCQQNAEDSR TFGGGTKLEI KGGGGSGGGG

SDIQMTQSPA SLSVSVGDTI TLTCHASQNI DVWLSWFQQK

PGNIPKLLIY KASNLHTGVP SRFSGSGSGT GFTLTISSLQ

PEDIATYYCQ QAHSYPFTFG GGTKLEIKRT VAAPSVFIFP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC
```

In some embodiments of the bispecific antibody or bispecific antigen binding antibody fragment thereof described above, the heavy chain polypeptides comprise the sequence:

```
                                            (SEQ ID NO: 23)
EVQLKESGPG LVAPGGSLSI TCTVSGFSLT DSSINWVRQP

PGKGLEWLGM IWGDGRIDYA DALKSRLSIS KDSSKSQVFL

EMTSLRTDDT ATYYCARDGY FPYAMDFWGQ GTSVTVSSGG

GGSGGGGSQV QLQQSGPELV KPGASVKISC KASGYSFTSY

WIHWIKQRPG QGLEWIGMID PSDGETRLNQ RFQGRATLTV

DESTSTAYMQ LRSPTSEDSA VYYCTRLKEY GNYDSFYFDV

WGAGTLVTVS SASTKGPSVF PLAPCSRSTS ESTAALGCLV

KDYFPEPVTV SWNSGALTSG VHTFPAVLQS SGLYSLSSVV

TVPSSSLGTK TYTCNVDHKP SNTKVDKRVE SKYGPPCPPC

PAPEFEGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLG
```

In some embodiments of the bispecific antibody or bispecific antigen binding antibody fragment thereof described above, the light chain polypeptides comprise the structure N-VL$_{hBD4-8}$-linker-VL$_{hB-B13}$-CL-C and the heavy chain polypeptides comprise the structure N-VH$_{hBD4-8}$-linker-VH$_{hB-B13}$-CH1-C. In some embodiments of the bispecific antibody or bispecific antigen binding antibody fragment thereof described above, the light chain polypeptides comprise the structure N-VL$_{hBD4-8}$-linker-VL$_{hB-B13}$-CL-C and the heavy chain polypeptides comprise the structure N-VH$_{hBp4-8}$-linker-VH$_{BD-B13}$-CH1-CH2-CH3-C. In some embodiments, the linker comprises the amino acid sequence of SEQ ID NO:6.

In some embodiments of the bispecific antibody or bispecific antigen binding antibody fragment thereof described above, the bispecific antibody or bispecific antigen binding antibody fragment thereof comprises two light chains and two heavy chains. In some embodiments, the bispecific antibody or bispecific antigen binding antibody fragment is derived from an IgG4 antibody.

In some embodiments, the invention provides methods for treating SSc by administering an antibody antigen binding fragment thereof that specifically binds IL-13 to a subject, wherein the antibody or antibody fragment thereof comprises a light chain variable domain comprising CDRs having the amino acid sequences RASESVDSYGQSYMH (SEQ ID NO: 8), LASNLES (SEQ ID NO: 9), and QQNAEDSRT (SEQ ID NO: 10) and a heavy chain variable domain comprising CDRs having the amino acid sequences GFSLTDSSIN (SEQ ID NO: 11), DGRID (SEQ ID NO: 12), and DGYFPYAMDF (SEQ ID NO: 13). In some embodiments, the light chain variable domain comprises an amino acid sequence at least 95% identical to the amino acid sequence of SEQ ID NO:1 and the heavy chain variable domain comprises an amino acid sequence at least 95% identical to the amino acid sequence of SEQ ID NO:2. In some embodiments, the light chain variable domain comprises the amino acid sequence of SEQ ID NO:1 and a heavy chain domain comprises the amino acid sequence of SEQ ID NO:2. In some embodiments, the antibody competes for binding IL-13 with the antibody or antibody fragment described above. In some embodiments, the antibody binds the same epitope as the antibody or antibody fragment described above. In some embodiments, the antibody is a bispecific antibody or bispecific antibody fragment thereof. In some embodiments, the antibody specifically binds IL-13 and IL-4.

In some embodiments, the invention provides methods for treating SSc by administering an antibody antigen binding fragment thereof that specifically binds IL-4 to a subject, wherein the antibody or antibody fragment thereof comprises a light chain variable domain comprising CDRs having the amino acid sequences HASQNIDVWLS (SEQ ID NO: 14), KASNLHTG (SEQ ID NO: 15), and QQAHSYPFT (SEQ ID NO: 16) and a heavy chain variable domain comprising CDRs having the amino acid sequences GYSFTSYWIH (SEQ ID NO: 17), IDPSDGETR (SEQ ID NO: 18) and LKEYGNYDSFYFDV (SEQ ID NO: 19) or the amino acid sequences GYSFTSYWIH (SEQ ID NO: 17), IDASDGETR (SEQ ID NO: 21), and LKEYGNYDSFYFDV (SEQ ID NO: 19). In some embodiments, the light chain variable domain comprises an amino acid sequence at least 95% identical to the amino acid sequence of SEQ ID NO:3 and the heavy chain variable domain comprises an amino acid sequence at least 95% identical to the amino acid sequence of SEQ ID NO:4 or SEQ ID NO:5. In some embodiments, the light chain variable domain comprises the amino acid sequence of SEQ ID NO:3 and a heavy chain domain comprises the amino acid sequence of SEQ ID NO:4 or SEQ ID NO:5. In some embodiments, the antibody competes for binding IL-4 with the antibody or antibody fragment described above. In some embodiments, the antibody binds the same epitope as the antibody or antibody fragment described above. In some embodiments, the antibody is a bispecific antibody or bispecific antibody fragment thereof. In some embodiments, the antibody specifically binds IL-4 and IL-13.

In some embodiments of the bispecific antibody or bispecific antigen binding antibody fragment thereof described above, the bispecific antibody or bispecific antigen binding antibody fragment competes for binding of IL-13 and/or IL-4 with a bispecific antibody or bispecific antigen binding antibody fragment thereof described above. In some embodiments of the bispecific antibody or bispecific antigen binding antibody fragment thereof described above, the bispecific antibody or bispecific antigen binding antibody fragment binds the same epitopes as a bispecific antibody or bispecific antigen binding antibody fragment thereof described above.

In some aspects, the invention provides methods for treating SSc by administering to a subject a pharmaceutical composition comprising a bispecific antibody or bispecific antigen binding antibody fragment thereof that specifically binds IL-13 and IL-4 as described above. In some embodiments, the pharmaceutical composition comprises a bispecific antibody or bispecific antigen binding antibody fragment thereof that specifically binds IL-13 and IL-4 as described above and a pharmaceutically acceptable carrier.

In some aspects, the invention provides compositions for treating SSc wherein the composition comprises a bispecific antibody or bispecific antigen binding antibody fragment thereof that specifically binds IL-13 and IL-4 as described above. In some embodiments, the composition is formulated to provide a dose of about 200 mg of the bispecific antibody of bispecific antigen binding antibody fragment thereof to the subject. In some embodiments, the composition is formulated to provide a dose of about 200 mg of the bispecific antibody of bispecific antigen binding antibody fragment thereof to the subject once a week. In some embodiments, the composition is formulated to provide a dose of about 200 mg of the bispecific antibody of bispecific antigen binding antibody fragment thereof to the subject once every other week. In some embodiments, the composition is formulated to provide a dose of 200 mg of the bispecific antibody of bispecific antigen binding antibody fragment thereof to the subject once every 7 days±2 days. In some embodiments, the composition is formulated to provide a dose of 200 mg of the bispecific antibody of bispecific antigen binding antibody fragment thereof to the subject once every 5-9 days. In some embodiments, the composition is formulated to provide a dose of about 200 mg of the bispecific antibody of bispecific antigen binding antibody fragment thereof to the subject once a week. In some embodiments, the composition is formulated to provide a dose of about 200 mg of the bispecific antibody of bispecific antigen binding antibody fragment thereof subcutaneously to the subject once a week for at least about 24 weeks.

In some embodiments, the invention provides uses of a bispecific antibody or bispecific antigen binding antibody fragment thereof that specifically binds IL-13 and IL-4 as described above in the manufacture of a medicament for treating SSc in a subject. In some embodiments, the composition is formulated to provide a dose of about 200 mg of the bispecific antibody of bispecific antigen binding antibody fragment thereof to the subject. In some embodiments, the medicament is formulated to provide a dose of about 200 mg of the bispecific antibody of bispecific antigen binding antibody fragment thereof to the subject once a week. In some embodiments, the medicament is formulated to provide a dose of about 200 mg of the bispecific antibody of bispecific antigen binding antibody fragment thereof to the subject once every other week. In some embodiments, the medicament is formulated to provide a dose of about 200 mg of the bispecific antibody of bispecific antigen binding antibody fragment thereof to the subject once every other week. In some embodiments, the medicament is formulated to provide a dose of about 200 mg of the bispecific antibody of bispecific antigen binding antibody fragment thereof to the subject once a week for at least about 24 weeks. In some embodiments, the medicament is formulated to provide a dose of 200 mg of the bispecific antibody of bispecific antigen binding antibody fragment thereof to the subject once a week. In some embodiments, the medicament is formulated to provide a dose of about 200 mg of the bispecific antibody of bispecific antigen binding antibody fragment thereof subcutaneously to the subject once a week for at least about 24 weeks.

In some embodiments, the invention provides methods for treating SSc by administering to a subject with SSc, huTBTI3_2_1 or SAR156597 or Romilkimab (RKB) comprising a bispecific antibody or bispecific antigen binding antibody fragment thereof that specifically binds to IL-13 and IL-4, comprising (a) light chain polypeptides comprising two variable light chain domains, wherein one variable light chain domain comprises the amino acid sequences of SEQ ID NO:1 and one variable light chain domain comprises the amino acid sequences of SEQ ID NO:3; (b) heavy chain polypeptides comprising two variable heavy chain domains, wherein one variable heavy chain domain comprises the amino acid sequence of SEQ ID NO:2 and one variable heavy chain domain comprises the amino acid sequence of SEQ ID NO:4; (c) a peptide linker linking SEQ ID NO:1 to SEQ ID NO:3, and a peptide linker linking SEQ ID NO:2 to SEQ ID NO:4 wherein the peptide linker has an amino acid sequence consisting of SEQ ID NO:6; and (d) constant region domains.

To prolong the serum circulation of an antibody in vivo, various techniques can be used. For example, inert polymer molecules, such as high molecular weight polyethylene glycol (PEG), can be attached to an antibody with or without a multifunctional linker either through site-specific conjugation of the PEG to the N-terminus or to the C-terminus of the antibody or via ɛ amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion exchange chromatography. PEG-derivatized antibodies can be tested for binding activity as well as for in vivo efficacy using methods known to those of skilled in the art, for example, by immunoassays described herein.

An antibody having an increased half-life in vivo can also be generated by introducing one or more amino acid modifications (i.e., substitutions, insertions or deletions) into an IgG constant domain, or FCR binding fragment thereof (such as an Fc or hinge Fc domain fragment), see, e.g., WO 98/23289; WO 97/34631; and U.S. Pat. No. 6,277,375.

Further, an antibody can be conjugated to albumin to make an antibody more stable in vivo or have a longer half life in vivo. The techniques are known in the art, see e.g., WO 93/15199, WO 93/15200 and WO 01/77137; and EPO 413,622. The antibody also can be modified, for example, by glycosylation, acetylation, phosphorylation, amidation, derivatization by known protecting/blocking groups, proteolytic cleavage, linkage to a cellular ligand or other protein and so on.

Antibodies of the instant invention also may be described or specified in terms of binding affinity to IL-4 and/or IL-13. Anti-IL-4 and/or anti-IL-13 antibodies may bind with a $K_D$ of less than about $10^{-7}$M, less than about $10^{-6}$ M, or less than about $10^{-5}$M. Higher binding affinities in an antibody of interest can be beneficial, such as those with an equilibrium dissociation constant or $K_D$ of from about $10^{-8}$ to about $10^{-15}$M, from about $10^{-8}$ to about $10^{-12}$ M, from about $10^{-9}$ to about $10^{-11}$M, or from about $10^{-8}$ to about $10^{-10}$ M. The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least about 95%, at least about 90%, at least about 85%, at least about 80%, at least about 75%, at least about 70%, at least about 60%, or at least about 50%.

The antibodies of the present invention may be administered and/or formulated together with one or more additional therapeutic or active agents. When a ligand is administered with an additional therapeutic agent, the ligand can be administered before, simultaneously with or subsequent to administration of the additional agent. Generally, the ligand and additional agent are administered in a manner that provides an overlap of therapeutic effect. Additional agents that can be administered or formulated with the ligand of the invention include, for example, various immunotherapeutic drugs, such as cylcosporine, methotrexate, adriamycin or cisplatin, antibiotics, antimycotics, anti-viral agents and immunotoxins. For example, when the antagonist is administered to prevent, suppress or treat lung inflammation or a respiratory disease (e.g., asthma), it can be administered in conjuction with phosphodiesterase inhibitors (e.g., inhibitors of phosphodiesterase 4), bronchodilators (e.g., β2-agonists, anticholinergerics, theophylline), short-acting beta-agonists (e.g., albuterol, salbuiamol, bambuterol, fenoter[sigma]l, isoetherine, isoproterenol, leva[iota]buterol, metaproterenol, pirbuterol, terbutaline and tornlate), long-acting beta-agonists (e.g., formoterol and salmeterol), short acting anticholinergics (e.g., ipratropium bromide and oxitropium bromide), long-acting anticholinergics (e.g., tiotropium), theophylline (e.g. short acting formulation, long acting formulation), inhaled steroids (e.g., beclomethasone, beclometasone, budesonide, flunisolide, fluticasone propionate and triamcinolone), oral steroids (e.g., methylprednisolone, prednisolone, prednisolon and prednisone), combined short-acting beta-agonists with anticholinergics (e.g., albuterol/salbutamol/ipratopium, and fenoterol/ipratopium), combined long-acting beta-agonists with inhaled steroids (e.g., salmeterol/fluticasone, and formolerol/budesonide) and mucolytic agents (e.g., erdosteine, acetylcysteine, bromheksin, carbocyslcine, guiafencsin and iodinated glycerol.

Other suitable co-therapeutic agents that can be administed with antibody of the present invention to prevent, suppress or treat asthma (e.g., allergic asthma), include a corticosteroid (e.g., beclomethasone, budesonide, fluticasone), cromoglycate, nedocromil, beta-agonist (e.g., salbutamol, terbutaline, bambuterol, fenoterol, reproterol, tolubuterol, salmeterol, fomtero), zafirlukast, salmeterol, prednisone, prednisolone, theophylline, zileutron, montelukast, and leukotriene modifiers. The ligands of the invention can be coadministered with a variety of co-therapeutic agents suitable for treating diseases (e.g., SSc, a Th-2 mediated disease, YL-A-mediated disease, IL-13 mediated disease, and IL-4 mediated disease), including cytokines, analgesics/antipyretics, antiemetics, and chemotherapeutics.

Antibodies of the invention may be provided in pharmaceutically acceptable compositions as known in the art or as described herein. The term "physiologically acceptable," "pharmacologically acceptable" and so on mean approved by a regulatory agency of the Federal or a state government or listed in the U.S. Pharmacopeia or other generally recognized pharmacopeia for use in animals and more particularly in humans.

The bispecific anti-IL-4/IL-13 antibodies may be administered to a mammal and in particular humans to treat SSc, in any acceptable manner. Methods of introduction include, but are not limited to, parenteral, subcutaneous, intraperitoneal, intrapulmonary, intranasal, epidural, inhalation and oral routes, and if desired for immunosuppressive treatment, intralesional administration. Parenteral infusions include intramuscular, intradermal, intravenous, intraarterial or intraperitoneal administration. The antibodies or compositions may be administered by any convenient route, for example, by infusion or bolus injection, by absorption through epithelial or mucocutaneous linings (e.g., oral mucosa, rectal and intestinal mucosa etc.) and may be administered together with other biologically active agents. Administration can be systemic or local. In addition, it may be desirable to introduce the therapeutic antibodies or compositions of the invention into the central nervous system by any suitable route, including intraventricular and intrathecal injection; intraventricular injection may be facilitated by an intraventricular catheter, for example, attached to a reservoir, such as an Ommaya reservoir. In addition, the antibody is suitably administered by pulse infusion, particularly with declining doses of the antibody. In some embodiments, the bispecific anti-IL-4/IL-13 antibodies are administered subcutaneously to a human subject.

Therapeutic formulations of the polypeptide or antibody may be prepared for storage as lyophilized formulations or aqueous solutions by mixing the polypeptide having the desired degree of purity with optional "pharmaceutically acceptable" carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

Examples of formulations of dual-V region bispecific antibody-like molecules that bind IL-4 and IL-13 are provided in WO 2014/177568, incorporated herein by reference in its entirety. Highly stable anti-IL-4/anti-IL-13 bispecific antibody formulations have surprisingly been found in the form of liquids and lyophilized powders that comprise an anti-IL-4/anti-IL-13 bispecific antibody and a buffering system, wherein the pH of the formulation is about pH 7, and wherein the formulation has a low salt concentration in order to reduce the ionic strength of the formulation. The formulations may, optionally, further comprise a non-ionic surfactant, a sugar, and/or a non-ionic stabilizing agent. These formulations improve upon conventional formulations, which often lead to molecular aggregation (HMW) of the antibody upon increasing the concentration of the antibody in the formulation, and the formation of visible and subvisible particles. In particular, the formulations of the invention exhibit good stability regarding visible particles, subvisible particles, low molecular weight proteins, and high molecular weight proteins.

In some embodiments, the invention provides a stable antibody formulation comprising: a bispecific anti-IL-4/anti-IL-13 antibody or an antigen binding fragment thereof, comprising a light chain of the formula VL1-linker-VL2 and a heavy chain of the formula VH1-linker-VH2, wherein VL1 and VH1 form an IL-13 antigen binding domain and VL2 and VH2 form an IL-4 antigen binding domain; and a buffering system suitable to maintain the pH of the formulation at about pH 7; and wherein the formulation has a low salt concentration in order to reduce the ionic strength of the formulation. In some embodiments, VL1 comprises the three CDR sequences of SEQ ID NO: 1; VH1 comprises the three CDR sequences of SEQ ID NO: 2; VL2 comprises the three CDR sequences of SEQ ID NO: 3; and VH2 comprises the the CDR sequences of SEQ ID NO: 4 or 5. In alternative specific embodiments, VL1 comprises the amino acid sequence of SEQ ID NO: 1; VH1 comprises the amino acid sequence of SEQ ID NO: 2; VL2 comprises the amino acid sequence of SEQ ID NO: 3; and VH2 comprises the amino acid sequence of SEQ ID NO: 4 or 5. In some embodiments, the light chain comprises the formula N-VL1-linker-VL2-CL, wherein CL is a light chain constant domain of an antibody, and wherein the heavy chain comprises the formula N-VH1-linker-VH2-CH1-CH2-CH3, wherein CH2-CH3 corresponds to the Fc domain of an antibody. In specific embodiments, the linker comprises the amino acid sequence of SEQ ID NO: 6. In some embodiments, the antibody or antigen binding fragment thereof further comprises a constant region domain. In some embodiments, the constant region domain is selected from the group consisting of CHI, CH2, CH3, and CL. In some embodiments, the bispecific antibody or antigen binding fragment thereof is a humanized IgG4 bispecific antibody or antigen binding fragment thereof.

In some embodiments, the concentration of antibody or antigen binding fragment thereof in any of the formulations described above is about 100 mg/mL.

In some embodiments of the invention, the buffering system of any of the formulations described above comprises at least two buffers. In specific embodiments, the buffering system concentration is about 10 mM. In specific embodiments, the buffering system comprises Tris buffer and Phosphate buffer. In specific embodiments, the Tris buffer concentration is about 3.7 mM. In specific embodiments, the Phosphate buffer concentration is about 6.3 mM. In specific embodiments, the Tris buffer concentration is about 3.7 mM and the Phosphate buffer concentration is about 6.3 mM.

In some embodiments of the invention, any of the formulations described above further comprises a non-ionic surfactant. In specific embodiments, the non-ionic surfactant concentration is about 0.05% to about 0.2% (w/v). In specific embodiments, the non-ionic surfactant is a polysorbate. In specific embodiments, the polysorbate is polysorbate 80. In specific embodiments, the polysorbate 80 concentration is about 0.05% to about 0.2% (w/v). In specific embodiments, the polysorbate 80 concentration is about 0.2% (w/v).

In some embodiments of the invention, any of the formulations described above further comprises a sugar. In specific embodiments, the sugar concentration is about 5% (w/v). In specific embodiments, the sugar is a disaccharide. In specific embodiments, the disaccharide is sucrose. In specific embodiments, the sucrose concentration is about 5% (w/v).

In some embodiments of the invention, the formulation further comprises a non-ionic stabilizing agent. In specific embodiments, the non-ionic stabilizing agent concentration is about 1% to about 3% (w/v). In specific embodiments, the non-ionic stabilizing agent is either an amino acid or a sugar. In specific embodiments, the amino acid is proline. In specific embodiments, the sugar is mannitol. In specific embodiments, the proline concentration is about 1% to about 3% (w/v). In specific embodiments, the proline concentration is about 3% (w/v). In specific embodiments, the mannitol concentration is about 3% (w/v).

In some embodiments of the invention, the formulation is a lyophilized formulation. In some embodiments of the invention, the formulation is a reconstituted lyophilized formulation.

In some embodiments of the invention, the formulation exhibits good stability regarding visible particles, sub-visible particles, low molecular weight proteins, and high molecular weight proteins.

An embodiment of the invention provides a method of treating SSc in a subject comprising administering a bispecific anti-IL4/anti-IL-13 antibody or antigen binding fragment thereof wherein the antibody is in stable antibody formulation comprising: about 100 mg/mL of a bispecific antibody or an antigen binding fragment thereof, wherein the antibody or antigen binding fragment thereof comprises a heavy chain polypeptide comprising a variable region comprising the amino acid sequence of SEQ ID NO:2 and a variable region comprising the amino acid sequence of SEQ ID NO:4, and a light chain polypeptide compiling a variable region comprising the amino acid sequence of SEQ ID NO:1 and a variable region comprising the amino acid sequence of SEQ ID NO:3; about 10 mM of a buffering system, wherein the buffering system comprises a Tris buffer concentration of about 3.7 mM and a Phosphate buffer concentration of about 6.3 mM; about 0.2% (w/v) polysorbate 80; about 5% (w/v) sucrose; and about 3% (w/v) proline; wherein the pH of the formulation is about pH 7.

An embodiment of the invention provides a method of treating SSc in a subject comprising administering a bispecific anti-IL4/anti-IL-13 antibody or antigen binding fragment thereof wherein the antibody is in a stable lyophilized antibody formulation comprising: about 100 mg/mL of a bispecific antibody or an antigen binding fragment thereof as described herein; about 10 mM of a buffering system, wherein the buffering system comprises a Tris buffer concentration of about 3.7 mM and a Phosphate buffer concentration of about 6.3 mM; about 0.2% (w/v) polysorbate 80; about 5% (w/v) sucrose; and about 3% (w/v) mannitol; wherein the pH of the formulation is about pH 7.

In some embodiments, the antibodies of the instant invention may be conjugated to various effector molecules such as heterologous polypeptides, drugs, radionucleotides or toxins, see, e.g., WO 92/08495; WO 91/14438; WO 89/12624; U.S. Pat. No. 5,314,995; and EPO 396,387. An antibody or fragment thereof may be conjugated to a therapeutic moiety such as a cytotoxin (e.g., a cytostatic or cytocidal agent), a therapeutic agent or a radioactive metal ion (e.g., a emitters, such as, for example, 213Bi). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracindione, mitoxantrone, mithramycin, actinomycin D, 1-dehydrotestosterone, glucocorticoids, procaine, tetracaine, lidocaine, propranolol and puromycin and analogs or homologues thereof. Therapeutic agents include, but are not limited to, antimetabolites (e.g., methotrexate, 6-mercaptopurine, 6-thioguanine, cytarabine, 5-fluorouracil and decarbazine), alkylating agents (e.g., mechlorethamine, chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyc lines (e.g., daunorubicin, daunomycin and doxorubicin), antibiotics (e.g., dactinomycin, actinomycin, bleomycin, mithramycin and anthramycin (AMC)), and anti-mitotic agents (e.g., vincristine and vinblastine).

Techniques for conjugating such a therapeutic moiety to antibodies are well known, see, e.g., Arnon et al., in Monoclonal Antibodies and Cancer Therapy, Reisfeld et al. (eds.), p. 243-56 Alan R. Liss (1985); Hellstrom et al., in Controlled Drug Delivery, 2nd ed., Robinson et al., eds., p. 623-53, Marcel Dekker (1987); Thorpe, in Monoclonal Antibodies '84: Biological And Clinical Applications, Pinchera et al., eds., p. 475-506 (1985); Monoclonal Antibodies For Cancer Detection and Therapy, Baldwin et al., eds., p. 303-16, Academic Press (1985); and Thorpe, et al., *Immunol Rev* 62:119 (1982). Alternatively, an antibody can be conjugated to a second antibody to form an antibody heteroconjugate, such as a bifunctional antibody, see, e.g., U.S. Pat. No. 4,676,980.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (WO 97/33899), AIM II (WO 97/34911), Fas ligand (Takahashi et al., *Int Immunol*, 6:1567 (1994)), VEGF (WO 99/23105); a thrombotic agent; an anti-angiogenic agent, e.g., angiostatin or endostatin; or biological response modifiers such as, for example, lymphokines, interleukin-1 (IL-I), interleukin-2 (IL-2), interleukin-6 (IL-6), granulocyte macrophage colony stimulating factor (GM-CSF), granulocyte colony stimulating factor (GCSF) or other growth factors.

The formulations to be used for in vivo administration must be sterile. That can be accomplished, for example, by filtration through sterile filtration membranes. For example, the liquid formulations of the present invention may be sterilized by filtration using a 0.2 µm or a 0.22 µm filter.

Methods of Treatment

In some aspects, the invention provides methods for treating SSc in a human subject with SSc, the methods comprising administering about 200 mg of a dual-V-region bispecific antibody or antigen-binding fragment that specifically binds IL-4 and IL-13 as described herein subcutaneously to the subject. In some embodiments, the SSc is diffuse cutaneous systemic sclerosis (dcSSc). In some embodiments, the SSc is limited cutaneous systemic sclerosis (lcSSc). In some embodiments, the about 200 mg of the bispecific antibody is administered to the subject about once per week or about every 5 to 9 days. In some embodiments, the bispecific antibody is administered once every 7±2 days (i.e., every 5-9 days). In some embodiments, the bispecific antibody is administered every other week (i.e. biweekly). In some embodiments, the bispecific antibdoy is administered subcutaneously (SC). In some embodiments, the bispecific antibody is administered subcutaneously (SC) over a period of at least about 24 weeks.

In some embodiments, the bispecific antibody is in a pharmaceutical formulation. In some embodiments, the pharmaceutical formulation comprises about 100 mg/ml bispecific antibody, about 6.3 mM monobasic sodium phosphate, about 37 mM Tris, about 5% (w/v) sucrose, about 3% (w/v) proline, and about 0.2% (w/v) polysorbate 80, wherein the pH of the formulation is about 7.0. In some embodiments, the formulation is reconstituted from a lyophilized formulation.

In some embodiments of any of the methods of treatment described herein, the bispecific antibody or bispecific antibody fragment thereof comprises a light chain polypeptide comprising a light chain variable domain $VL_{hB-B13}$ and a light chain variable domain $VL_{hBD4-8}$, and a heavy chain polypeptide comprising a heavy chain variable domain $VH_{hB-B13}$ and a heavy chain variable domain $VH_{hBD4-8}$; wherein: $VL_{hB-B13}$ comprises the three CDRs comprising the amino acid sequences RASESVDSYGQSYMH (SEQ ID NO: 8), LASNLES (SEQ ID NO: 9), and QQNAEDSRT (SEQ ID NO: 10); $VL_{hBD4-8}$ comprises the three CDRs comprising the amino acid sequences HASQNIDVWLS (SEQ ID NO: 14), KASNLHTG (SEQ ID NO: 15), and QQAHSYPFT (SEQ ID NO: 16), $VH_{hB-B13}$ comprises the three CDRs comprising the amino acid sequences GFSLTDSSIN (SEQ ID NO: 11), DGRID (SEQ ID NO: 12), and DGYFPYAMDF (SEQ ID NO: 13), $VH_{hBD4-8}$ comprises the three CDRs comprising the amino acid sequences GYSFTSYWIH (SEQ ID NO: 17), IDPSDGETR (SEQ ID NO: 18) and LKEYGNYDSFYFDV (SEQ ID NO: 19). In some embodiments, $VL_{hB-B13}$ comprises an amino acid sequence at least 95% identical to the amino acid sequence of SEQ ID NO:1, $VL_{hBD4-8}$ comprises an amino acid sequence at least 95% identical to the amino acid sequence of SEQ ID NO:3, $VH_{hB-B13}$ comprises an amino acid sequence at least 95% identical to the amino acid sequence of SEQ ID NO:2, $VH_{hBD4-8}$ comprises an amino acid sequence at least 95% identical to the amino acid sequence of SEQ ID NO:4. In some embodiments, $VL_{hB-B13}$ comprises the amino acid sequence of SEQ ID NO:1, $VL_{hBD4-8}$ comprises the amino acid sequence of SEQ ID NO:3, $VH_{hB-B13}$ comprises the amino acid sequence of SEQ ID NO:2, $VH_{hBD4-8}$ comprises the amino acid sequence of SEQ ID NO:4. In some embodiments, the light chain polypeptide comprises the structure $N-VL_{hB-B13}$-linker-$VL_{hBD4-8}$-CL-C and the heavy chain polypeptide comprises the structure $N-VH_{hB-B13}$-linker-$VH_{hBD4-8}$-CH1-C. In some embodiments, the light chains comprise the structure $N-VL_{hB-B13}$-linker-$VL_{hBD4-8}$-CL-C and the heavy chains comprise the structure $N-VH_{hB-B13}$-linker-$VH_{hBD4-8}$-CH1-CH2-CH3-C. In some embodiments, the linker comprises the amino acid sequence of SEQ ID NO:6. In some embodiments, the bispecific antibody or bispecific antibody fragment thereof comprises two identical light chain polypeptides and two identical heavy chain polypeptides. In some embodiments, the light chain polypeptide comprises an amino acid sequence having at least about 90% identity to the amino acid sequence of SEQ ID NO:22 and the heavy chain polypeptide comprises an amino acid sequence having at least about 90% identity to the amino acid sequence of SEQ ID NO:23. In some embodiments, the light chain polypeptide comprises the amino acid sequence of SEQ ID NO:22 and the heavy chain polypeptide comprises the amino acid sequence of SEQ ID NO:23. In some embodiments, the anti-IL4/anti-IL13 bispecific antibody is RKB.

In some embodiments, the methods of treatment of scleroderma as described herein with a specific antibody or bispecific antibody fragment thereof is additive with background therapy.

In some aspects, the invention provides a method of reducing sclerotic plaques in a human subject with SSc, the method comprising administering an effective amount of an anti-IL4/anti-IL13 bispecific antibody to said subject; wherein the sclerotic plaques are reduced by at least about 10%, 20%, 30%, 40%, 50%, 60%, 70%, 80%, 90% at about any of 4, 8, 12, 24, 36, 48 or greater than 48 weeks after initial administration of the bispecific antibody compared to baseline. In some embodiments, the sclerotic plaques are reduced by at least about 10%, 20%, 30%, 40%, 50%, 60%, 70%, 80%, 90% at about 24 weeks after initial administration of the bispecific antibody compared to baseline. In some embodiments, the sclerotic plaques are reduced by at least about 10%, 20%, 30%, 40%, 50%, 60%, 70%, 80%, 90% at about 12 weeks after initial administration of the bispecific antibody compared to baseline. In some embodiments, the sclerotic plaques are reduced by at least about 10%, 20%, 30%, 40%, 50%, 60%, 70%, 80%, 90% at about 8 weeks after initial administration of the bispecific antibody compared to baseline. In some embodiments, the sclerotic plaques are reduced by at least about 10%, 20%, 30%, 40%, 50%, 60%, 70%, 80%, 90% at about 4 weeks after initial administration of the bispecific antibody compared to baseline. In some embodiments, the baseline is determined for the human subject with SSc prior to treatment administration of the bispecific antibody. In some embodiments, the baseline is the level in a human subject that does not have SSc. In some embodiments, a portion of the treated human subjects with SSC have an improved modified Rodnan Skin Score (mRSS) of at least about 10%, 20%, 30%, 40%, 50%, 60%, 70%, 80%, 90% at about any of 4, 8, 12, 24, 36 48 or greater than 48 weeks after initial administration of the bispecific antibody compared to baseline. In some embodiments, a portion of the treated human subjects with SSC have an improved mRSS of at least about 10%, 20%, 30%, 40%, 50%, 60%, 70%, 80%, 90% at about 24 weeks after initial administration of the bispecific antibody compared to baseline. In some embodiments, a portion of the treated human subjects with SSC have an improved mRSS of at least about 10%, 20%, 30%, 40%, 50%, 60%, 70%, 80%, 90% at about 12 weeks after initial administration of the bispecific antibody compared to baseline. In some embodiments, a portion of the treated human subjects with SSC have an improved mRSS of at least about 10%, 20%, 30%, 40%, 50%, 60%, 70%, 80%, 90% at about 8 weeks after initial administration of the bispecific antibody compared to baseline. In some embodiments, a portion of the treated human subjects with SSC have an improved mRSS of at least about 10%, 20%, 30%, 40%, 50%, 60%, 70%, 80%, 90% at about 4 weeks after initial administration of the bispecific antibody compared to baseline. The mRSS is conducted by palpation of the skin in 17 areas of the body (fingers, hands, forearms, arms, feet, legs and thighs, face, chest and abdomen) using a 0-3 scale, where 0=normal, 1=mild thickness, 2=moderate thickness and 3=severe thickness. Total skin score can range from 0 (no thickening) to 51 (severe thickening in all 17 areas).

In some embodiments, the inventnion provides a method for improving a health assessment questionnaire disability index (HAQ-DI) in a human subject with scleroderma, the method comprising administering an effective amount of an anti-IL4/anti-IL13 bispecific antibody to said subject; wherein the improvement in HAQ-DI is improved at about any of 4, 8, 12, 24, 36, 45 or greater than 45 weeks after initial administration of the bispecific antibody compared to baseline. In some embodiments, the HAQ-DI is measured by a scleroderma health assessment questionnaire (SHAQ). The SHAQ, which includes the standard HAQ-DI to measure the functional disability and 5 SSc-specific VAS assessments are completed by patients at baseline and during treatment. The SHAQ is the standard, validated, and accepted health assessment questionnaire in patients with SSc to assess the physical/functional disability related to skin and systemic fibrosis.

The HAQ DI contains 8 domains of activity (dressing, arising, eating, walking, hygiene, reach, grip, and common daily activities) each of which has at least 2 questions, for a total of 20 items. For each item, patients report the amount of difficulty experienced performing the activity. There are 4 possible responses for each item ranging from 0 (without any difficulty) to 3 (unable to do). For each of the 8 domains included in the HAQ-DI, the score is the single response within the domain with the highest score. If aids or devices are used, and if the highest score is 0 or 1, then the score is raised to 2; if the highest score is 2 or 3, the score is kept as it is. The HAQ-DI composite score is then calculated as the average of the scores of the 8 domains. If 1 or 2 of the domains are missing, the HAQ-DI composite score is obtained by dividing the sum of the domains by the number of answered domains. If three or more of the domains are missing, then the HAQ-DI composite score is missing. The composite score is reported, falling between 0 and 3 on an ordinal scale. The scores are interpreted as 0 (no impairment in function) to 3 (maximal impairment of function).

The HAQ-DI also contains a VAS that patients use to report the amount of pain experienced in the past week. The VAS is a 10-cm line that is converted to a continuous scale from 0 to 3 where 1 cm is equivalent to 0.3 points. The anchors of the VAS are 0 (no pain) to 100 (very severe pain). To obtain the patient score, a metric ruler was used to measure the distance in centimeters from the left anchor to the patient's mark, and then multiplied by 0.3. The VAS pain score is not incorporated into the HAQ DI composite score.

In some embodiment the invention provide a method of improving respiratory function in a human subject with SSc, the method comprising administering an effective amount of an anti-IL4/anti-IL13 bispecific antibody to said subject; wherein the improvement in respiratory function is measured by predicted Forced Vital Capacity (FVC) and/or predicted carbon monoxide diffusing lung capacity (DLco) at about 4, 8, 12, 24, 36, 48 or more than 48 weeks after initial administration of the bispecific antibody compared to baseline. In some embodiments, the baseline is determined for the human subject with SSc prior to treatment administration of the bispecific antibody. In some embodiments, the baseline is the level in a human subject that does not have SSc.

The pulmonary function test is a secondary endpoint that assess the change in respiratory function as measured by observed FVC and observed DLco (corrected for hemoglobin) from baseline to sampling time. The absolute change in observed and % predicted change in FVC and DLco from baseline to sample time is assessed. The manual correction of DLco for hemoglobin is based upon the following equation unless it is automatically corrected during measurement: 1) For male patients: $DLco_{observed/(factor)}$, where factor is $=(1.7\times Hb)/(10.22+Hb)$; 2) For female patients: $DLco_{observed/(factor)}$, where factor is $=(1.7\times Hb)/(9.38+Hb)$. Hb refers to hemoglobin, and the value are taken from the same visit where the DLco is conducted.

In some embodiments, the invention provides methods for reducing pain, improving vascular function, improving gastrointestinal function, reducing Raynaud's phenomenon and/or reducing digital ulcers in a human subject with SSc, the method comprising administering an effective amount of an anti-IL4/anti-IL13 bispecific antibody to said subject.

In some embodiments, improving gastrointestinal function is measured by UCLA Scleroderma Clinical Trial Consortium Gastrointestinal Tract 2.0 score at about any of 4, 8, 12, 24, 36 48, or greater than 48 weeks after initial administration of the bispecific antibody compared to baseline. In some embodiments, the UCLA Scleroderma Clinical Trial Consortium Gastrointestinal Tract 2.0 score at about 24 weeks after initial administration of the bispecific antibody is improved compared to baseline. The UCLA SCTC GIT 2.0 instrument is a validated self-reported questionnaire used to assess quality of life (QOL) related to gastrointestinal function in patients with SSc (Khanna D., et al., Arthritis Rheum. 2009, 61:1257-63). It employs a 7-multi-item scale with areas of reflux, distention/bloating, diarrhea, fecal soilage, constipation, emotional well-being, and social functioning.

In some embodiments, reducing pain is measured by change in tender joint count 28 (TJC28) at about 24 weeks after initial administration of the bispecific antibody. The TJC28 is an assessment of the overall joint pain based upon the examination of 28 key joints. It is a reliable and validated method of assessing general joint pain. The 28 joints that are part of the assessments include: shoulders (2 joints), elbows (2 joints), wrists (2 joints), metacarpophalangeals (10 joints), proximal interphalangeals (10 joints), and knees (2 joints).

In some embodiments, reducing digital ulcers is measured by the number of digital ulcers at about any of 4, 8, 12, 24, 36, 48 or greater than 48 weeks after initial administration of the bispecific antibody. In some embodiments, reducing digital ulcers is measured by the number of digital ulcers at about 24 48 weeks after initial administration of the bispecific antibody. The digital ulcer count captures the number of active open sores (or digital ulcers) on fingertips secondary to SSc (and not secondary to localized trauma or injury). In some embodiments, cracks, fissures, or even skin breakdown related to calcinosis are not included.

In some embodiments, the invention provides methods for improving a composite response index for diffuse cutaneous systemic sclerosis (CRISS) in a human subject with SSc, the method comprising administering an effective amount of an anti-IL4/anti-IL13 bispecific antibody to said subject; wherein the improvement in CRISS is improved at about any of 4, 8, 12, 24, 36, 48 or greater than 48 weeks after initial administration of the bispecific antibody compared to baseline. In some embodiments, the improvement in CRISS is improved at about 24 weeks after initial administration of the bispecific antibody compared to baseline. The CRISS tool summarizes the changes in the clinical and patient-reported outcomes using a single composite score that reflects the probability that the patient with dcSSc has improved (Khanna D., et al., *Arthritis Care Res.* (Hoboken) 2016, 68(2):167-78). For an effective therapeutic agent of dcSSc, CRISS is able to summarize the higher probability of improvement in a subject treated with and anti-IL4/anti-IL13 bispecific antibody (e.g., RKB) versus an ineffective agent or background. CRISS is a 2-step process as described below Step 1: Patients who develope new or worsening of cardiopulmonary and/or renal involvement due to SSc are considered as not improved (irrespective of improvement in other core items) and assigned a probability of improving equal to 0.0. Specifically if a subject develops any of the following: new scleroderma renal crisis; decline in FVC % predicted≥15% (relative), confirmed by another FVC % within a month, high resolution computer tomography (HRCT) to confirm ILD (if previous HRCT of chest did not show ILD) and FVC % predicted below 80% predicted; new onset of left ventricular failure (defined as left ventricular ejection fraction≤45%) requiring treatment; or new onset of PAH on right heart catheterization requiring treatment (attributable to SSc) (PAH is defined as mean pulmonary artery pressure≥25 mm Hg at rest and an end-expiratory pulmonary artery wedge pressure≤15 mm Hg and a pulmonary vascular resistance>3 Wood units).

Step 2: For the remaining patients, Step 2 involves computing the predicted probability of improving for each subject using the following equation (equation derived predicted probabilities from a logistic regression model):

$$\frac{\exp(-5.54 - 0.81 * \Delta MRSS + 0.21 * \Delta FCV\% - 0.40 * \Delta Pt-glob - 0.44 * \Delta MD-glob - 3.41 * \Delta HAQ-DI)}{1 + \exp(-5.54 - 0.81 * \Delta MRSS + 0.21 * \Delta FVC\% - 0.40 * \Delta Pt-glob - 0.44 * \Delta MD-glob - 3.41 * \Delta HAQ-DI)}$$

wherein $\Delta$mRSS indicates the change in mRSS from baseline, $\Delta$FVC denotes the change in FVC % predicted from baseline, $\Delta$Pt-glob indicates the change in patient global assessment, $\Delta$MD-glob denotes the change in physician global assessment, and $\Delta$HAQ-DI is the change in HAQ-DI. All changes are absolute change (Time$_2$−Time$_{baseline}$).

Patient and physician global assessments of overall health are used in the Step 2 calculation of CRISS. These two assessments are based upon a Likert scale ranging from 0 (Excellent) to 10 (Extremely Poor) (Khanna D., et al., *Arthritis Care Res.* 2016, 68(2):167-78).

In some embodiments, the invention provides methods for improving a composite response index for European Quality of Life-5 Dimension-5 Level (EQ-5D-5L) index in a human subject with SSc, the method comprising administering an effective amount of an anti-IL4/anti-IL13 bispecific antibody to said subject; wherein the improvement in EQ-5D-5L is improved at about any of 4, 8, 12, 24, 36, 48 or greater than 48 weeks after initial administration of the bispecific antibody compared to baseline. In some embodiments, the improvement in EQ-5D-5L is improved at about 24 weeks after initial administration of the bispecific antibody compared to baseline. The EQ-5D-5L questionnaire is a standardized measure of health status developed by the EuroQol Group in order to provide a simple, generic measure of health for clinical and economic appraisal. The EQ-5D-5L is designed for self-completion by patients.

The EQ-5D comprises 2 discrete scales: the EQ-5D descriptive system and the EQ VAS. The EQ-5D descriptive system has 5 items, each measuring one dimension of health: mobility, self-care, usual activities, pain/discomfort and anxiety/depression. Each dimension/item has a 5 level Likert-type response scale: no problems, slight problems, moderate problems, severe problems, and extreme problems. Responses for the 5 dimensions can be combined in a single 5-digit number describing the respondent's health profile and can be converted into a single index value for the calculation of quality-adjusted life years (QALYs) to inform economic evaluations of health care interventions. The EQ VAS provides a quantitative measure of health as judged by the individual respondents on a vertical visual analogue scale. The EQ VAS 'thermometer' has endpoints of 100 ("The best health you can imagine") at the top and 0 ("The worst health you can imagine") at the bottom.

Intracellular signaling after ligation of IL-4 and IL-13 with their cell surface receptors is mediated in part by phosphorylation of the signaling molecule signal transducer and activator of transcription 6 (Stat6).

Chemokine (C-C motif) ligand 17 (CCL17) is a small cytokine belonging to the CC chemokine family. CCL17 is also known as thymus and activation regulated chemokine (TARC). TARC is induced by IL-4 and/or IL-13 through State phosphorylation (Wirnsberger et al., (2006) *Eur J Immunol.* 36: 1882-91; Liddiard et al., (2006) *BMC Mol Biol.* 29: 7:45; Monick et al., (2007) *J Immunol.* 179:1648-58) Thus, inhibition of IL-4 and/or IL-13-mediated signaling by, for example, IL-4/IL-13-binding antibody-like proteins, is correlated with inhibition of TARC inducement. In some embodiments, the methods disclosed herein comprise methods of detecting the binding to IL-4 and/or IL-13 of an antibody or antibodylike binding protein or fragment thereof that has been administered to a subject, the methods comprising (a) administering the antibody or antibody-like binding protein of fragment thereof to the subject; and (b) determining the amount of CCL17/TARC within a blood, serum, or plasma sample drawn from the subject, wherein a decrease in the amount of CCL17/TARC in the sample relative to a sample drawn from the subject prior to administration of the antibody or antibodylike binding protein or fragment thereof signifies binding of the antibody or antibody-like binding protein or fragment thereof to IL-4 and/or IL-13. In some embodiments, the subject is a human subject. In some embodiments, the antibody or antibody-like binding protein or fragment thereof is a dual-V-region antibody-like binding protein or fragment thereof. In some embodiments, the dual-V-region antibody-like binding protein or fragment thereof is specific for IL-4 or IL-13, or bispecific for IL-4 and IL-13. In some embodiments, step (c) further comprises increasing the dose if the decrease in TARC/CCL17 measured in step (b) is below a threshold value (i.e. if TARC/CCL17 levels do not decrease enough), or decreasing the dose if the decrease in TARC/CCL17 measured in step (b) is above a threshold value (i.e. if TARC/CCL17 decreases too much). In some embodiments, the threshold value of step (c) is about a 10% decrease, or about a 15% decrease, or about a 20% decrease, or about a 25% decrease, or about a 30% decrease, or about a 35% decrease, or about a 40% decrease, or about a 45% decrease, or about a 50% decrease, or about a 55% decrease, or about a 60% decrease, or about a 65% decrease in the amount of TARC/CCL17 relative to the amount of TARC/CCL17 in the subject measured before the dose was administered. In some embodiments, the threshold value is about a 20% to about a 60% decrease, or about a 40% to about a 50% decrease in the amount of TARC/CCL17 relative to the amount of TARC/CCL17 in the subject measured before the dose was administered. In some embodiments, the threshold value is about a 43% decrease in the amount of TARC/CCL17 relative to the amount of TARC/CCL17 in the subject measured before the dose was administered. For example, a 43% decrease for a 200 mg dose signifies binding of a 200 mg dose of bispecific anti-IL-4/IL-13 dual-V-region antibody-like binding protein to IL-4/IL-13.

In some embodiments, protein biomarkers associated with the activity of the disease (cartilage oligomeric matrix protein [COMP], chemokine C-C motif ligand 2 [CCL2]) and the IL-4/IL-13 pathway (TARC, periostin, and eotaxin-3) are measured to monitor treatment. In some embodiments, the presence of anti-drug antibodies (ADA) are used to monitor treatment.

In certain embodiments, the formulations of the invention can be administered in combination with one or more therapies (e.g., therapies that are not the formulations of the invention that are currently administered to prevent, treat, manage, and/or ameliorate an IL-4 and/or IL-13-mediated disease (e.g., SSc). The use of the term "in combination" does not restrict the order in which therapies are administered to a subject. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject that had, has, or is susceptible to an IL-4 and/or IL-13-mediated disease (e.g., SSc). In some embodiments, the anti-IL-4/anti-IL13 antibody is administered in combination with a therapy used for the treatment of SSc. In some embodiments, the anti-IL-4/anti-IL13 antibody is administered in combination with pirfenidone or nintedanib. Any additional therapy can be administered in any order with the other additional therapies. Non-limiting examples of therapies that can be administered in combination with an antibody of the invention include approved anti-inflammatory agents listed in the U.S. Pharmacopoeia and/or Physician's Desk Reference.

Exemplary Embodiments

1. A method for treating systemic sclerosis (SSc) in a human subject with SSc, the methods comprising administering about 200 mg of a dual-V-region bispecific antibody or antigen-binding fragment that specifically binds IL-4 and IL-13 subcutaneously to the subject.

2. The method of embodiment 1, wherein 200 mg of the bispecific antibody is administered to the subject about once per week or about every 5 to 9 days.

3. The method of embodiment 1 or 2, wherein the treatment is given for at least about 24 weeks.

4. The method of any one of embodiments 1-3, wherein the bispecific antibody is in a pharmaceutical formulation.

5. The method of embodiment 4, wherein the pharmaceutical formulation comprises about 100 mg/ml bispecific antibody, about 6.3 mM monobasic sodium phosphate, about 37 mM Tris, about 5% (w/v) sucrose, about 3% (w/v) proline, and about 0.2% (w/v) polysorbate 80, wherein the pH of the formulation is about 7.0.

6. The method of embodiment 5, wherein the formulation is reconstituted from a lyophilized formulation.

7. The method of any one of embodiments 1-6, wherein the bispecific antibody is administered in combination with another agent.

8. The method of embodiment 7, wherein the another agent is administered before, simultaneous with, or after administration of the bispecific antibody.

9. The method of any one of embodiments 1-8, wherein the systemic sclerosis is diffuse cutaneous systemic sclerosis.

10. The method of any one of embodiments 1-9, wherein the bispecific antibody or bispecific antibody fragment thereof comprises a light chain polypeptide comprising a light chain variable domain $VL_{hB\text{-}B13}$ and a light chain variable domain $VL_{hBD4\text{-}8}$, and a heavy chain polypeptide comprising a heavy chain variable domain $VH_{hB\text{-}B13}$ and a heavy chain variable domain $VH_{hBD4\text{-}8}$, wherein:

$VL_{hB\text{-}B13}$ comprises the three CDRs comprising the amino acid sequences

```
                                    (SEQ ID NO: 8)
         RASESVDSYGQSYMH, (SEQ ID NO: 9)
         LASNLES,
         and (SEQ ID NO: 10)
         QQNAEDSRT;
```

$VL_{hBD4\text{-}8}$ comprises the three CDRs comprising the amino acid sequences

```
                                    (SEQ ID NO: 14)
         HASQNIDVWLS, (SEQ ID NO: 15)
         KASNLHTG,
         and (SEQ ID NO: 16)
         QQAHSYPFT,
```

$VH_{hB\text{-}B13}$ comprises the three CDRs comprising the amino acid sequences

```
                                    (SEQ ID NO: 11)
         GFSLTDSSIN, (SEQ ID NO: 12)
         DGRID,
``` and

```
                                             (SEQ ID NO: 13)
DGYFPYAMDF,
```

VH$_{hBD4\text{-}8}$ comprises the three CDRs comprising the amino acid sequences

```
                                             (SEQ ID NO: 17)
GYSFTSYWIH, (SEQ ID NO: 18)
IDPSDGETR
and (SEQ ID NO: 19)
LKEYGNYDSFYFDV.
```

11. The method of embodiment 10, wherein:
VL$_{hB\text{-}B13}$ comprises an amino acid sequence at least 95% identical to the amino acid sequence of SEQ ID NO:1,
VL$_{hBD4\text{-}8}$ comprises an amino acid sequence at least 95% identical to the amino acid sequence of SEQ ID NO:3,
VH$_{hB\text{-}B13}$ comprises an amino acid sequence at least 95% identical to the amino acid sequence of SEQ ID NO:2,
VH$_{hBD4\text{-}8}$ comprises an amino acid sequence at least 95% identical to the amino acid sequence of SEQ ID NO:4.

12. The method of embodiment 10 or 11, wherein:
VL$_{hB\text{-}B13}$ comprises the amino acid sequence of SEQ ID NO:1,
VL$_{hBD4\text{-}8}$ comprises the amino acid sequence of SEQ ID NO:3,
VH$_{hB\text{-}B13}$ comprises the amino acid sequence of SEQ ID NO:2,
VH$_{hBD4\text{-}8}$ comprises the amino acid sequence of SEQ ID NO:4.

13. The method of any one of embodiments 9-11, wherein the light chain polypeptide comprises the structure N-VL$_{hB\text{-}B13}$-linker-VL$_{hBD4\text{-}8}$-CL-C and the heavy chain polypeptide comprises the structure N-VH$_{hB\text{-}B13}$-linker-VH$_{hBD4\text{-}8}$-CH1-C.

14. The method of any one of embodiments 10-13, wherein the light chains comprise the structure N-VL$_{hB\text{-}B13}$-linker-VL$_{hBD4\text{-}8}$-CL-C and the heavy chains comprise the structure N-VH$_{hB\text{-}B13}$-linker-VH$_{hBD4\text{-}8}$-CH1-CH2-CH3-C.

15. The method of embodiment 13 or 14, wherein the linker comprises the amino acid sequence of SEQ ID NO:6.

16. The method of any one of embodiments 10-15, wherein the bispecific antibody or bispecific antibody fragment thereof comprises two identical light chain polypeptides and two identical heavy chain polypeptides.

17. The method of any one of embodiments 10-16, wherein the light chain polypeptide comprises an amino acid sequence having at least about 90% identity to the amino acid sequence of SEQ ID NO:22 and the heavy chain polypeptide comprises an amino acid sequence having at least about 90% identity to the amino acid sequence of SEQ ID NO:23.

18. The method of any one of embodiments 10-17, wherein the light chain polypeptide comprises the amino acid sequence of SEQ ID NO:22 and the heavy chain polypeptide comprises the amino acid sequence of SEQ ID NO:23.

19. A method of reducing sclerotic plaques in a human subject with SSc, the method comprising administering an effective amount of an anti-IL4/anti-IL13 bispecific antibody to said subject; wherein the sclerotic plaques are reduced by at least about 20%, 40%, 60%, 80% or 100% at about 24 weeks after initial administration of the bispecific antibody compared to baseline.

20. The method of embodiment 19 wherein a portion of the treated human subjects with SSC have an improved modified Rodnan Skin Score (mRSS) of at least about 20%, 40%, and 60% at about 24 weeks after initial administration of the bispecific antibody compared to baseline.

21. The method of embodiment 20, wherein the improved mRSS is measured as the least square mean change from baseline.

22. The method of embodiment 20 or 21, wherein the least square mean change from baseline is more than about any of −3.00, −3.5, −4.0, −4.5, −5.0, −5.5, or −6.0.

23. The method of any one of embodiments 19-22, wherein the anti-IL4/anti-IL13 antibody is RKB.

24. The method of any one of embodiments 19-23, wherein about 200 mg of the anti-IL4/anti-IL13 antibody is administered subcutaneously to the subject.

25. The method of embodiment 24, wherein 200 mg of the bispecific antibody is administered to the subject about once per week or about every 5 to 9 days.

26. The method of embodiment 24 or 25, wherein the treatment is given for at least about 24 weeks.

27. The method of any one of embodiments 19-26, wherein the bispecific antibody is in a pharmaceutical formulation.

28. The method of embodiments 27, wherein the pharmaceutical formulation comprises about 100 mg/ml bispecific antibody, about 6.3 mM monobasic sodium phosphate, about 37 mM Tris, about 5% (w/v) sucrose, about 3% (w/v) proline, and about 0.2% (w/v) polysorbate 80, wherein the pH of the formulation is about 7.0.

29. The method of embodiment 27, wherein the formulation is reconstituted from a lyophilized formulation.

30. The method of any one of embodiments 19-29, wherein the bispecific antibody is administered in combination with another agent.

31. The method of embodiment 30, wherein the another agent is administered before, simultaneous with, or after administration of the bispecific antibody.

32. The method of any one of embodiments 19-31, wherein the systemic sclerosis is diffuse cutaneous systemic sclerosis.

33. The method of any one of embodiments 19-32, wherein the bispecific antibody or bispecific antibody fragment thereof comprises a light chain polypeptide comprising a light chain variable domain VL$_{hB\text{-}B13}$ and a light chain variable domain VL$_{hBD4\text{-}8}$, and a heavy chain polypeptide comprising a heavy chain variable domain VH$_{hB\text{-}B13}$ and a heavy chain variable domain VH$_{hBD4\text{-}8}$, wherein:

VL$_{hB\text{-}B13}$ comprises the three CDRs comprising the amino acid sequences

```
                                             (SEQ ID NO: 8)
RASESVDSYGQSYMH, (SEQ ID NO: 9)
LASNLES,
and (SEQ ID NO: 10)
QQNAEDSRT;
```

VL$_{hBD4-8}$ comprises the three CDRs comprising the amino acid sequences

HASQNIDVWLS, (SEQ ID NO: 14)

KASNLHTG, (SEQ ID NO: 15)
and

QQAHSYPFT, (SEQ ID NO: 16)

VH$_{hB-B13}$ comprises the three CDRs comprising the amino acid sequences

GFSLTDSSIN, (SEQ ID NO: 11)

DGRID, (SEQ ID NO: 12)
and

DGYFPYAMDF, (SEQ ID NO: 13)

VH$_{hBD4-8}$ comprises the three CDRs comprising the amino acid sequences

GYSFTSYWIH, (SEQ ID NO: 17)

IDPSDGETR (SEQ ID NO: 18)
and

LKEYGNYDSFYFDV. (SEQ ID NO: 19)

34. The method of embodiment 33, wherein:
VL$_{hB-B13}$ comprises an amino acid sequence at least 95% identical to the amino acid sequence of SEQ ID NO:1,
VL$_{hBD4-8}$ comprises an amino acid sequence at least 95% identical to the amino acid sequence of SEQ ID NO:3,
VH$_{hB-B13}$ comprises an amino acid sequence at least 95% identical to the amino acid sequence of SEQ ID NO:2,
VH$_{hBD4-8}$ comprises an amino acid sequence at least 95% identical to the amino acid sequence of SEQ ID NO:4.

35. The method of embodiment 32 or 33, wherein:
VL$_{hB-B13}$ comprises the amino acid sequence of SEQ ID NO:1,
VL$_{hBD4-8}$ comprises the amino acid sequence of SEQ ID NO:3,
VH$_{hB-B13}$ comprises the amino acid sequence of SEQ ID NO:2,
VH$_{hBD4-8}$ comprises the amino acid sequence of SEQ ID NO:4.

36. The method of any one of embodiments 33-35, wherein the light chain polypeptide comprises the structure N-VL$_{hB-B13}$-linker-VL$_{hBD4-8}$-CL-C and the heavy chain polypeptide comprises the structure N-VH$_{hB-B13}$-linker-VH$_{hBD4-8}$-CH1-C.

37. The method of any one of embodiments 33-36, wherein the light chains comprise the structure N-VL$_{hB-B13}$-linker-VL$_{hBD4-8}$-CL-C and the heavy chains comprise the structure N-VH$_{hB-B13}$-linker-VH$_{hBD4-8}$-CH1-CH2-CH3-C.

38. The method of embodiment 36 or 37, wherein the linker comprises the amino acid sequence of SEQ ID NO:6.

39. The method of any one of embodiments 33-38, wherein the bispecific antibody or bispecific antibody fragment thereof comprises two identical light chain polypeptides and two identical heavy chain polypeptides.

40. The method of any one of embodiments 33-39, wherein the light chain polypeptide comprises an amino acid sequence having at least about 90% identity to the amino acid sequence of SEQ ID NO:22 and the heavy chain polypeptide comprises an amino acid sequence having at least about 90% identity to the amino acid sequence of SEQ ID NO:23.

41. The method of any one of embodiments 33-40, wherein the light chain polypeptide comprises the amino acid sequence of SEQ ID NO:22 and the heavy chain polypeptide comprises the amino acid sequence of SEQ ID NO:23.

Examples

The Examples that follow are illustrative of specific embodiments of the disclosure, and various uses thereof. They are set forth for explanatory purposes only, and should not be construed as limiting the scope of the invention in any way.

Example 1: Efficacy and Safety of a Humanized Anti-IL-4/IL-13 Bispecific Antibody, RKB, in the Treatment of Subjects with Diffuse Systemic Sclerosis RKB was evaluated in a Phase 2 study (NCT02921971), in comparison with placebo, for efficacy on skin fibrosis of subjects with diffuse systemic sclerosis (dcSSc) when administered subcutaneously for 24 weeks of treatment.

Methods

A multinational, randomized, double-blind, placebo-controlled, 2 parallel groups, proof of concept Phase 2 study investigated the efficacy and safety of RKB 200 mg administered subcutaneously once a week over a 24 week period to subjects with diffuse SSc. Approximately 94 patients were randomized 1:1 to the following two treatment groups: 1) RKB group (N=47), which received 200 mg weekly subcutaneous administrations of RKB; and 2) placebo group (N=47), which received weekly subcutaneous administrations of placebo. Randomization was stratified based upon the patients' medical history of SSc interstitial lung disease (SSc-ILD; yes or no). The study design is indicated in FIG. 2.

Study Population

Figure 2:
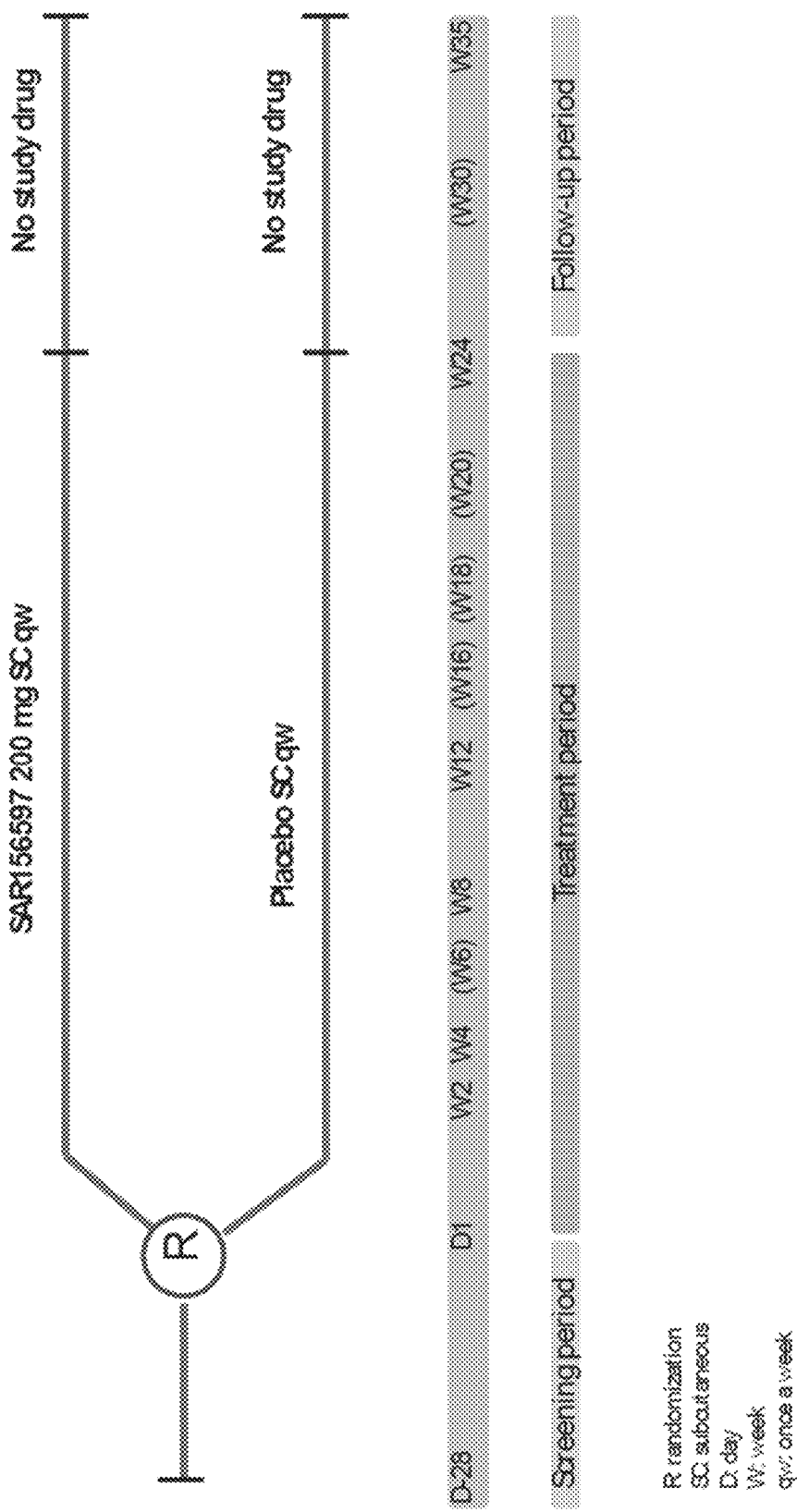
FIG. 2 is a diagram of a clinical trial study in patients with systemic sclerosis. Patients were randomized (R) into a treatment arm (top) receiving weekly subcutaneous injections of Romilkimab (RKB; also known as SAR156597) at 200 mg for 24 weeks or a placebo arm (bottom) receiving weekly subcutaneous injections of placebo for 24 weeks. A screening period before and a follow-up period after the treatment period are included. Visits occur during the screening period, at D1 (Day 1), W2 (Week 2), W4, W8, W12, W24, and W35. Phone calls (indicated by parentheses) occur at W6, W16, W18, and W30.

Prior to randomization into cohorts, subjects were screened to assess their eligibility to enter the study within 28 days before Day 1 (D-28, FIG. 2).

Inclusion criteria for eligible subjects were: systemic sclerosis according to the ACR/EULAR 2013 criteria (van den Hoogen F., et al., *Ann. Rheum. Dis.* 2013, 72(11):1747-55); and diffuse cutaneous form of SSc according to Leroy's criteria Exclusion criteria included: age<18 years of age; disease duration of >36 months from time of first non-Raynaud's phenomenon manifestation; a modified Rodnan skin score (mRSS)<10 or >35 at screening and baseline visits; history of vasculitis (active or in remission); diagnosis of connective tissue disease (other than SSc) or overlap syndrome (e.g., polymyositis/SSc); positive human immunodeficiency virus (HIV) serology or a known history of HIV infection (active or in remission); abnormal hepatitis B and/or hepatitis C tests indicative of active or chronic infection; positive or two confirmed indeterminate QuantiFERON-TB Gold tests at screening (reglardless of prior treatment status); serious infection (e.g., pneumonia, pyelonephritis) within 4 weeks of screening, infection requiring hospitalization or intravenous antibiotics within 4 weeks of screening, or chronic bacterial infection (e.g., osteomyelitis); history of anaphylaxis to any biologic therapy; evidence of any clinically significant, severe, or unstable, acute, or chronically progressive, uncontrolled infection or medical condition (e.g., cerebral, cardiac, pulmonary, renal, hepatic, gastrointestinal, or neurologic other than SSc or SSc-ILD) or previous, active, or pending surgical disorder, or any condition that may affect patient safety in the judgment of the investigator; at screening, the % predicted force vital capacity (FVC) is ≤75% and % predicted carbon monoxide diffusing lung capacity (DLCO) after hemoglobin correction is ≤40%; history of heart failure (including acutely decompensated in the setting of preserved ejection fraction), left ventricular ejection fraction (LVEF)≤45%, coronary artery disease, angina, myocardial infarction, ischemic cardiomyopathy, and/or hypertrophic cardiomyopathy; any prior history of malignancy or active malignancy, including lymphoproliferative diseases (except successfully-treated carcinoma in-situ of the cervix, non-metastatic squamous cell or basal cell carcinoma of the skin) within 5 years prior to baseline; ischemic ECG changes (except those not supported by the findings of a left heart catheterization performed in the last year within screening) and/or other clinically significant ECG findings at screening (including, but not limited to, second-degree heart block, third-degree heart block, QT prolongation (symptomatic), sick sinus syndrome, left bundle branch block (complete), right bundle branch block (complete), atrial fibrillation (uncontrolled), atrial flutter (uncontrolled), Wolff-Parkinson-White syndrome, atrioventricular nodal reentry tachycardia, and ventricular arrhythmias including ventricular tachycardia, ventricular fibrillation, Torsades de Pointes, and bradyarrhythmias); high dose steroids (>10 mg/day prednisone or equivalent), or a change in steroid dose within 4 weeks prior to randomization (or baseline visit), or expected changes during the course of the study; previous treatment with rutixumab within 12 months prior to screening; previous treatment with bone marrow transplantation, total lymphoid irradiation, or ablative ultra-high dose cyclophosphamide; treatment with high dose immunosuppressive drug (e.g., cyclophosphamide>1 mg/kg oral/day or >750 mg IV/month; azathioprine>100 mg/day; methotrexate>15 mg/week; mycophenolate mofetil>2 g/day) within three months of screening or a change in dose within 4 weeks prior to randomization (or baseline visit), or expected changes in dose during the course of the study; treatment with etanercept, cyclosporine A, intravenous immunoglobulin (IVIG), rapamycin, D-penicillamine, tyrosine kinase inhibitors within 4 weeks of screening, or antithymocyte globulin within 6 months of screening; treatment with infliximab, certolizumab, golimumab, abatacept, or adalimumab, tocilizumab within 8 weeks or screening, or anakinra within 1 week of screening; treatment with any investigational drug within one month of screening, or 5 half-lives, if known (whichever is longer); abnormal laboratory test(s) at screening from any of alanine transaminase (ALT) or aspartate transaminase (AST)>2 times upper limit of normal range (ULN), hemoglobin<11 g/100 mL for male and <10 g/100 mL for female, neutrophils<1500/mm$^3$ (except<1000/mm$^3$ for those of African descent), platelets<100,000/mm$^3$, creative≥150 µmol/L; current history of substance and/or alcohol abuse; pregnant or breastfeeding woman; and women who are of childbearing potential not protected by highly-effective contraceptive method(s) of birth control and/or are unwilling or unable to be tested for pregnancy.

Dosage Regimen

After the screening period, on Day 1 (D1, FIG. 2), each eligible subject was randomly assigned to receive one of the following two arms: (1) 200 mg of RKB administered subcutaneously once every week (qw); and (2) placebo administered subcutaneously once every week (qw) (FIG. 2). Treatment with RKB or placebo was initiated on D1 and the duration of treatment was 24 weeks. The study comprised 8 on-site visits and 5 phone calls. Visit 1 for screening was between D-28 and D-1; Visit 2 for baseline measurements was at D1 where a first dose was received by the subject; visits 3-6 were at Week 2, Week 4, Week 8, and Week 12 of the treatment period; Visit 7 was during the last week of dosing (Week 24); and Visit 8 was an end of study visit for follow-up at Week 35. During on-site visits, RKB or placebo was administered after clinical procedures and blood collection. For safety considerations, phone calls to subjects were made at Weeks 6, 16, 18, and 20 during the treatment period and at Week 30 during the follow-up period. A follow-up period after dosing (FIG. 2) was implemented to assess for adverse events (AEs) and pharmacokinetic analysis.

Pharamacokinetic parameters are estimated using the population PK approach for $C_{trough}$.

Formulation and Route of Administration

RKB solution for injection at 100 mg/mL is prepared from RKB supplied as a sterile freeze-dried powder in a glass vial. Each vial was filled with 125 mg of RKB freeze-dried powder, and the final solution for injection is obtained by reconstitution of the entire vial content with 1.1 mL of sterile water for injection, leading to an amount of 125 mg of RKB drug substance in a total volume of 1.25 mL equating to a concentration of 100 mg/mL of RKB solution. One mL of this 100 mg/mL RKB solution was then withdrawn for dose administration. Two drug product vials are thus needed to reach the 200 mg dose and to prepare a 2 mL RKB solution syringe.

For placebo preparations, vials containing excipients were reconstituted with 1.1 mL of sterile water resulting in a total volume of 1.25 mL. Two placebo product vials were required with 1 mL taken from each vial to prepare a 2 mL placebo solution syringe.

The route of administration was subcutaneous in the abdomen. Subcutaneous injection sites were alternated between the four quadrants of the abdomen (avoiding navel and waist areas) so that the same site was not injected for two consecutive weeks. The sites were preferably free of SSc involvement.

RKB or placebo was administered every 7 days±2 days from the initial administration. This window was permitted per protocol to accommodate various circumstances (e.g., pending laboratory results, management of adverse events, visit scheduling difficulty).

Efficacy Endpoints

The primary efficacy endpoint to evaluate efficacy of RKB on skin fibrosis of patients with dcSSC was by assessing change in modified Rodnan Skin Score (mRSS) from baseline to Week 24. Two secondary endpoints to evaluate the efficacy of RKB on other aspects of dcSSc were: 1) change in HAQ-DI, assessed with SHAQ, from baseline to Week 24; and 2) change in respiratory function as measured by observed FVC and observed DLco (corrected for hemoglobin) from baseline to Week 24. Exploratory endpoints will include: change in visual analogue scale (VAS) for pain, breathing function, vascular function (Raynaud's phenomenon), gastrointestinal function, digital ulcers, and global assessment from SHAQ from baseline to Week 24; change in respiratory function as measured by % predicted FVC and % predicted DLco (corrected for hemoglobin) from baseline to Week 24; change in UCLA Scleroderma Clinical Trial Consortium Gastrointestinal Tract 2.0 (UCLA SCTC GIT 2.0) score from baseline to Week 24; change in TJC28 from baseline to Week 24; change in digital ulcer count from baseline to Week 24; CRISS from baseline to Week 24; change in EQ-5D-5L index from baseline to Week 24; change in efficacy endpoints (mRSS, HAQ-DI, VAS from SHAQ, observed FVC, % predicted FVC, observed DLco [corrected for hemoglobin], % predicted DLco [corrected for hemoglobin], UCLA SCTC GIT 2.0, TJC28, digital ulcer count, CRISS, and EQ-5D-5L) from baseline to Week 35 (up to end of follow-up period) and proportion of patients with improvement in mRSS of at least 20%, 40%, and 60% from baseline to Week 35; and proportion of patients with improvement in SHAQ (HAS-DI and VAS) and EQ-5D-5L (index value and VAS) based upon MIC at Week 24.

Modified Rodnan Skin Score

The fibrosis of the skin was assessed using the mRSS which is conducted by palpation of the skin in 17 areas of the body (fingers, hands, forearms, arms, feet, legs and thighs, face, chest and abdomen) using a 0-3 scale, where 0=normal, 1=mild thickness, 2=moderate thickness and 3=severe thickness. Total skin score can range from 0 (no thickening) to 51 (severe thickening in all 17 areas). Only those physicians or qualified medical personnel who have undergone a standardized training were permitted to evaluate the skin thickening. Efforts were undertaken for the same medical personnel to evaluate a given patient from baseline to EOS participation in order to minimize any inter-rater variability. The baseline and Week 24/Visit 7 mRSS assessment must be conducted by the same medical personnel.

Respiratory Function

The pulmonary function test is a secondary endpoint that will assess the change in respiratory function as measured by observed FVC and observed DLco (corrected for hemoglobin) from baseline to Week 24. The absolute change in observed and % predicted change in FVC and DLco from baseline to Week 24 and/or Week 35 was assessed as exploratory endpoints. The manual correction of DLco for hemoglobin was based upon the following equation unless it was automatically corrected during measurement: 1) For male patients: $DLco_{observed/(factor)}$, where factor is $=(1.7\times Hb)/(10.22+Hb)$; 2) For female patients: $DLco_{observed/(factor)}$, where factor is $=(1.7\times Hb)/(9.38+Hb)$. Hb refers to hemoglobin, and the value was taken from the same visit where the DLco was conducted. The spirometry was performed in compliance with the 2005 ATS/ERS guideline (Miller M. R., et al., *Eur. Respir. J.* 2005, 26:319-38) while the DLco was performed in compliance with standard guidance (MacIntyre N., et al., *Eur. Respir.* 1 2005, 26:720-35).

Gastrointestinal Manifestations

The UCLA SCTC GIT 2.0 instrument is a validated self-reported questionnaire used to assess quality of life (QOL) related to gastrointestinal function in patients with SSc (Khanna D., et al., *Arthritis Rheum.* 2009, 61:1257-63). It employs a 7-multi-item scale with areas of reflux, distention/bloating, diarrhea, fecal soilage, constipation, emotional well-being, and social functioning. This was captured at all visits except Visit 1 and Visit 3.

Renal Function

Renal function was assessed through the measurement of blood urea nitrogen, creatinine and urinalysis (dipstick) at all visits except V3. The urinalysis (dipstick) captured specific gravity, pH, glucose, ketones, blood, protein, nitrate, leukocyte esterase, urobilinogen and bilirubin. If any parameter on the dipstick was abnormal, a urine sample was sent to the central laboratory for testing. If the dipstick was positive for protein and/or red blood cells, microscopic analysis was performed by the central laboratory.

Cardiac Manifestations

Systemic sclerosis associated with cardiac manifestations was assessed by physical examination and ECG which is an established method of monitoring for cardiac conduction and potential coronary and myocardial diseases. Electrocardiogram was captured at all scheduled visits except Visit 3. Cardiovascular events are reported as adverse events.

Joint Pain Assessment

The TJC28 is an assessment of the overall joint pain based upon the examination of 28 key joints. It is a reliable and validated method of assessing general joint pain and was captured at all visits except Visit 1 and Visit 3. The 28 joints that are part of the assessments include: shoulders (2 joints), elbows (2 joints), wrists (2 joints), metacarpophalangeals (10 joints), proximal interphalangeals (10 joints), and knees (2 joints).

Digital Ulcer Count

The digital ulcer count captures the number of active open sores (or digital ulcers) on fingertips secondary to SSc (and not secondary to localized trauma or injury). Cracks, fissures, or even skin breakdown related to calcinosis were not included. The digital ulcer count was conducted at all visits except Visit 1 and Visit 3.

Scleroderma Health Assessment Questionnaire

The SHAQ, which includes the standard HAQ-DI to measure the functional disability and 5 SSc-specific VAS assessments was completed by patients at baseline and throughout the study, except Visit 1 and Visit 3 (Steen V. D. and Medsger T. A., *Arthritis Rheum.* 1997, 40:1984-91). The SHAQ is the standard, validated, and accepted health assessment questionnaire in patients with SSc to assess the physical/functional disability related to skin and systemic fibrosis.

The HAQ DI contains 8 domains of activity (dressing, arising, eating, walking, hygiene, reach, grip, and common daily activities) each of which has at least 2 questions, for a total of 20 items. For each item, patients report the amount of difficulty experienced performing the activity. There are 4 possible responses for each item ranging from 0 (without any difficulty) to 3 (unable to do). For each of the 8 domains included in the HAQ-DI, the score is the single response within the domain with the highest score. If aids or devices are used, and if the highest score is 0 or 1, then the score is raised to 2; if the highest score is 2 or 3, the score is kept as it is. The HAQ-DI composite score is then calculated as the average of the scores of the 8 domains. If 1 or 2 of the domains are missing, the HAQ-DI composite score is obtained by dividing the sum of the domains by the number of answered domains. If three or more of the domains are missing, then the HAQ-DI composite score is missing. The composite score is reported, falling between 0 and 3 on an ordinal scale. The scores are interpreted as 0 (no impairment in function) to 3 (maximal impairment of function).

The HAQ-DI also contains a VAS that patients use to report the amount of pain experienced in the past week. The VAS is a 10-cm line that is converted to a continuous scale from 0 to 3 where 1 cm is equivalent to 0.3 points. The anchors of the VAS are 0 (no pain) to 100 (very severe pain). To obtain the patient score, a metric ruler was used to measure the distance in centimeters from the left anchor to the patient's mark, and then multiplied by 0.3. The VAS pain score is not incorporated into the HAQ DI composite score.

For the other 5 VAS, the patients rated breathing, vascular (Raynaud's phenomenon), gastrointestinal function, digital ulcers, and global assessment. They were asked to make a mark on a 10 cm line to indicate the severity from 0-100 where 0 indicates no severity and 100 indicates the worst severity.

Euro-QOL-5D-5L

The EQ-5D-5L questionnaire is a standardized measure of health status developed by the EuroQol Group in order to provide a simple, generic measure of health for clinical and economic appraisal. The EQ-5D-5L is designed for self-completion by patients.

The EQ-5D comprises 2 discrete scales: the EQ-5D descriptive system and the EQ VAS. The EQ-5D descriptive system has 5 items, each measuring one dimension of health: mobility, self-care, usual activities, pain/discomfort and anxiety/depression. Each dimension/item has a 5 level Likert-type response scale: no problems, slight problems, moderate problems, severe problems, and extreme problems. Responses for the 5 dimensions can be combined in a single 5-digit number describing the respondent's health profile and can be converted into a single index value for the calculation of quality-adjusted life years (QALYs) to inform economic evaluations of health care interventions. The EQ VAS provides a quantitative measure of health as judged by the individual respondents on a vertical visual analogue scale. The EQ VAS 'thermometer' has endpoints of 100 ("The best health you can imagine") at the top and 0 ("The worst health you can imagine") at the bottom.

In the analysis the index value was considered as a continuous variable.

Composite Response Index in Diffuse Cutaneous Systemic Sclerosis

The CRISS tool summarizes the changes in the clinical and patient-reported outcomes using a single composite score that reflects the probability that the patient with dcSSc has improved (Khanna D., et al., *Arthritis Care Res.* (*Hoboken*) 2016, 68(2):167-78). For an effective therapeutic agent of dcSSc, CRISS will be able to summarize the higher probability of improvement in a subject treated with RKB versus an ineffective agent (such as placebo). CRISS is a 2-step process as described below.

Step 1: Patients who developed new or worsening of cardiopulmonary and/or renal involvement due to SSc are considered as not improved (irrespective of improvement in other core items) and assigned a probability of improving equal to 0.0. Specifically if a subject developes any of the following: new scleroderma renal crisis; decline in FVC % predicted≥15% (relative), confirmed by another FVC % within a month, high resolution computer tomography (HRCT) to confirm ILD (if previous HRCT of chest did not show ILD) and FVC % predicted below 80% predicted; new onset of left ventricular failure (defined as left ventricular ejection fraction≤45%) requiring treatment; or new onset of PAH on right heart catheterization requiring treatment (attributable to SSc) (PAH is defined as mean pulmonary artery pressure≥25 mm Hg at rest and an end-expiratory pulmonary artery wedge pressure≤15 mm Hg and a pulmonary vascular resistance>3 Wood units).

Step 2: For the remaining patients, Step 2 involves computing the predicted probability of improving for each subject using the following equation (equation derived predicted probabilities from a logistic regression model):

$$\frac{\exp(-5.54 - 0.81 * \Delta MRSS + 0.21 * \Delta FCV\% - 0.40 * \Delta Pt - glob - 0.44 * \Delta MD - glob - 3.41 * \Delta HAQ - DI)}{1 + \exp(-5.54 - 0.81 * \Delta MRSS + 0.21 * \Delta FVC\% - 0.40 * \Delta Pt - glob - 0.44 * \Delta MD - glob - 3.41 * \Delta HAQ - DI)}$$

wherein $\Delta$mRSS indicates the change in mRSS from baseline, $\Delta$FVC denotes the change in FVC % predicted from baseline, $\Delta$Pt-glob indicates the change in patient global assessment, $\Delta$MD-glob denotes the change in physician global assessment, and $\Delta$HAQ-DI is the change in HAQ-DI. All changes are absolute change (Time$_2$–Time$_{baseline}$).

Patient and physician global assessments of overall health were used in the Step 2 calculation of CRISS. These two assessments were based upon a Likert scale ranging from 0 (Excellent) to 10 (Extremely Poor) (Khanna D., et al., *Arthritis Care Res.* 2016, 68(2):167-78). Statistics Primary Efficacy Analysis The change in mRSS from baseline to Week 24 was analyzed in the ITT population using a MMRM approach. All post-baseline data available from Week 4 to Week 24 analysis windows were included in the analysis, regardless of adherence to treatment. The model includes the fixed categorical effects of treatment group (placebo, RKB), randomization strata (as per IRT, SSc-ILD: Yes/No), time point (Week 4, Week 8, Week 12, Week 24), randomization strata-by-time point interaction and treatment-by-time point interaction, as well as the continuous fixed covariates of baseline mRSS value and baseline value-by-time point interaction.

Results

Study Patients

A total of 143 patients were screened resulting in a randomization of 97 patients: 49 patients in the placebo group, 48 patients in the SAR15697 group. All patients randomized were exposed to Investigational medicinal product (IMP) which resulted in all 97 patients being included in the safety population. All 97 patients are included in the ITT population (Table 1).

TABLE 1

Summary of keys analysis populations

| | Placebo qw | RKB 200 mg qw | All |
|---|---|---|---|
| Randomized population | 49 (100) | 48 (100) | 97 (100) |
| Safety population | 49 | 48 | 97 |
| Intent To Treat population (ITT) | 49 | 48 | 97 |

Note:
In the Safety population, patients are tabulated according to treatment actually received (as treated). For the other populations, patients are tabulated according to their randomized treatment The intent-to-treat is defined as all randomized patients. Patients in the ITT population will be analyzed according to the treatment group allocated by randomization.

Patient Disposition

TABLE 2

Patient disposition for end of treatment - Randomized populationn

|  | Placebo qw (N = 49) | RKB 200 mg qw (N = 48) | All (N = 97) |
|---|---|---|---|
| Randomized and not treated | 0 | 0 | 0 |
| Randomized and treated | 49 (100) | 48 (100) | 97 (100) |
| Completed the study treatment period | 43 (87.8) | 44 (91.7) | 87 (89.7) |
| Ongoing in treatment period | 0 | 0 | 0 |
| Did not complete the study treatment period | 6 (12.2) | 4 (8.3) | 10 (10.3) |
| Subject's decision for treatment discontinuation | 3 (6.1) | 0 | 3 (3.1) |
| Reason for treatment period discontinuation |  |  |  |
| Adverse event | 1 (2.0) | 2 (4.2) | 3 (3.1) |
| Lack of efficacy | 3 (6.1) | 1 (2.1) | 4 (4.1) |
| Poor compliance to protocol | 0 | 0 | 0 |
| Progressive disease | 0 | 0 | 0 |
| Other | 2 (4.1) | 1 (2.1) | 3 (3.1) |

Note:
Percentages are calculated using the number of patients randomized as denominator Demographics and Baseline Characteristics The overall demographics and patient characteristics at baseline were similar between the two treatment groups, although the patients in the RKB group were slightly older (Table 3).

TABLE 3

Demographics and patient characteristics at baseline - Randomized population.

|  | Placebo qw (N = 49) | RKB 200 mg qw (N = 48) | All (N = 97) |
|---|---|---|---|
| Age (years) |  |  |  |
| Number | 49 | 48 | 97 |
| Mean (SD) | 47.2 (12.1) | 52.3 (10.8) | 49.7 (11.7) |
| Median | 45.0 | 53.0 | 51.0 |
| Min; Max | 27; 72 | 20; 78 | 20; 78 |
| Age group (years) [n(%)] |  |  |  |
| Number | 49 | 48 | 97 |
| <45 | 23 (46.9) | 10 (20.8) | 33 (34.0) |
| [45-65[ | 22 (44.9) | 33 (68.8) | 55 (56.7) |
| [65-75[ | 4 (8.2) | 4 (8.3) | 8 (8.2) |
| >75 | 0 | 1 (2.1) | 1 (1.0) |
| Sex [n(%)] |  |  |  |
| Number | 49 | 48 | 97 |
| Male | 11 (22.4) | 9 (18.8) | 20 (20.6) |
| Female | 38 (77.6) | 39 (81.3) | 77 (79.4) |
| Race [n(%)] |  |  |  |
| Number | 49 | 48 | 97 |
| American Indian or Alaska Native | 0 | 1 (2.1) | 1 (1.0) |
| Asian | 1 (2.0) | 0 | 1 (1.0) |
| Black or African American | 2 (4.1) | 2 (4.2) | 4 (4.1) |
| Native Hawaiian or other Pacific Islander | 1 (2.0) | 0 | 1 (1.0) |
| White | 45 (91.8) | 45 (93.8) | 90 (92.8) |
| Not reported [a] | 0 | 0 | 0 |
| Unknown [b] | 0 | 0 | 0 |
| Ethnicity [n(%)] |  |  |  |
| Number | 49 | 48 | 97 |
| Hispanic or Latino | 12 (24.5) | 10 (20.8) | 22 (22.7) |
| Not Hispanic or Latino | 37 (75.5) | 38 (79.2) | 75 (77.3) |
| Not reported [a] | 0 | 0 | 0 |
| Unknown [b] | 0 | 0 | 0 |
| BMI (kg/m$_2$) |  |  |  |
| Number | 49 | 48 | 97 |
| Mean (SD) | 24.9 (5.3) | 24.3 (4.4) | 24.6 (4.9) |

TABLE 3-continued

Demographics and patient characteristics at baseline - Randomized population.

|  | Placebo qw (N = 49) | RKB 200 mg qw (N = 48) | All (N = 97) |
|---|---|---|---|
| Median | 23.2 | 24.4 | 23.9 |
| Min; Max | 18; 41 | 16; 33 | 16; 41 |
| Weight (kg) |  |  |  |
| Number | 49 | 48 | 97 |
| Mean (SD) | 68.1 (18.0) | 67.1 (15.3) | 67.6 (16.6) |
| Median | 61.5 | 64.5 | 62.4 |
| Min; Max | 46; 118 | 36; 105 | 36; 118 |

[a] If a subject chooses not to report his Ethnicity/Race or if there are country restrictions to collect the information, it should be entered as Not Reported.
[b] The subject does not know his Race/Ethnicity The overall disease characteristics and history at baseline were similar between the two treatment groups, although the patients in the RKB group had a slightly shorter mean disease duration from the time of first non-Raynaud's phenomenon compared to the placebo group and had a slightly higher FVC and DLco at baseline (Table 4).

TABLE 4

SSc history and relevant baseline's characteristics - Randomized population

|  | Placebo qw (N = 49) | RKB 200 mg qw (N = 48) | All (N = 97) |
|---|---|---|---|
| Disease duration from the time of first non Raynaud's phenomenon manifestation (months) |  |  |  |
| Number | 49 | 48 | 97 |
| Mean (SD) | 21.8 (10.7) | 19.3 (9.2) | 20.6 (10.0) |
| Median | 25.4 | 19.4 | 20.0 |
| Q1; Q3 | 10.2; 32.1 | 11.7; 25.9 | 10.7; 29.1 |
| Min; Max | 5; 36 | 6; 36 | 5; 36 |
| mRSS at baseline |  |  |  |
| Number | 49 | 48 | 97 |
| Mean (SD) | 20.6 (7.0) | 20.5 (6.1) | 20.6 (6.5) |
| Median | 18.0 | 19.5 | 19.0 |
| Min; Max | 10; 35 | 11; 35 | 10; 35 |
| Predicted FVC(%) at baseline |  |  |  |
| Number | 49 | 48 | 97 |
| Mean (SD) | 89.5 (15.8) | 96.1 (17.4) | 92.8 (16.9) |
| Median | 91.9 | 97.3 | 93.0 |
| Q1; Q3 | 77.0; 98.0 | 83.7; 108.8 | 83.0; 105.7 |
| Min; Max | 48; 127 | 54; 127 | 48; 127 |
| Predicted HGB Corrected DLCO (%) at baseline |  |  |  |
| Number | 49 | 48 | 97 |
| Mean (SD) | 66.5 (14.6) | 72.4 (14.2) | 69.4 (14.7) |
| Median | 67.3 | 72.7 | 70.0 |
| Q1; Q3 | 56.1; 74.1 | 60.6; 82.7 | 58.9; 77.9 |
| Min; Max | 38; 102 | 39; 102 | 38; 102 |

MedDRA 21.1
Note:
A patient can be counted in several scleroderma history categories If the day of date of non raynaud's phenomenon manifestation is missing, then the date will be imputed with the first day of the month; if the month is missing, then the date will be imputed with the first January
Baseline data are described, i.e. the last available value before or equal to the datetime of the first double-blind IMP administration (or before or equal to the datetime of randomization when the patient is randomized and not treated)

Twenty-nine patients (59.2%) took background therapy within 3 months prior to baseline and during the course of the study in placebo group versus 25 patients (52.1%) in the RKB group (Table 5).

TABLE 5

Prior and concomitant backsround therapy taken within 3 months prior to baseline - Randomized population

|  | Placebo qw (N = 49) | RKB 200 mg qw (N = 48) |
|---|---|---|
| Any prior and concomitant background medications | 29 (59.2) | 25 (52.1) |

ATC: Anatomical therapeutic chemical,
IMP: Investigational Medicinal Product
WHO-DDE 2018 MARCH 1
Note:
A medication can be counted in several ATC classes
Prior and concomitant medications are those the subject has taken within 3 months prior to first IMP intake and has continued to take during the TEAE period.
Anatomic classes are sorted by decreasing frequency in the overall treatment group.
Standardized medication names are sorted by decreasing frequency in the overall treatment group within each anatomic class.
Patients who received background therapy are defined as all patients who took a medication from the following list before and at baseline: METHOTREXATE_mono_and_multiingredients, MYCOPHENOLATE_MOFETIL_mono_and_multi_ingredients, AZATHIOPRINE_mono_and_multi_ingredients, CICLOSPORIN_mono_and_multi_ingredients or CYCLOPHOSPHAMIDE_mono_and_multi_ingredients.

Ten (10.3%) patients were mis-stratified in IVRS based upon an examination of the patients' medical history (Table 6). More specifically, 6 patients stratified as having SSc-ILD in IVRS did not have a recorded medical history of it in the clinical database whereas, 4 patients who did not get stratified as having SSc-ILD in IVRS did have a recorded medical history of it in the clinical database.

TABLE 6

Summary of patients with discrepancies in stratification factor between clinical and IVRS database - Randomized population

| Stratum (as per IVRS) Actual Stratum (as per Clinical Database) | Placebo qw (N = 49) | RKB 200 mg qw (N = 48) | All (N = 97) |
|---|---|---|---|
| Stratification stratum at randomisation | 49/49 (100) | 48/48 (100) | 97/97 (100) |
| With medical history of SSc-ILD[a] | 18/49 (36.7) | 18/48 (37.5) | 36/97 (37.1) |
| With medical history of SSc-ILD[b] | 14/49 (28.6) | 16/48 (33.3) | 30/97 (30.9) |
| Without medical history of SSc-ILD[b] | 4/49 (8.2) | 2/48 (4.2) | 6/97 (6.2) |
| Without medical history of SSc-ILD[a] | 31/49 (63.3) | 30/48 (62.5) | 61/97 (62.9) |
| With medical history of SSc-ILD[b] | 4/49 (8.2) | 0/48 | 4/97 (4.1) |
| Without medical history of SSc-ILD[b] | 27/49 (55.1) | 30/48 (62.5) | 57/97 (58.8) |

SSC-ILD: SSc-Interstitial Lung Disease
[a]as per IVRS
[b]as per Clinical Database The historical antibody profile (Table 7) was relatively evenly distributed between the two treatment groups and this was indirectly confirmed by looking at the ANA staining pattern (Table 8) obtained at baseline, particularly for the centromere positive group.

TABLE 7

Descriptive summary table for specific systemic sclerosis auto-antibodies at baseline - Randomized population.

| Laboratory Parameter | Placebo qw (N = 49) | RKB 200 mg qw (N = 48) | All (N = 97) |
|---|---|---|---|
| Centromere Antibodies [n(%)] | | | |
| Number | 35 | 43 | 78 |
| Negative | 31 (88.6) | 33 (76.7) | 64 (82.1) |
| Positive | 4 (11.4) | 10 (23.3) | 14 (17.9) |
| RNA Polymerase III Antibody [n(%)] | | | |
| Number | 23 | 28 | 51 |
| Negative | 14 (60.9) | 22 (78.6) | 36 (70.6) |
| Positive | 9 (39.1) | 6 (21.4) | 15 (29.4) |

TABLE 7-continued

Descriptive summary table for specific systemic sclerosis auto-antibodies at baseline - Randomized population.

| Laboratory Parameter | Placebo qw (N = 49) | RKB 200 mg qw (N = 48) | All (N = 97) |
|---|---|---|---|
| Scl-70 Antibody [n(%)] | | | |
| Number | 36 | 46 | 82 |
| Negative | 15 (41.7) | 30 (65.2) | 45 (54.9) |
| Positive | 21 (58.3) | 16 (34.8) | 37 (45.1) |

Note:
Percentages are calculated using the number of patients randomized as denominator

TABLE 8

Descriptive summary table for ANA and ANAPATT at baseline - Randomized population

| | Placebo qw (N = 49) | RKB 200 mg qw (N = 48) | All (N = 97) |
|---|---|---|---|
| ANAPATT - ANA | | | |
| Number | 49 | 48 | 97 |
| Positive | 49 (100) | 48 (100) | 97 (100) |
| CENTROMERE | | | |
| Number | 6 | 8 | 14 |
| >1:1280 | 6 (100) | 8 (100) | 14 (100) |
| HOMOGENOUS | | | |
| Number | 20 | 14 | 34 |
| 1:1280 | 6 (31.6) | 8 (57.1) | 14 (42.4) |
| 1:320 | 1 (5.3) | 4 (28.6) | 5 (15.2) |
| 1:640 | 4 (21.1) | 0 | 4 (12.1) |
| >1:1280 | 9 (47.4) | 2 (14.3) | 11 (33.3) |
| NUCLEOLAR | | | |
| Number | 12 | 10 | 22 |
| 1:1280 | 3 (25.0) | 2 (20.0) | 5 (22.7) |
| 1:640 | 2 (16.7) | 1 (10.0) | 3 (13.6) |
| >1:1280 | 7 (58.3) | 7 (70.0) | 14 (63.6) |
| SPECKLED | | | |
| Number | 13 | 14 | 27 |
| 1:1280 | 2 (16.7) | 7 (50.0) | 9 (34.6) |
| 1:160 | 0 | 1 (7.1) | 1 (3.8) |
| 1:320 | 1 (8.3) | 0 | 1 (3.8) |
| 1:640 | 5 (41.7) | 1 (7.1) | 6 (23.1) |
| >1:1280 | 5 (41.7) | 5 (35.7) | 10 (38.5) |

TABLE 9

Summary of extent of exposure - Safety population

| | Placebo qw (N = 49) | RKB 200 mg qw (N = 48) |
|---|---|---|
| Cumulative exposure to treatment (Patient years) | 20.8 | 21.1 |
| Duration of IMP injection exposure (weeks) | | |
| Number | 49 | 48 |
| Mean (SD) | 22.2 (5.3) | 22.9 (4.1) |
| Median | 24.0 | 24.0 |
| Min; Max | 4; 24 | 1; 25 |
| Duration of IMP injection exposure by category [n (%)] | | |
| [1 day; 1 week[ | 0 | 0 |
| [1 week; 2 weeks[ | 0 | 1 (2.1) |
| [2 weeks; 4 weeks[ | 0 | 0 |
| [4 weeks; 6 weeks[ | 3 (6.1) | 0 |
| [6 weeks; 8 weeks[ | 0 | 0 |
| [8 weeks; 12 weeks[ | 0 | 1 (2.1) |
| [12 weeks; 16 weeks[ | 2 (4.1) | 1 (2.1) |
| [16 weeks; 20 weeks[ | 1 (2.0) | 1 (2.1) |
| [20 weeks; 24 weeks[ | 9 (18.4) | 6 (12.5) |
| ≥24 weeks | 34 (69.4) | 38 (79.2) |
| Number of patients by duration of IMP injection exposure [n (%)] | | |
| ≥1 day | 49 (100) | 48 (100) |
| ≥1 week | 49 (100) | 48 (100) |
| ≥2 weeks | 49 (100) | 47 (97.9) |
| ≥4 weeks | 49 (100) | 47 (97.9) |
| ≥6 weeks | 46 (93.9) | 47 (97.9) |
| ≥8 weeks | 46 (93.9) | 47 (97.9) |
| ≥12 weeks | 46 (93.9) | 46 (95.8) |
| ≥16 weeks | 44 (93.9) | 45 (93.8) |
| ≥20 weeks | 43 (87.8) | 44 (91.7) |
| ≥24 weeks | 34 (69.4) | 38 (79.2) |

IMP: Investigational Medicinal Product

Figure 3:
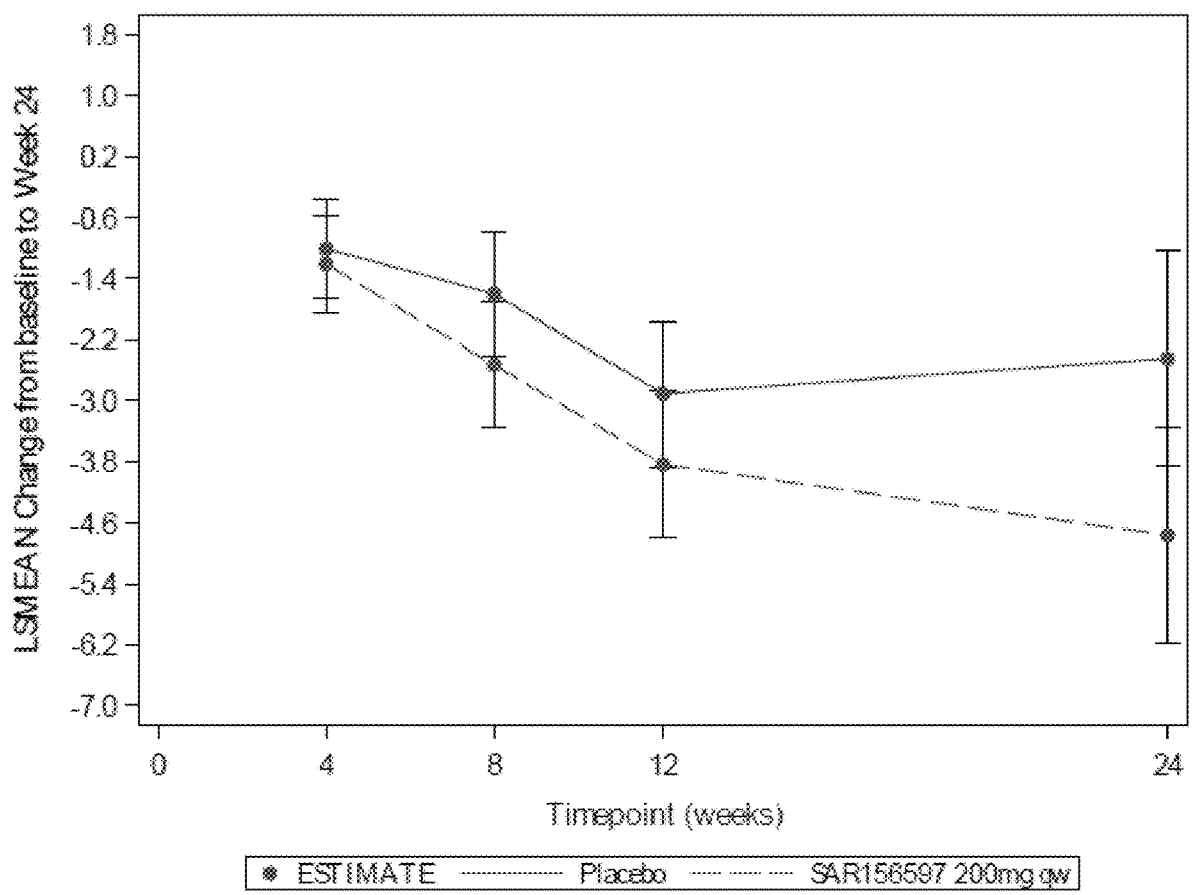
FIG. 3 is a graph showing the least square mean change in mRSS at each visit. 90% confidence intervals are given for each estimate. Solid line represents patient who received a placebo, dashed line represents patients who received 200 mg qw RKB.

Note:
Patients are considered in the treatment group they actually received (as treated)
The duration of IMP injection exposure in weeks is defined as: (last dose date +7 - first dose of date)/7, regardless of intermittent discontinuations, for patients with an end of treatment page filled in; ((min(« Database extraction date», date of planned end of treatment visit Week 24 (Day 169)) - first IMP injection date)/7, otherwise Efficacy
Primary Efficacy Endpoint
Main Analysis There was a significant difference between the RKB group compared to placebo as shown in Table 10 and FIG. 3. The mean change in mRSS from baseline at Week 24 was −2.45 (0.85) and −4.76 (0.86) for the placebo and RKB groups, respectively, yielding a decrease of 2.31 (1.21) with an associated one-sided p-value=0.0291.

TABLE 10

Absolute change in mRSS from baseline to Week 24 - MMRM - ITT population

| | Placebo qw (N = 49) | RKB 200 mg qw (N = 48) |
|---|---|---|
| Change from baseline to week 4 | | |
| Number | 48 | 48 |
| LSMean (SE)$^a$ | −1.01 (0.38) | −1.21 (0.38) |
| Change from baseline to week 8 | | |
| Number | 48 | 47 |
| LSMean (SE)$^a$ | −1.60 (0.49) | −2.54 (0.50) |

TABLE 10-continued

Absolute change in mRSS from baseline to Week 24 - MMRM - ITT population

|  | Placebo qw (N = 49) | RKB 200 mg qw (N = 48) |
|---|---|---|
| Change from baseline to week 12 | | |
| Number | 47 | 47 |
| LSMean (SE)[a] | −2.91 (0.58) | −3.84 (0.58) |
| Change from baseline to week 24 (EOT) | 48 | 47 |
| LSMean (SE)[a] | −2.45 (0.85) | −4.76 (0.86) |
| 95% CI | (−4.14; −0.76) | (−6.46; −3.06) |
| LS Mean difference vs Placebo[a] (SE) | | 2.31 (1.21) |
| 90% CI | | (0.31; 4.32) |
| 95% CI | | (−0.08; 4.71) |
| One sided p-value VS Placebo[a] | | 0.0291 |

Note:
CI confidence interval;
MMRM: Mixed Model for Repeated Measurements;
mRSS: modified Rodnan Skin Score;
LS mean: Least square means calculated using mixed model;
SE: Standard error;
EOT: End of treatment;
[a]LS means, SE and p-value were estimated from MMRM analysis. The model includes the fixed categorical effects of treatment group, randomization strata as per IVRS, time point, treatment-by-time point and strata-by-time point interactions, as well as the continuous fixed effects of baseline and baseline-by-timepoint interactions.
Model and data description (based on observed data) run on patients with a baseline and a post-baseline value in at least one of the analysis windows Subgroup Analyses The subgroup analyses, based upon randomization stratum and background therapy, were performed.

In examining the stratified data based upon a medical history of SSc-ILD per IVRS (Table 11), the mean change in mRSS from baseline at Week 24 was −1.48 (1.09) and −4.09 (1.08) for the placebo and RKB groups, respectively for those without a medical history of SSc-ILD. For those with a medical history of SSc-ILD, the mean change in mRSS from baseline at Week 24 was −4.08 (1.41) and −5.82 (1.42), respectively. The mean differences between the strata were not significant.

TABLE 11

|  | Without medical history of SSc-ILD (N = 61) | | With medical history of SSc-ILD (N = 36) | | |
|---|---|---|---|---|---|
|  | Placebo qw (N = 31) | RKB 200 mg qw (N = 30) | Placebo qw (N = 18) | RKB 200 mg qw (N = 18) | Interaction p-value |
| Change from baseline to week 4 | | | | | |
| Number | 30 | 30 | 18 | 18 | |
| LSMean (SE)[a] | −0.72 (0.49) | −1.03 (0.49) | −1.49 (0.63) | −1.52 (0.63) | |
| Change from baseline to week 8 | | | | | |
| Number | 30 | 29 | 18 | 18 | |
| LSMean (SE)[a] | −1.66 (0.62) | −1.73 (0.63) | −1.51 (0.81) | −3.86 (0.80) | |
| Change from baseline to week 12 | | | | | |
| Number | 29 | 29 | 18 | 18 | |
| LSMean (SE)[a] | −2.45 (0.73) | −2.45 (0.73) | −3.73 (0.94) | −6.13 (0.93) | |

TABLE 11-continued

|  | Without medical history of SSc-ILD (N = 61) | | With medical history of SSc-ILD (N = 36) | | |
| --- | --- | --- | --- | --- | --- |
|  | Placebo qw (N = 31) | RKB 200 mg qw (N = 30) | Placebo qw (N = 18) | RKB 200 mg qw (N = 18) | Interaction p-value |
| Change from baseline to week 24 (EOT) | | | | | |
| LSMean (SE)[a] | 30 | 30 | 18 | 17 | |
| 95% CI | −1.48 (1.09) | −4.09 (1.08) | −4.08 (1.41) | −5.82 (1.42) | |
| LS Mean difference vs Placebo[a] (SE) | 2.61 (1.53) | | 1.74 (2.00) | | 0.7305 |
| 90% CI | (0.06; 5.15) | | (−1.59; 5.06) | | |
| 95% CI | (−0.44; 5.65) | | (−2.24; 5.71) | | |

Note:
CI confidence interval;
MMRM: Mixed Model for Repeated Measurements;
mRSS: modified Rodnan Skin Score;
SSc: Systemic sclerosis;
ILD: Interstitial Lung Disease;
LS mean: Least square means calculated using mixed model;
EOT: End of treatment;
SE: Standard error;
[a]LS means, SE and p-value were estimated from MMRM analysis. The model includes the fixed categorical effects of treatment group, randomization strata as per IVRS, time point, treatment-by-time point and strata-by-time point interactions, as well as the continuous fixed effects of baseline and baseline-by-timepoint interactions.
Model and data description (based on observed data) run on patients with a baseline and a post-baseline value in at least one of the analysis windows
Randomization stratum is chosen according to IVRS.

In the subgroup analysis based on background therapy (Table 12), the mean change in mRSS from baseline at Week 24 was −0.95 (1.34) and −3.64 (1.24) for the placebo and RKB groups, respectively for those without background therapy. For those with background therapy, the mean change in mRSS from baseline at Week 24 was −3.43 (1.08) and −5.81 (1.17), respectively. Similarly, the mean differences between the subgroups were not significant.

TABLE 12

Absolute change in mRSS from baseline to week 24 by background therapy - MMRM - ITT population

|  | Without background therapy (N = 43) | | With background therapy (N = 54) | | |
| --- | --- | --- | --- | --- | --- |
|  | Placebo qw (N = 20) | RKB 200 mg qw (N = 23) | Placebo qw (N = 29) | RKB 200 mg qw (N = 25) | Interaction p-value |
| Change from baseline to week 4 | | | | | |
| Number | 19 | 23 | 29 | 25 | |
| LSMean (SE)[a] | −0.87 (0.62) | −1.09 (0.56) | −1.10 (0.50) | −1.32 (0.54) | |
| Change from baseline to week 8 | | | | | |
| Number | 19 | 22 | 29 | 25 | |
| LSMean (SE)[a] | −1.02 (0.78) | −1.65 (0.72) | −1.98 (0.63) | −3.33 (0.68) | |
| Change from baseline to week 12 | | | | | |
| Number | 19 | 22 | 28 | 25 | |
| LSMean (SE)[a] | −2.20 (0.90) | −2.44 (0.82) | −3.38 (0.73) | −5.09 (0.78) | |

TABLE 12-continued

Absolute change in mRSS from baseline to week 24 by background therapy - MMRM - ITT population

| | Without background therapy (N = 43) | | With background therapy (N = 54) | | |
|---|---|---|---|---|---|
| | Placebo qw (N = 20) | RKB 200 mg qw (N = 23) | Placebo qw (N = 29) | RKB 200 mg qw (N = 25) | Interaction p-value |
| Change from baseline to week 24 (EOT) | | | | | |
| Number | 19 | 22 | 29 | 25 | |
| LSMean (SE)$^a$ | −0.95 (1.34) | −3.64 (1.24) | −3.43 (1.08) | −5.81 (1.17) | |
| 95% CI | (−3.61; 1.71) | (−6.10; −1.17) | (−5.59; −1.28) | (−8.14; −3.49) | |
| LS Mean difference vs Placebo$^a$ (SE) | | 2.69 (1.83) | | 2.38 (1.59) | 0.9001 |
| 90% CI | | (−0.35; 5.72) | | (−0.27; 5.03) | |
| 95% CI | | (−0.94; 6.31) | | (−0.79; 5.55) | |

Note:
CI confidence interval;
MMRM: Mixed Model for Repeated Measurements;
mRSS: modified Rodnan Skin Score;
LS mean: Least square means calculated using mixed model;
EOT: End of treatment;
SE: Standard error;
Patients who received background therapy are defined as all patients who took a medication from the following list before and at baseline: METHOTREXATE_mono_and_multiingredients, MYCOPHENOLATE_MOFETIL_mono_and_multi_ingredients, AZATHIOPRINE_mono_and_multi_ingredients, CICLOSPORIN_mono_and_multi_ingredients or CYCLOPHOSPHAMIDE_mono_and_multi_ingredients.
$^a$LS means, SE and p-value were estimated from MMRM analysis. The model includes the fixed categorical effects of treatment group, randomization strata as per IVRS, time point, treatment-by-time point and strata-by-time point interactions, as well as the continuous fixed effects of baseline and baseline-by-timepoint interactions.
Model and data description (based on observed data) run on patients with a baseline and a post-baseline value in at least one of the analysis windows Main Secondary Key Efficacy Endpoints

HAQ-DI

Figure 4:
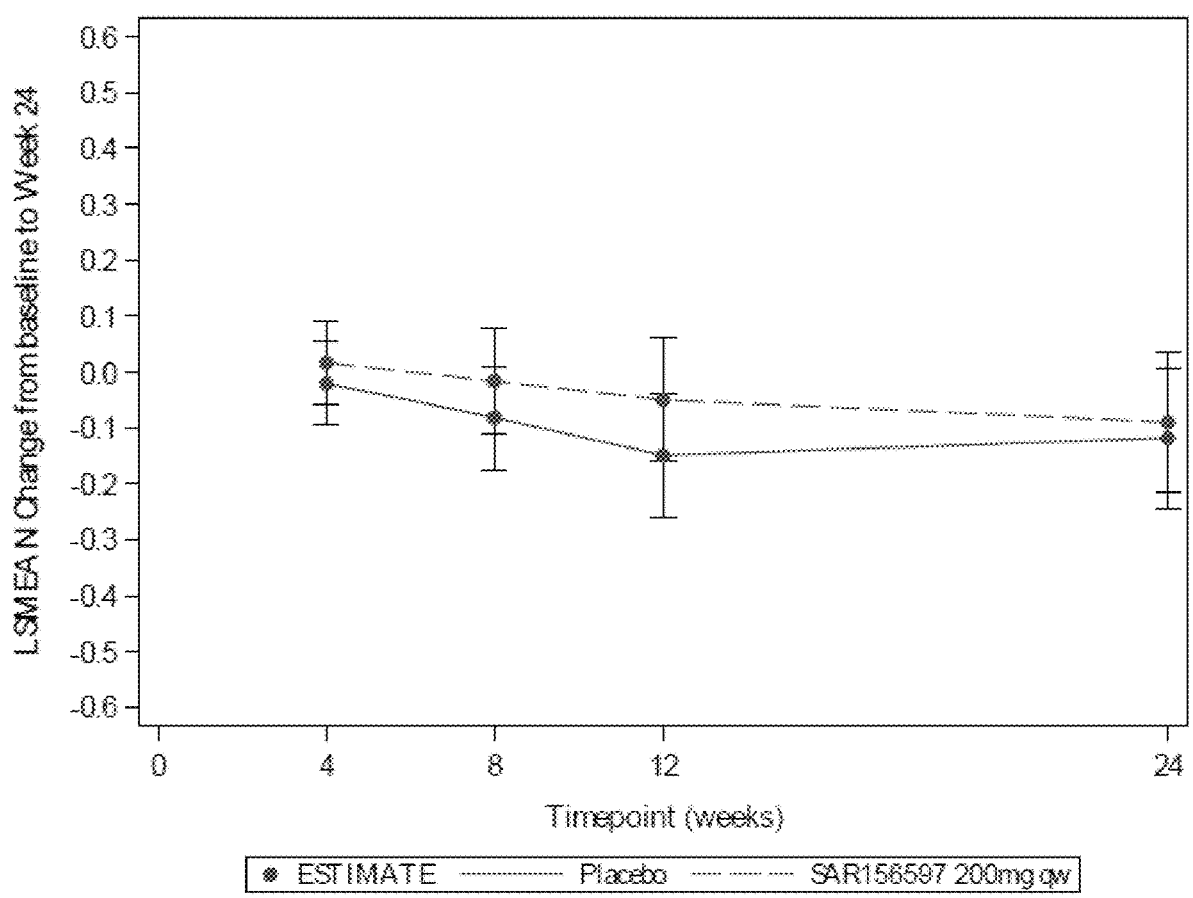
FIG. 4 is a graph showing the least square mean change in HAQ-DI composite score at each visit. 90% confidence intervals are given for each estimate. Solid line represents patient who received a placebo, dashed line represents patients who received 200 mg qw RKB.

No significant difference was observed between treatment groups for HAQ-DI. As shown in Table 13 and FIG. 4 the mean change in HAQ-DI from baseline at Week 24 was −0.12 (0.08) and −0.09 (0.08) for the placebo and RKB groups, respectively, yielding a difference of −0.03 (0.11) with an associated one-sided p-value=0.3975.

TABLE 13

Absolute change in HAQ-DI composite score from baseline to Week 24 - MMRM - ITT population

| | Placebo qw (N = 49) | RKB 200 mg qw (N = 48) |
|---|---|---|
| Change from baseline to week 4 | | |
| Number | 48 | 48 |
| LSMean (SE)$^a$ | −0.02 (0.05) | 0.02 (0.05) |
| Change from baseline to week 8 | | |
| Number | 48 | 47 |
| LSMean (SE)$^a$ | −0.08 (0.06) | −0.02 (0.06) |
| Change from baseline to week 12 | | |
| Number | 47 | 47 |
| LSMean (SE)$^a$ | −0.15 (0.07) | −0.05 (0.07) |
| Change from baseline to week 24 (EOT) | 48 | 47 |
| LSMean (SE)$^a$ | −0.12 (0.08) | −0.09 (0.08) |
| 95% CI | (−0.27; 0.03) | (−0.24; 0.06) |
| LS Mean difference vs Placebo$^a$ (SE) | | −0.03 (0.11) |

TABLE 13-continued

Absolute change in HAQ-DI composite score from baseline to Week 24 - MMRM - ITT population

| | Placebo qw (N = 49) | RKB 200 mg qw (N = 48) |
|---|---|---|
| 90% CI | | (−0.21; 0.15) |
| 95% CI | | (−0.24; 0.19) |
| One sided p-value VS Placebo$^a$ | | 0.3975 |

Note:
CI confidence interval;
MMRM: Mixed Model for Repeated Measurements;
LS mean: Least square means calculated using mixed model;
HAQ-DI: Health Assessment Questionnaire Disability Index;
SE: Standard error;
EOT: End of treatment;
$^a$LS means, SE and p-value were estimated from MMRM analysis. The model includes the fixed categorical effects of treatment group, randomization strata as per IVRS, time point, treatment-by-time point and strata-by-time point interactions, as well as the continuous fixed effects of baseline and baseline-by-timepoint interactions. Least-squares (LS) means, standard errors (SE) and p-value estimated from MMRM (mixed-effect model with repeated measures) analysis. The model includes the fixed categorical effects of treatment group, randomization strata as per IVRS, time point, treatment-by-time point and strata-by-time point interaction, as well as the continuous fixed
Model and data description (based on observed data) run on patients with a baseline and a post-baseline value in at least one of the analysis windows

FVC

Figure 5:
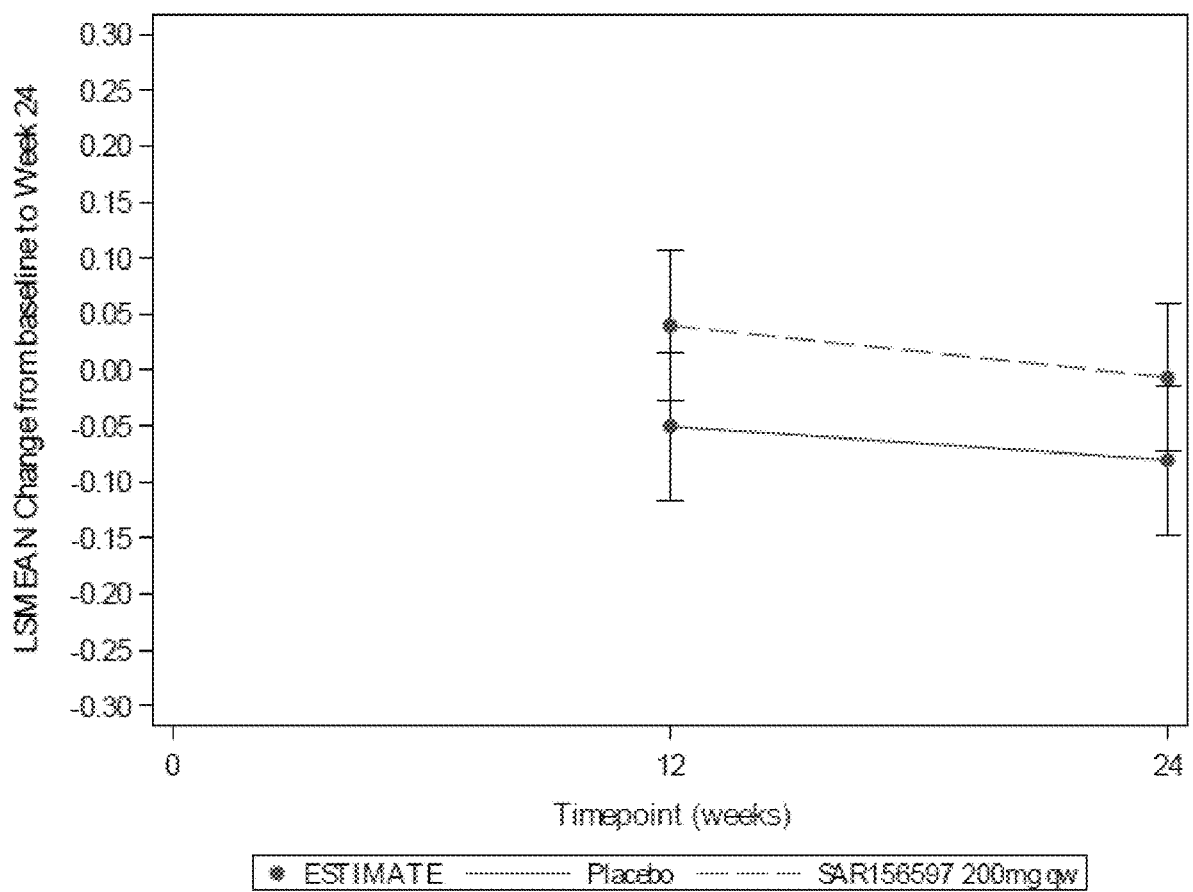
FIG. 5 is a graph showing the least square mean change in FVC (L) at each visit. 90% confidence intervals are given for each estimate. Solid line represents patient who received a placebo, dashed line represents patients who received 200 mg qw RKB.

No significant difference was observed between treatment groups for FVC (Table 14 and FIG. 5). The mean change in absolute FVC (L) from baseline at Week 24 was −0.08 (0.04) and −0.01 (0.04) for the placebo and RKB groups, respectively, yielding a difference of −0.07 (0.06) with an associated one-sided p-value=0.0964.

TABLE 14

Absolute change in FVC (L) from baseline to Week 24 - MMRM - ITT population

| Change from baseline to week 12 | Placebo qw (N = 49) | RKB 200 mg qw (N = 48) |
|---|---|---|
| Number | 46 | 46 |
| LSMean (SE)[a] | −0.05 (0.04) | 0.04 (0.04) |
| Change from baseline to week 24 (EOT) | 47 | 47 |
| LSMean (SE)[a] | −0.08 (0.04) | −0.01 (0.04) |
| 95% CI | (−0.16; −0.00) | (−0.09; 0.07) |
| LS Mean difference vs Placebo[a] (SE) | | −0.07 (0.06) |
| 90% CI | | (−0.17; 0.02) |
| 95% CI | | (−0.19; 0.04) |
| One sided p-value VS Placebo[a] | | 0.0964 |

Note:
CI confidence interval;
MMRM: Mixed Model for Repeated Measurements;
LS mean: Least square means calculated using mixed model;
FVC: Forced Vital Capacity;
SE: Standard error;
EOT: End of treatment;
[a] LS means, SE and p-value were estimated from MMRM analysis. The model includes the fixed categorical effects of treatment group, randomization strata as per IVRS, time point, treatment-by-time point and strata-by-time point interactions, as well as the continuous fixed effects of baseline and baseline-by-timepoint interactions.
Model and data description (based on observed data) run on patients with a baseline and a post-baseline value in at least one of the analysis windows Observed DLco (Corrected for Hemoglobin)

Figure 6:
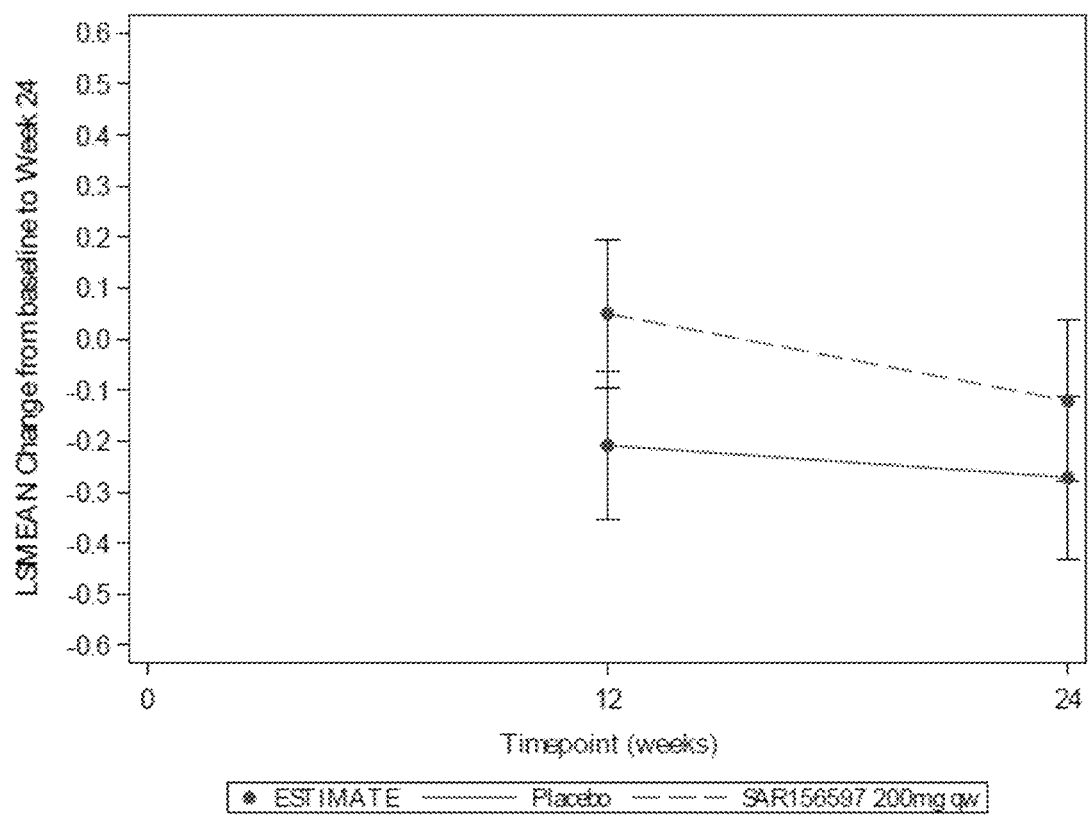
FIG. 6 is a graph showing the least square mean change in DLco (mmol/min/kPa) [corrected for hemoglobin] at each visit. 90% confidence intervals are given for each estimate. Solid line represents patient who received a placebo, dashed line represents patients who received 200 mg qw RKB.

No significant difference was observed between treatment groups for DLco (Table 15 and FIG. 6). The mean change in absolute DLco (mmol/min/kPa) from baseline at Week 24 was −0.27 (0.10) and −0.12 (0.10) for the placebo and RKB groups, respectively, yielding a difference of −0.15 (0.14) with an associated one-sided p-value=0.1352.

TABLE 15

Absolute change in DLco [corrected for hemoglobin] (mmol/min/kPa) from baseline to Week 24 - MMRM - ITT population.

| Change from baseline to week 12 | Placebo qw (N = 49) | RKB 200 mg qw (N = 48) |
|---|---|---|
| Number | 46 | 46 |
| LSMean (SE)[a] | −0.21 (0.09) | 0.05 (0.09) |
| Change from baseline to week 24 (EOT) | 46 | 47 |
| LSMean (SE)[a] | −0.27 (0.10) | −0.12 (0.10) |
| 95% CI | (−0.46; −0.08) | (−0.31; 0.07) |
| LS Mean difference vs Placebo[a] (SE) | | −0.15 (0.14) |
| 90% CI | | (−0.38; 0.08) |
| 95% CI | | (−0.42; 0.12) |
| One sided p-value VS Placebo[a] | | 0.1352 |

Note:
CI confidence interval;
MMRM: Mixed Model for Repeated Measurements;
LS mean: Least square means calculated using mixed model;
DLCO: carbon monoxide diffusing lung capacity;
SE: Standard error;
EOT: End of treatment;
[a] LS means, SE and p-value were estimated from MMRM analysis. The model includes the fixed categorical effects of treatment group, randomization strata as per IVRS, time point, treatment-by-time point and strata-by-time point interactions, as well as the continuous fixed effects of baseline and baseline-by-timepoint interactions.
Model and data description (based on observed data) run on patients with a baseline and a post-baseline value in at least one of the analysis windows Results of exploratory efficacy endpoints are shown in Table 16. Exploratory endpoints suggested possible effect of RKB on overall pain, Raynaud's and digital ulcers.

Romilkimab resulted in a statistically significant improvement in the EQ-5D-5L index compared with placebo; the LS mean (SE) change from baseline to week 24 was 0.07 (0.03) for romilkimab versus 0.00 (0.03) for placebo resulting in a difference of 0.07 [95% CI: −0.01, 0.15; p=0.04] (Table 2). There was a numerical improvement (i.e. decrease) across the SHAQ VAS scales for overall disease severity, pain severity, vascular function and digital ulcer impact on activity, and less worsening for GI function and breathing function from baseline to week 24 for romilkimab versus placebo, but these did not reach statistical significance (Table 2).

Additional exploratory efficacy endpoints are summarised in Supplement 4. At week 24, there was a numerical improvement (i.e. greater decrease) with romilkimab versus placebo in UCLA SCTC GIT 2.0 total score yielding an LS mean difference of −0.02 [95% CI: −0.14, 0.10; p=0.39] and in tender joint count 28 resulting in a difference of −1.08 [95% CI: −2.74, 0.58; p=0.10], but not digital ulcer count (LS mean difference: 0.10 [95% CI: −0.37, 0.57; p=0.33]). The mean (SD) predicted probability of improvement in CRISS was slightly higher with romilkimab than placebo: 0.4245 (0.4266) versus 0.3811 (0.4372), respectively.

TABLE 16

Exploratory endpoints

| | Placebo QW (n = 49) | Romilkimab 200 mg QW (n = 48) |
|---|---|---|
| SHAQ - VAS for overall disease severity | | |
| Baseline mean (SD) | 54.00 (27.62) | 42.71 (30.95) |
| LS mean (SE) change from baseline | −7.30 (3.12) [n = 48] | −12.72 (3.16) [n = 47] |
| LS mean difference [95% CI] (p-value) at week 24 | −5.42 [−14.32, 3.48] (0.11) | |
| SHAQ - VAS for pain severity | | |
| Baseline mean (SD) | 36.82 (26.72) | 28.65 (28.28) |
| LS mean (SE) change from baseline | 1.18 (3.44) [n = 48] | −6.94 (3.46) [n = 47] |
| LS mean difference [95% CI] (p-value) at week 24 | −8.12 [−17.87, 1.63] (0.05) | |
| SHAQ - VAS for gastrointestinal function | | |
| Baseline mean (SD) | 15.39 (22.25) | 7.54 (17.84) |
| LS mean (SE) change from baseline | 5.40 (3.06) [n = 48] | 3.21 (3.08) n = 47] |
| LS mean difference [95% CI] (p-value) at week 24 | −2.20 [−10.90, 6.51] (0.31) | |

TABLE 16-continued

Exploratory endpoints

|  | Placebo QW (n = 49) | Romilkimab 200 mg QW (n = 48) |
|---|---|---|
| SHAQ - VAS for breathing function | | |
| Baseline mean (SD) | 18.80 (23.96) | 10.38 (18.13) |
| LS mean (SE) change from baseline | 2.32 (2.63) [n = 48] | 0.14 (2.66) [n = 47] |
| LS mean difference [95% CI] (p-value) at week 24 | −2.18 [−9.70, 5.33] (0.28) | |
| SHAQ - VAS for vascular function (Raynaud's phenomenon) | | |
| Baseline mean (SD) | 39.90 (28.82) | 29.98 (32.07) |
| LS mean (SE) change from baseline | −4.26 (3.24) [n = 48] | −8.46 (3.27) [n = 47] |
| LS mean difference [95% CI] (p-value) at week 24 | −4.20 [−13.43, 5.02] (0.18) | |
| SHAQ - VAS for digital ulcer impact on activity | | |
| Baseline mean (SD) | 23.44 (32.78) [n = 48] | 15.00 (29.25) [n = 47] |
| LS mean (SE) change from baseline | 0.08 (3.38) [n = 48] | −6.10 (3.41) [n = 46] |
| LS mean difference [95% CI] (p-value) at week 24 | −6.18 [−15.74, 3.38] (0.10) | |
| EQ-5D-5L | | |
| Baseline mean (SD) | 0.58 (0.24) | 0.64 (0.18) |
| LS mean (SE) change from baseline | 0.00 (0.03) [n = 48] | 0.07 (0.03) [n = 47] |
| LS mean difference [95% CI] (p-value) at week 24 | 0.07 [−0.01, 0.15] (0.04) | |

CRISS Probability

No significant difference was observed between the treatment groups for Step 1 analysis of CRISS events (Table 17) and CRISS predicted probability of improvement (Table 18). There were a total of two events that met CRISS criteria with both events (decline in FVC) occurring in the placebo group. One additional CRISS event (scleroderma renal crisis) was reported at Week 35 from the RKB group and will be reflected in the CRISS analysis for the CSR.

TABLE 17

Description of the CRISS events over time by analysis timepoint - ITT population.

|  | Placebo qw (N = 49) | RKB 200 mg qw (N = 48) |
|---|---|---|
| Week 12 | | |
| CRISS-Decline in FVC | 1 (2.0) | 0 |
| CRISS-Scleroderma Renal Crisis | 0 | 0 |
| CRISS-New Onset Left Ventricular Failure | 0 | 0 |
| CRISS-New Onset of PAH on Right Arm | 0 | 0 |
| Total | 1 (2.0) | 0 |
| Week 24 (EOT) | | |
| CRISS-Decline in FVC | 2 (4.1) | 0 |
| CRISS-Scleroderma Renal Crisis | 0 | 0 |
| CRISS-New Onset Left Ventricular Failure | 0 | 0 |
| CRISS-New Onset of PAH on Right Arm | 0 | 0 |
| Total | 2 (4.1) | 0 |

Note:
CRISS = Composite Response Index for Diffuse Cutaneous Systemic Sclerosis (dcSSc);
FVC: Forced Vital Capacity;
PAH: Pulmonary Arterial Hypertension;
EOT: End of treatment;
EOS: End of study;

TABLE 18

Description of the distribution of predicted probability CRISS at weeks 12 and 24 ITT population

|  | Placebo qw (N = 49) | RKB 200 mg qw (N = 48) |
|---|---|---|
| Week 12 | | |
| Number | 45 | 44 |
| Mean (SD) | 0.2994 (0.3557) | 0.3694 (0.4092) |
| Median | 0.1598 | 0.0709 |
| Q1; Q3 | 0.0202; 0.4803 | 0.0083; 0.8506 |
| Min; Max | 0.000; 1.000 | 0.000; 1.000 |
| Week 24 (EOT) | | |
| Number | 47 | 46 |
| Mean (SD) | 0.3811 (0.4372) | 0.4337 (0.4266) |
| Median | 0.0578 | 0.1795 |
| Q1; Q3 | 0.0040; 0.8745 | 0.0194; 0.9307 |
| Min; Max | 0.000; 1.000 | 0.000; 1.000 |
| P-value from comparison between both groups at Week 24[a] | | 0.1966 |

CRISS = Composite Response Index for Diffuse Cutaneous Systemic Sclerosis (dcSSc)
CRISS reflects the probability that the patient improved his dcSSc
CRISS is a 2-step process. Step 1: the probability is equal to 0 if the patient develops new or worsening of cardiopulmonary and/or renal involvement due to SSc.
Step 2: $\exp(-5.54-0.81 \times \Delta MRSS + 0.21 \times \Delta FVCPP - 0.40 \times \Delta PT\_glob - 0.44 \times \Delta MD\_glob - 3.41 \times \Delta HAQDI)/(1 + \exp(-5.54-0.81 \times \Delta MRSS + 0.21 \times \Delta FVCPP - 0.40 \times \Delta PT\_glob - 0.44 \times \Delta MD\_glob - 3.41^* \times \Delta HAQDI))$
[a] provided using a Van Elteren's test stratified on randomized strata
The data were not imputed Prespecified Subgroup Analyses The LS mean difference in mRSS was statistically significantly in favour of romilkimab versus placebo in patients with more severely affected skin (i.e. baseline mRSS≥15 (−3.42 [95% CI: −6.21, −0.64; p=0.01]). Responder rate analysis indicated that 20%, 40%, and 60% improvements in mRSS from baseline to week 24 were higher for romilkimab than placebo; the between-group difference for 40% improvement in mRSS was statistically significant (p=0.02). The LS mean difference in mRSS was numerically in favour of romilkimab versus placebo at week 24, regardless of the baseline disease duration (<20 and ≥20 months), use of background therapy or medical history of SSc-ILD (Table 19).

TABLE 19

Mean change from baseline to week 24 in absolute mRSS for prespecified ITT subpopulations treated with romilkimab versus placebo.

|  | Placebo QW (n = 49) | Romilkimab 200 mg QW (n = 48) |
|---|---|---|
| Disease duration <20 months, n | 23 | 25 |
| LS mean (SE) change from baseline | −1.75 (1.24) | −5.09 (1.19) |
| LS mean difference [95% CI] at week 24 | −3.34 [−6.74, 0.07] | |
| Disease duration ≥20 months, n | 25 | 22 |
| LS mean (SE) change from baseline | −3.09 (1.19) | −4.40 (1.26) |
| LS mean difference [95% CI] at week 24 | −1.31 [−4.74, 2.12] | |
| Interaction p-value for disease duration | 0.41 | |
| With background medication[a], n | 29 | 25 |
| LS mean (SE) change from baseline | −3.43 (1.08) | −5.81 (1.17) |
| LS mean difference [95% CI] at week 24 | −2.38 [−5.55, 0.79] | |
| Without background medication[a], n | 19 | 22 |
| LS mean (SE) change from baseline | −0.95 (1.34) | −3.64 (1.24) |
| LS mean difference [95% CI] at week 24 | −2.69 [−6.31, 0.94] | |
| Interaction p-value for background medication | 0.90 | |
| With medical history of SSc-ILD, n | 18 | 17 |
| LS mean (SE) change from baseline | −4.08 (1.41) | −5.82 (1.42) |
| LS mean difference [95% CI] at week 24 | −1.74 [−5.71, 2.24] | |
| Without medical history of SSc-ILD, n | 30 | 30 |
| LS mean (SE) change from baseline | −1.48 (1.09) | −4.09 (1.08) |
| LS mean difference [95% CI] at week 24 | −2.61 [−5.65, 0.44] | |
| Interaction p-value for medical history of SSc-ILD | 0.73 | |

[a]Includes methotrexate, mycophenolate mofetil, azathioprine, and cyclophosphamide.
CI, confidence interval; ITT, intent-to-treat; LS, least-squares; mRSS, modified Rodnan skin score; QW, once-weekly; SE, standard error; SSc-ILD, systemic sclerosis interstitial lung disease.

Post-Hoc Analysis

Figure 7:
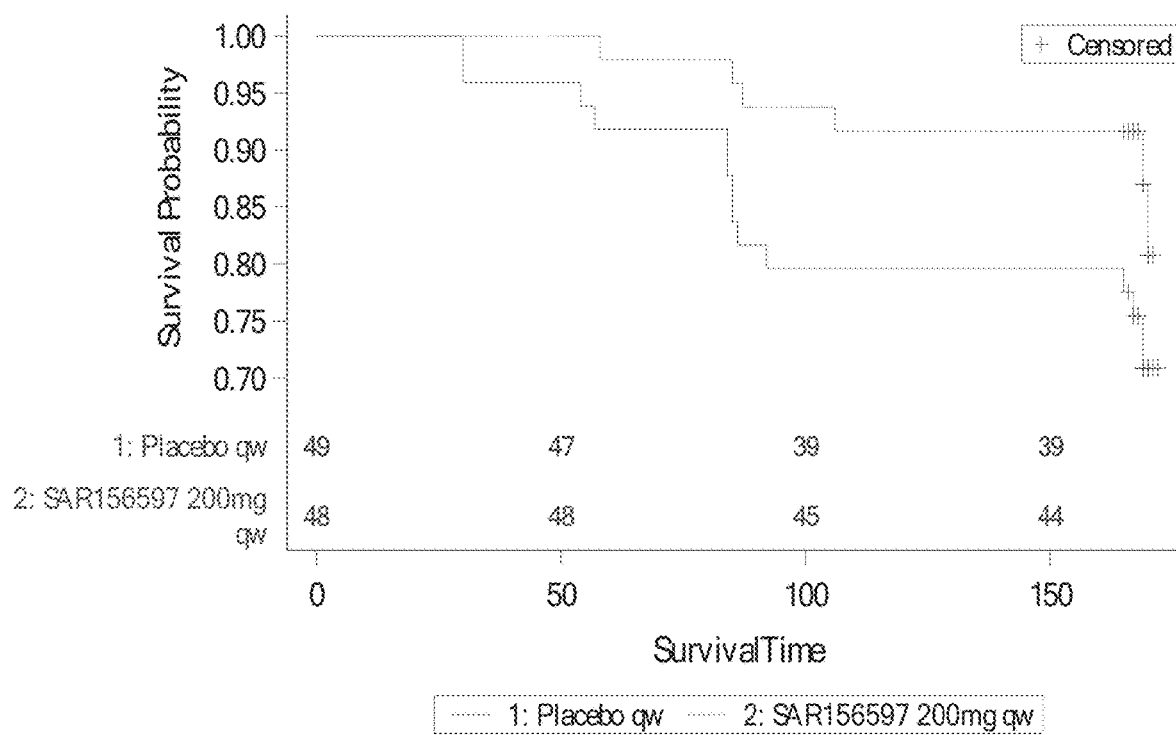
FIG. 7 is a graph showing Kaplan-Meier curves for time to first event reflecting progression in the romilkimab and placebo groups. QW, once-daily. *Censored=patients that left the study before an event occurred or the study ended before an event occurred.

Time to first event was longer with romilkimab versus placebo (FIG. 7). There was a trend of benefit for romilkimab in time to an event reflecting disease worsening compared with placebo: 9 (18.8%) versus 15 (30.6%) [hazard ratio: 0.47 [95% CI: 0.20, 1.11; p=0.09, two-sided], respectively (Table 20). This was driven by lung and skin events for romilkimab and by lung, skin and other CRISS events for placebo.

Pharmacokinetics, Immunogenicity and Biomarker Endpoints

Figure 8A:
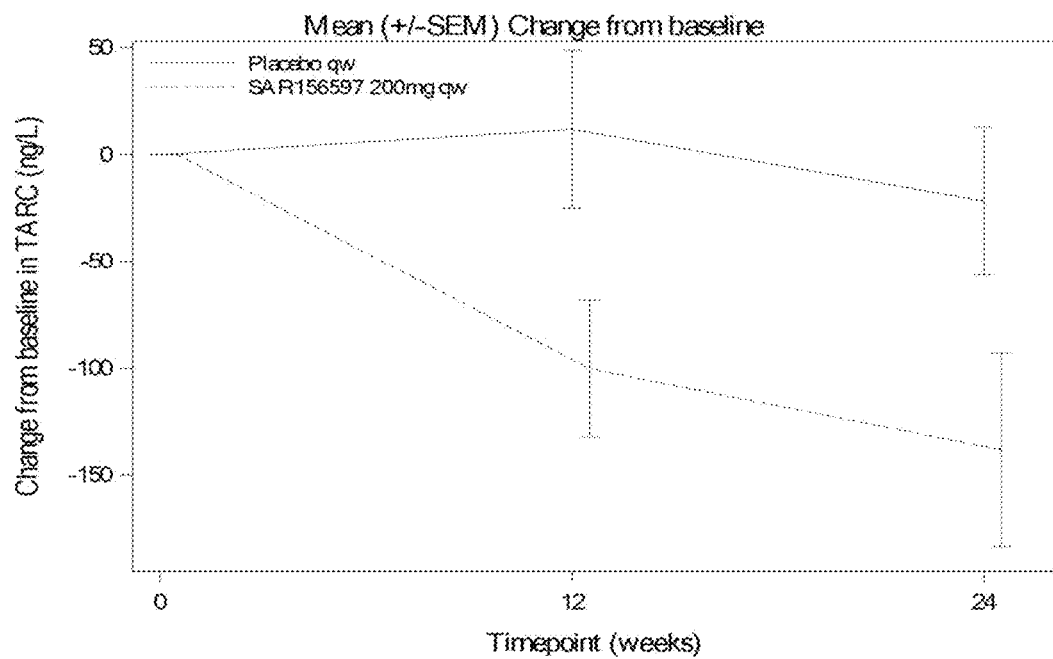
FIGS. 8A and 8B are graphs showing the mean change from baseline to week 24 for (FIG. 8A) TARC and (FIG. 8B) periostin in patients treated with romilkimab versus placebo. QW, once-weekly; SE, standard error; TARC, thymus and activation regulated chemokine.
Figure 8B:
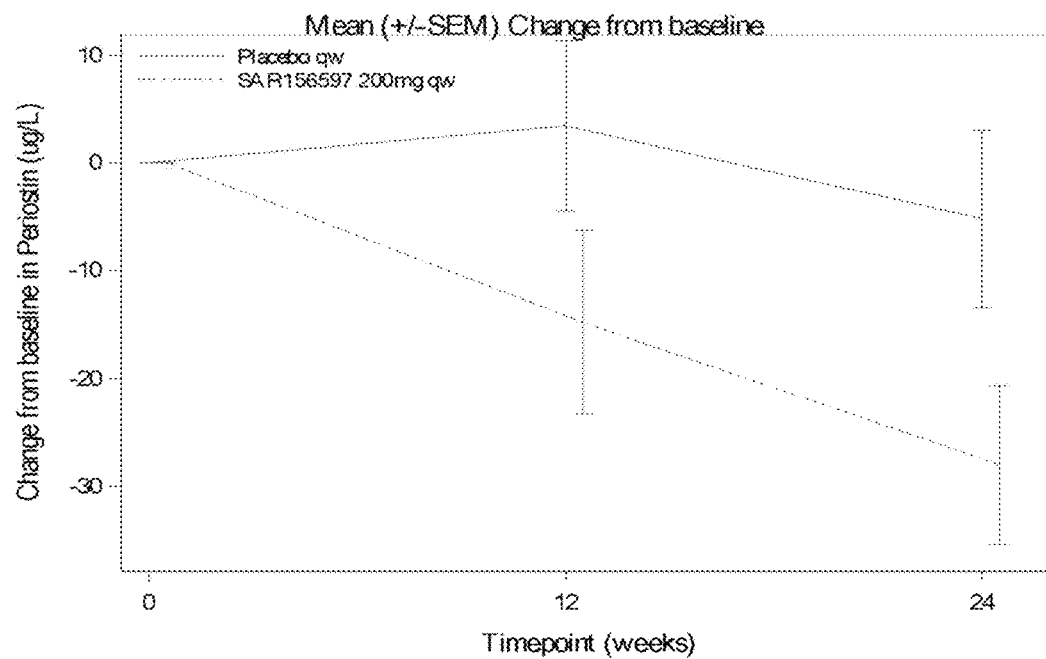

Pharmacokinetic analysis showed that steady state for romilkimab was reached by week 4. The arithmetic mean (SD) $C_{trough}$ was 38.23 (17.96) μg/mL at week 4 and 47.45 (30.23) μg/mL at week 24, respectively. Immunogenicity testing showed that no patients in either treatment group had pre-existing positive ADAs at baseline. Three patients in the romilkimab group and 0 in the placebo group developed positive ADAs by week 24; all were considered low titre. None of the ADA positivity was associated with TEAEs. Romilkimab was associated with a statistically significant reduction in TARC versus placebo; the LS mean difference at week 24 was −115.56 ng/L [95% CI: −216.87, −14.26; p=0.03] (FIG. 8A). Periostin showed a strong trend for greater decline with romilkimab versus placebo; the LS mean difference at week 24 was −16.92 μg/L [−35.19, 1.35; p=0.07] (FIG. 8B). Additional biomarkers were not significantly different between romilkimab and placebo (Table 21).

TABLE 20

Distribution of events reflecting disease progression

| Events reflecting disease progression used in time to progression analysis, n (%) | Placebo QW (n = 49) | Romilkimab 200 mg QW (n = 48) |
|---|---|---|
| Patients with a decrease >10% in % predicted FVC from baseline | 4 (8.2) | 3 (6.3) |
| Patients with a decrease >15% in % predicted $DL_{CO}$ (haemoglobin corrected) from baseline | 3 (6.1) | 3 (6.3) |
| Patients with an increase >20% or >+5 in mRSS from baseline | 5 (10.2) | 3 (6.3) |
| Patients with a CRISS event | 1 (2.0) | 0 |
| Death events | 0 | 0 |
| Patients with a decrease >10% in % predicted FVC and a decrease >15% in % predicted $DL_{CO}$ (haemoglobin corrected) from baseline | 1 (2.0) | 0 |
| Patients with a decrease >10% in % predicted FVC and a decrease >15% in % predicted $DL_{CO}$ (haemoglobin correct) from baseline and a CRISS event | 1 (2.0) | 0 |

CRISS, composite response index in diffuse cutaneous systemic sclerosis; DLco, diffusing lung capacity for carbon monoxide; FVC, forced vital capacity; mRSS, modified Rodnan Skin Score; QW, once-weekly.

TABLE 21

Mean change from baseline to week 24 in protein biomarkers in the ITT population treated with romilkimab versus placebo.

|  | Placebo QW (n = 49) | Romilkimab 200 mg QW (n = 48) |
|---|---|---|
| TARC (ng/L) | | |
| Baseline mean (SD) | 576.07 (330.29) [n = 46] | 583.00 (406.42) [n = 46] |
| LS mean (SE) change from baseline | −20.38 (36.03) [n = 45] | −135.94 (36.04) [n = 45] |
| LS mean difference [95% CI] (p-value) at week 24 | −115.56 [−216.87, −14.26] (0.03) | |
| Periostin (μg/L) | | |
| Baseline mean (SD) | 138.82 (91.81) [n = 45] | 156.22 (96.14) [n = 46] |
| LS mean (SE) change from baseline | −7.39 (6.49) [n = 45] | −24.31 (6.49) [n = 45] |
| LS mean difference [95% CI] (p-value) at week 24 | −16.92 [−35.19, 1.35] (0.07) | |
| Eotaxin-3 (ng/L) | | |
| Baseline mean (SD) | 29.11 (16.60) [n = 45] | 30.44 (24.92) [n = 46] |
| LS mean (SE) change from baseline | −2.05 (10.91) [n = 45] | 12.49 (10.80) [n = 45] |
| LS mean difference [95% CI] (p-value) at week 24 | 14.55 (−16.01, 45.10) (0.35) | |
| COMP (μg/L) | | |
| Baseline mean (SD) | 377.39 (200.09) [n = 46] | 406.31 (230.56) [n = 45] |
| LS mean (SE) change from baseline | −29.59 (15.62) [n = 46] | −24.62 (15.90) [n = 44] |
| LS mean difference [95% CI] (p-value) at week 24 | 4.97 [−39.38, 49.33] (0.82) | |
| CCL2 (ng/L) | | |
| Baseline mean (SD) | 360.27 (160.55) [n = 44] | 394.89 (647.82) [n = 46] |
| LS mean (SE) change from baseline | −15.28 (28.78) [= 44] | 47.13 (28.97) [n = 43] |
| LS mean difference [95% CI] (p-value) at week 24 | 62.40 [−18.81, 143.62] (0.13) | |

CCL2, chemokine (C-C motif) ligand 2; CI, confidence interval; COMP, cartilage oligomeric matrix protein; ITT, intent-to-treat; LS, least-squares; QW, once-weekly; SD, standard deviation; SE, standard error; TARC, thymus and activation regulated chemokine.

Safety

Treatment-Emergent Adverse Events

Infections were the most frequently reported TEAEs with more occurring in the RKB group (54.2%) compared to placebo (46.9%) group. The most common infections were within the upper respiratory tract. More events of oral herpes occurred in the RKB group (10.4%) compared to the placebo group (2.0%).

Skin and Subcutaneous Tissue Disorders were reported with slightly higher frequency in the placebo group (36.7%) compared to RKB group (31.3%). The most commonly reported event was skin ulcer (or digital ulcer) in 30.6% and 16.7% of the patients in the placebo and RKB groups, respectively.

Gastrointestinal Disorders were reported with higher frequency in the RKB group (25.0%) compared to placebo group (14.3%). The most commonly reported event was diarrhea which occurred in 8.2% and 14.6% of the patients in the placebo and SAR156507 groups, respectively.

Musculoskeletal and Connective Tissue Disorders were reported with higher frequency in the RKB group (22.9%) compared to placebo group (14.3%). Respiratory, Thoracic and Mediastinal Disorders were reported with slightly higher frequency in the placebo group (16.3%) compared to RKB group (12.5%). Nervous System Disorders were reported with higher frequency in the RKB group (18.8%) compared to placebo group (6.1%). From these three latter SOCs, some notable imbalances at the PT level include events of headache (2.0% vs. 8.3%), cough (0% vs. 6.3%), and arthralgia (2.0% vs. 8.3%) in the placebo and RKB groups, respectively.

TABLE 22

Overview of adverse event profile: Treatment emergent adverse events during the principal TEAE period by treatment group - Safety population.

| n (%) | Placebo qw (N = 49) | RKB 200 mg qw (N = 48) |
|---|---|---|
| Patients with any TEAE | 41 (83.7) | 40 (83.3) |
| Patients with any treatment emergent SAE | 5 (10.2) | 4 (8.3) |
| Patients with any TEAE leading to death | 0 | 1 (2.1) |
| Patients with any TEAE leading to permanent treatment discontinuation | 1 (2.0) | 2 (4.2) |

TEAE: Treatment emergent adverse event,
SAE: Serious adverse event
n(%) = number and percentages of patients with at least one TEAE

TABLE 23

Number (%) of patient with TEAE(s) that occurred with a PT ≥5% in any treatment group by primary SOC and PT during the TEAE period - Safety population

| PRIMARY SYSTEM ORGAN CLASS<br>Preferred Term n(%) | Placebo qw<br>(N = 49) | RKB 200 mg qw<br>(N= 48) |
|---|---|---|
| Any class | 41 (83.7) | 40 (83.3) |
| INFECTIONS AND INFESTATIONS | 23 (46.9) | 26 (54.2) |
| Nasopharyngitis | 6 (12.2) | 6 (12.5) |
| Oral herpes | 1 (2.0) | 5 (10.4) |
| Upper respiratory tract infection | 2 (4.1) | 5 (10.4) |
| Cystitis | 2 (4.1) | 3 (6.3) |
| Pharyngitis | 0 | 3 (6.3) |
| NERVOUS SYSTEM DISORDERS | 3 (6.1) | 9 (18.8) |
| Headache | 1 (2.0) | 4 (8.3) |
| RESPIRATORY, THORACIC AND MEDIASTINAL DISORDERS | 8 (16.3) | 6 (12.5) |
| Cough | 0 | 3 (6.3) |
| GASTROINTESTINAL DISORDERS | 7 (14.3) | 12 (25.0) |
| Diarrhoea | 4 (8.2) | 7 (14.6) |
| Gastrooesophageal reflux disease | 0 | 3 (6.3) |
| SKIN AND SUBCUTANEOUS TISSUE DISORDERS | 18 (36.7) | 15 (31.3) |
| Skin ulcer | 15 (30.6) | 8 (16.7) |
| Pruritus | 1 (2.0) | 3 (6.3) |
| MUSCULOSKELETAL AND CONNECTIVE TISSUE DISORDERS | 7 (14.3) | 11 (22.9) |
| Arthralgia | 1 (2.0) | 4 (8.3) |

TEAE: Treatment emergent adverse event,
SOC: System organ class,
PT: Preferred term
MedDRA 21.1
n (%) = number and percentage of patients with at least one TEAE
Note:
Table sorted by SOC internationally agreed order and decreasing frequency of PT
Only SOC with at least one PT ≥5% in at least one group are presented.
* Reported term not coded Serious Treatment-Emergent Adverse Events Nine patients (9.2%) experienced at least one TESAE with 5 (10.2%) and 4 (8.3%) patients in the placebo and RKB groups, respectively (Table 24). The most frequently reported TESAEs were under the SOCs of Infection and Infestations disorders and Cardiac Disorders. TESAE related to infections were reported slightly higher in the RKB group (4.2%) compared to placebo group (2.0%). TESAE related to cardiac disorder events were reported higher in the placebo group (4.1%) compared to RKB group (0.0%). There was no difference in the remaining TESAEs per SOC between the two treatment groups.

TABLE 24

Number (%) of patients with treatment emergent SAEs by Primary SOC and PT - Safety population

| PRIMARY SYSTEM ORGAN CLASS<br>Preferred Term n(%) | Placebo qw<br>(N = 49) | RKB 200 mg qw<br>(N = 48) |
|---|---|---|
| Any class | 5 (10.2) | 4 (8.3) |
| INFECTIONS AND INFESTATIONS | 1 (2.0) | 2 (4.2) |
| Pneumonia bacterial | 0 | 1 (2.1) |
| Bronchiolitis | 0 | 1 (2.1) |
| Pneumonia | 0 | 1 (2.1) |
| Pyelonephritis acute | 1 (2.0) | 0 |
| CARDIAC DISORDERS | 2 (4.1) | 0 |
| Cardiac failure | 1 (2.0) | 0 |
| Cardiomyopathy | 1 (2.0) | 0 |
| RESPIRATORY, THORACIC AND MEDIASTINAL DISORDERS | 1 (2.0) | 0 |
| Dyspnoea | 1 (2.0) | 0 |
| GASTROINTESTINAL DISORDERS | 1 (2.0) | 0 |
| Intestinal pseudo-obstruction | 1 (2.0) | 0 |
| HEPATOBILIARY DISORDERS | 0 | 1 (2.1) |
| Cholecystitis acute | 0 | 1 (2.1) |
| RENAL AND URINARY DISORDERS | 0 | 1 (2.1) |
| Scleroderma renal crisis | 0 | 1 (2.1) |
| GENERAL DISORDERS AND ADMINISTRATION SITE CONDITIONS | 0 | 1 (2.1) |
| Chest pain | 0 | 1 (2.1) |
| INVESTIGATIONS | 1 (2.0) | 0 |
| Echocardiogram abnormal | 1 (2.0) | 0 |

TABLE 24-continued

Number (%) of patients with treatment emergent
SAEs by Primary SOC and PT - Safety population

| PRIMARY SYSTEM ORGAN CLASS<br>Preferred Term n(%) | Placebo qw<br>(N = 49) | RKB 200 mg qw<br>(N = 48) |
| --- | --- | --- |

SAE: Serious adverse event,
SOC: System organ class,
PT: Preferred term
MedDRA 21.1
n(%) = number and percentages of patients with at least one treatment emergent SAE
Note:
Table sorted by SOC internationally agreed order and decreasing frequency of PT according to all TEAE summary
* Reported term not coded Treatment Emergent Adverse Events Leading to Death Two patients developed a TEAE that led to death in the study, with one event occurring in each of the two treatment groups (Table 25). For the TEAE that led to death in the RKB group, approximately three months after starting treatment, a 78-year-old female patient with diagnoses of SSc since August 2016 (baseline mRSS of 35) and SSc-ILD since December 2016 shortly before screening (26 Jan. 2017) and numerous other general medical conditions, developed worsening of renal dysfunction which was ultimately diagnosed as scleroderma renal crisis leading to treatment discontinuation (Table 26). Of note, the patient had a baseline medical history of chronic renal insufficiency and the renal function had already been on the decline leading up to randomization (creatinine=94.1 µmol/L in December 2016, screening creatinine=103 µmol/L, and baseline creatinine=122 µmol/L) which was attributed to an age-related process per the guidance of a nephrology consultation. She was diagnosed with acute renal failure at week 6, with creatinine of 172.6 µmol/L, treated with furosemide and prednisolone. Several weeks after IMP discontinuation, the patient was then hospitalized with diagnosis of bilateral pneumonia. This hospitalization was complicated by respiratory failure, hypertension and a rapid progression of renal failure leading to hemodialysis and death.

For the TEAE that led to death in the placebo group, a 31 year-old male patient on background therapy of methotrexate and low dose prednisone prior to randomization into the study, developed a cardiomyopathy (primary SSc cardiomyopathy) that was treated with high dose corticosteroids and led to study treatment discontinuation (Table 27). Ultimately, the patient died due to this event, approximately nine months after study treatment discontinuation.

TABLE 25

Number (%) of patients with TEAE(s) leading to
death by Primary SOC and PT - Safety population

| PRIMARY SYSTEM ORGAN CLASS<br>Preferred Term n(%) | Placebo qw<br>(N = 49) | RKB 200 mg qw<br>(N = 48) |
| --- | --- | --- |
| Any class | 1 (2.0) | 1 (2.1) |
| CARDIAC DISORDERS | 1 (2.0) | 0 |
| Cardiomyopathy | 1 (2.0) | 0 |
| RENAL AND URINARY DISORDERS | 0 | 1 (2.1) |
| Scleroderma renal crisis | 0 | 1 (2.1) |

TEAE:
Treatment emergent adverse event,
SOC: System organ class,
PT: Preferred term
MedDRA 21.1
n(%) = number and percentages of patients with at least one TEAE leading to death
Note:
Table sorted by SOC internationally agreed order and decreasing frequency of PT according to all TEAE summary
* Reported term not coded Adverse Events Leading to Permanent Discontinuation

TABLE 26

Number (%) of patients with TEAE(s) leading to permanent treatment
discontinuation by primary SOC and PT - Safety population

| PRIMARY SYSTEM ORGAN CLASS<br>Preferred Term n(%) | Placebo qw<br>(N = 49) | RKB 200 mg qw<br>(N = 48) |
| --- | --- | --- |
| Any class | 1 (2.0) | 2 (4.2) |
| CARDIAC DISORDERS | 1 (2.0) | 0 |
| Cardiomyopathy | 1 (2.0) | 0 |
| GASTROINTESTINAL DISORDERS | 0 | 1 (2.1) |
| Oesophageal stenosis | 0 | 1 (2.1) |

TABLE 26-continued

Number (%) of patients with TEAE(s) leading to permanent treatment discontinuation by primary SOC and PT - Safety population

| PRIMARY SYSTEM ORGAN CLASS<br>Preferred Term n(%) | Placebo qw<br>(N = 49) | RKB 200 mg qw<br>(N = 48) |
|---|---|---|
| RENAL AND URINARY DISORDERS | 0 | 1 (2.1) |
| Scleroderma renal crisis | 0 | 1 (2.1) |

TEAE: Treatment emergent adverse event,
SOC: System organ class,
PT: Preferred term
MedDRA 21.1
n(%) = number and percentages of patients with at least one TEAE leading to permanent treatment discontinuation
Note:
Table sorted by SOC internationally agreed order and decreasing frequency of PT according to all TEAE summary
\* Reported term not coded Other Significant Adverse Events (Including AESI, Labs)

A total of 2 patients experienced a TEAE considered as an AESI per protocol as seen in Table 27. No difference was seen in the vital signs (Table 28) or ECG characteristics (Table 29) between the two treatment groups. There were no reported cases of vasculitis, tuberculosis or anaphylaxis.

Adverse Events of Special Interest

TABLE 27

Number (%) of patients with at least one AESI - Safety population

| AESI Category<br>Preferred Term n(%) | Placebo qw<br>(N = 49) | RKB 200 mg qw<br>(N = 48) |
|---|---|---|
| Any class | 1 (2.0) | 1 (2.1) |
| Pregnancy$^a$ | 0 | 0 |
| Overdose$^a$ | 0 | 0 |
| Increase in ALT$^b$ | 1 (2.0) | 0 |
| ALT >3 ULN | 1 (2.0) | 0 |
| Confirmed vasculitis$^c$ | 0 | 0 |
| Anaphylactic reactions$^c$ | 0 | 0 |
| Severe Injection Site Reaction$^d$ | 0 | 0 |
| Tuberculosis$^e$ | 0 | 0 |
| Acute renal failure$^f$ | 0 | 1 (2.1) |
| Scleroderma renal crisis | 0 | 1 (2.1) |

MedDRA 21.1;
AESI: Adverse Event of Special Interest,
PT: Preferred term
$^a$AESI category using the e-CRF tick box on the AE.
$^b$Increase in ALT >3 ULN selected using laboratory data.
$^c$AESI definitions were identified using a CMQ coding list.
$^d$AESI definitions were identified by AEHLT = "Injection site reactions" and AESEV = "SEVERE".
$^e$AESI definitions were identified using a CMQ coding list or Initiation of medications for suspected tuberculosis, selected using a WHODD CDG00737 "initiation of medications for suspected tuberculosis" are used.
$^f$Acute renal failure selected using a CMQ coding list or using the e-CRF "Acute renal failure" tick box on the AE page.
n (%) = number and percentage of patients with at least one TEAE Vital Signs and ECG Observations

TABLE 28

Vital signs - Number of patients with abnormalities (PCSA) during the TEAE period - Safety population

| Vital Signs Parameter<br>PCSA criteria n/N1 (%) | Placebo qw<br>(N = 49) | RKB 200 mg qw<br>(N = 48) |
|---|---|---|
| Systolic Blood Pressure | | |
| ≤95 mmHg and decrease from baseline ≥20 mmHg | 1/49 (2.0) | 4/48 (8.3) |
| ≥160 mmHg and increase from baseline ≥20 mmHg | 2/49 (4.1) | 1/48 (2.1) |
| Diastolic Blood Pressure | | |
| ≤45 mmHg and decrease from baseline ≥10 mmHg | 1/49 (2.0) | 0/48 |
| ≥110 mmHg and increase from baseline ≥10 mmHg | 0/49 | 1/48 (2.1) |
| Heart Rate | | |
| ≤50 beats/min and decrease from baseline ≥20 beats/min | 0/49 | 0/48 |
| ≥120 beats/min and increase from baseline ≥20 beats/min | 0/49 | 0/48 |
| Weight | | |
| ≥5% decrease from baseline | 10/49 (20.4) | 5/48 (10.4) |
| ≥5% increase from baseline | 10/49 (20.4) | 6/48 (12.5) |

PCSA: Potentially clinically significant abnormalities (Version of 2014-05-24 v1.0)
Note:
The number (n) represents the subset of the total number of patients who met the criterion at least once during the TEAE period.
The denominator (/N1) for each parameter within a treatment group is the number of patients who had that parameter assessed post-baseline (not missing) during the TEAE period.
For PCSA including condition based only on change from baseline, the denominator is restricted on patients having (not missing) a baseline and a post-baseline values during the TEAE period.

TABLE 29

ECG - Number of patients with abnormalities (PCSA) during the TEAE period - safety population

| ECG parameter PCSA criteria n/N1 (%) | Placebo qw (N = 49) | RKB 200 mg qw (N = 48) |
|---|---|---|
| Heart Rate | | |
| <50 beats/min | 1/48 (2.1) | 1/48 (2.1) |
| <50 beats/min and decrease from baseline ≥20 beats/min | 0/48 | 0/48 |
| <40 beats/min | 0/48 | 0/48 |
| <40 beats/min and decrease from baseline ≥20 beats/min | 0/48 | 0/48 |
| <30 beats/min | 0/48 | 0/48 |
| <30 beats/min and decrease from baseline ≥20 beats/min | 0/48 | 0/48 |
| >90 beats/min | 10/48 (20.8) | 6/48 (12.5) |
| >90 beats/min and increase from baseline ≥20 beats/min | 2/48 (4.2) | 3/48 (6.3) |
| >100 beats/min | 2/48 (4.2) | 3/48 (6.3) |
| >100 beats/min and increase from baseline ≥20 beats/min | 1/48 (2.1) | 3/48 (6.3) |
| >120 beats/min | 1/48 (2.1) | 0/48 |
| >120 beats/min and increase from baseline ≥20 beats/min | 1/48 (2.1) | 0/48 |
| PR Interval | | |
| >200 msec | 2/48 (4.2) | 4/48 (8.3) |
| >200 msec and increase from baseline ≥25% | 0/48 | 1/48 (2.1) |
| >220 msec | 1/48 (2.1) | 1/48 (2.1) |
| >220 msec and increase from baseline ≥25% | 0/48 | 0/48 |
| >240 msec | 0/48 | 0/48 |
| >240 msec and increase from baseline ≥25% | 0/48 | 0/48 |
| QRS Interval | | |
| >110 msec | 4/48 (8.3) | 5/48 (10.4) |
| >110 msec and increase from baseline ≥25% | 0/48 | 1/48 (2.1) |
| >120 msec | 1/48 (2.1) | 3/48 (6.3) |
| >120 msec and increase from baseline ≥25% | 0/48 | 1/48 (2.1) |
| QT Interval | | |
| > 500 msec | 0/48 | 0/48 |
| QTc Bazett | | |
| >450 msec | 15/48 (31.3) | 11/48 (22.9) |
| >480 msec | 3/48 (6.3) | 4/48 (8.3) |
| >500 msec | 2/48 (4.2) | 1/48 (2.1) |
| QTc Bazett - Change from baseline[a] | | |
| Increase from baseline >30 and ≤60 msec | 9/48 (18.8) | 4/46 (8.7) |
| Increase from baseline >60 msec | 3/48 (6.3) | 1/46 (2.2) |
| QTc Fridericia | | |
| >450 msec | 6/48 (12.5) | 5/48 (10.4) |
| >480 msec | 1/48 (2.1) | 2/48 (4.2) |
| >500 msec | 1/48 (2.1) | 0/48 |
| QTc Fridericia - Change from baseline[a] | | |
| Increase from baseline >30 and ≤60 msec | 9/48 (18.8) | 2/46 (4.3) |
| Increase from baseline >60 msec | 3/48 (6.3) | 1/46 (2.2) |

PCSA: Potentially clinically significant abnormalities (Version of 2014-05-24 v1.0)

Note:

The number (n) represents the subset of the total number of patients who met the criterion at least once during the TEAE period.

The denominator (/N1) for each parameter within a treatment group is the number of patients who had that parameter assessed post-baseline (not missing) during the TEAE period.

For PCSA including condition based only on change from baseline, the denominator is restricted on patients having (not missing) a baseline and a post-baseline values during the TEAE period.

[a] A patient who experienced one PCSA in several categories is counted only in the worst category

SUMMARY

Primary efficacy endpoint as measured by absolute change in mRSS from baseline at Week 24 showed a statistically significant difference between RKB and placebo: Absolute change in mRSS from baseline at Week 24 was −2.45 (0.85) and −4.76 (0.86) for the placebo and RKB groups, respectively, yielding a decrease of 2.31 (1.21) with an associated one-sided p-value=0.0291.

Secondary efficacy endpoints as measured by HAQ-DI did not show a difference between RKB and placebo. The secondary efficacy endpoints of FVC and DLco also did not show a difference between the two groups but the RKB group had less of a decline in 24 weeks for both parameters compared to the placebo group.

Mean change in absolute FVC (L) from baseline at week 24 was −0.08 (0.04) and −0.01 (0.04) for the placebo and RKB groups, respectively, yielding a difference of −0.07 (0.06) with an associated one-side p-value=0.0964.

Mean change in absolute DLco (mmol/min/kPa) from baseline at Week 24 was −0.27 (0.10) and −0.12 (0.10) for the placebo and RKB groups, respectively, yielding a difference of −0.15 (0.14) with an associated one-side p-value=0.1352.

There was a similar incidence of Treatment Emergent Adverse Effects (TEAEs), Treatment Emergent Serious Adverse Effects (TESAEs), TEAEs leading to death and TEAEs leading to treatment discontinuation between the two treatment groups; more TEAEs occurred within the System Organ Class (SOC) of Infection and Infestations and Gastrointestinal Disorders for the RKB group while more TEAEs occurred within the SOC of Skin and Subcutaneous Tissue Disorders for the placebo group.

What is claimed is:

1. A method for treating systemic sclerosis (SSc) in a human subject with SSc, the methods comprising administering about 200 mg of a dual-V-region bispecific antibody or antigen-binding fragment that specifically binds IL-4 and IL-13 subcutaneously to the subject, wherein a portion of human subjects treated have an improved modified Rodnan Skin Score (mRSS) of at least 20% at 24 weeks after initial administration of the bispecific antibody or antigen-binding fragment compared to baseline.

2. The method of claim 1, wherein 200 mg of the bispecific antibody is administered to the subject about once per week or about every 5 to 9 days.

3. The method of claim 1, wherein the treatment is given for at least about 24 weeks.

4. The method of claim 1, wherein the bispecific antibody is in a pharmaceutical formulation.

5. The method of claim 4, wherein the pharmaceutical formulation comprises about 100 mg/ml bispecific antibody, about 6.3 mM monobasic sodium phosphate, about 37 mM Tris, about 5% (w/v) sucrose, about 3% (w/v) proline, and about 0.2% (w/v) polysorbate 80, wherein the pH of the formulation is about 7.0.

6. The method of claim 5, wherein the formulation is reconstituted from a lyophilized formulation.

7. The method of claim 1, wherein the bispecific antibody is administered in combination with another agent.

8. The method of claim 7, wherein the another agent is administered before, simultaneously with, or after administration of the bispecific antibody.

9. The method of claim 1, wherein the systemic sclerosis is diffuse cutaneous systemic sclerosis.

10. The method of claim 1, wherein the bispecific antibody or bispecific antibody fragment thereof comprises a light chain polypeptide comprising a light chain variable domain $VL_{hB-B13}$ and a light chain variable domain $VL_{hBD4-8}$, and a heavy chain polypeptide comprising a heavy chain variable domain $VH_{hB-B13}$ and a heavy chain variable domain $VH_{hBD4-8}$, wherein:

$VL_{hB-B13}$ comprises the three CDRs comprising the amino acid sequences

```
                                        (SEQ ID NO: 8)
            RASESVDSYGQSYMH, (SEQ ID NO: 9)
            LASNLES,
            and (SEQ ID NO: 10)
            QQNAEDSRT;
```

$VL_{hBD4-8}$ comprises the three CDRs comprising the amino acid sequences

```
                                        (SEQ ID NO: 14)
            HASQNIDVWLS, (SEQ ID NO: 15)
            KASNLHTG,
            and (SEQ ID NO: 16)
            QQAHSYPFT,
```

$VH_{hB-B13}$ comprises the three CDRs comprising the amino acid sequences

```
                                        (SEQ ID NO: 11)
            GFSLTDSSIN, (SEQ ID NO: 12)
            DGRID,
            and (SEQ ID NO: 13)
            DGYFPYAMDF,
```

$VH_{hBD4-8}$ comprises the three CDRs comprising the amino acid sequences

```
                                        (SEQ ID NO: 17)
            GYSFTSYWIH, (SEQ ID NO: 18)
            IDPSDGETR
```

-continued and

LKEYGNYDSFYFDV. (SEQ ID NO: 19)

11. The method of claim 10, wherein:
VL$_{hB-B13}$ comprises an amino acid sequence at least 95% identical to the amino acid sequence of SEQ ID NO:1,
VL$_{hBD4-8}$ comprises an amino acid sequence at least 95% identical to the amino acid sequence of SEQ ID NO:3,
VH$_{hB-B13}$ comprises an amino acid sequence at least 95% identical to the amino acid sequence of SEQ ID NO:2, and
VH$_{hBD4-8}$ comprises an amino acid sequence at least 95% identical to the amino acid sequence of SEQ ID NO:4.

12. The method of claim 10, wherein:
VL$_{hB-B13}$ comprises the amino acid sequence of SEQ ID NO:1,
VL$_{hBD4-8}$ comprises the amino acid sequence of SEQ ID NO:3,
VH$_{hB-B13}$ comprises the amino acid sequence of SEQ ID NO:2, and
VH$_{hBD4-8}$ comprises the amino acid sequence of SEQ ID NO:4.

13. The method of claim 10, wherein the light chain polypeptide comprises the structure N-VL$_{hB-B13}$-linker-VL$_{hBD4-8}$-CL-C and the heavy chain polypeptide comprises the structure N-VH$_{hB-B13}$-linker-V$_{hBD4-8}$-CH1-C.

14. The method of claim 10, wherein the light chains comprise the structure N-VL$_{hB-B13}$-linker-VL$_{hBD4-8}$-CL-C and the heavy chains comprise the structure N-VH$_{hB-B13}$-linker-VH$_{hBD4-8}$-CH1-CH2-CH3-C.

15. The method of claim 14, wherein the linker comprises the amino acid sequence of SEQ ID NO:6.

16. The method of claim 10, wherein the bispecific antibody or bispecific antibody fragment thereof comprises two identical light chain polypeptides and two identical heavy chain polypeptides.

17. The method of claim 10, wherein the light chain polypeptide comprises an amino acid sequence having at least about 90% identity to the amino acid sequence of SEQ ID NO:22 and the heavy chain polypeptide comprises an amino acid sequence having at least about 90% identity to the amino acid sequence of SEQ ID NO:23.

18. The method of claim 10, wherein the light chain polypeptide comprises the amino acid sequence of SEQ ID NO:22 and the heavy chain polypeptide comprises the amino acid sequence of SEQ ID NO:23.

19. A method of reducing sclerotic plaques in a human subject with SSc, the method comprising administering an effective amount of an anti-IL4/anti-IL13 bispecific antibody to said subject; wherein a portion of human subjects treated have an improved modified Rodnan Skin Score (mRSS) of at least 20% at 24 weeks after initial administration of the bispecific antibody or antigen-binding fragment compared to baseline wherein the sclerotic plaques are reduced by at least about 20%, 40%, 60%, 80% or 100% at about 24 weeks after initial administration of the bispecific antibody compared to baseline.

\* \* \* \* \*

UNITED STATES PATENT AND TRADEMARK OFFICE
CERTIFICATE OF CORRECTION

PATENT NO. : 11,827,671 B2
APPLICATION NO. : 16/881863
DATED : November 28, 2023
INVENTOR(S) : Christina Soubrane et al.

It is certified that error appears in the above-identified patent and that said Letters Patent is hereby corrected as shown below:

In the Claims

In Claim 10, Column 89, Line 64: please replace "$VL_{hB-B13}$" with --$VL_{hB-B13}$--;

In Claim 10, Column 89, Line 65: please replace "$VL_{hBD4-8}$" with --$VL_{hBD4-8}$--;

In Claim 10, Column 89, Line 66: please replace "$VH_{hB-B13}$" with --$VH_{hB-B13}$--;

In Claim 10, Column 89, Line 67: please replace "$VH_{hBD4-8}$" with --$VH_{hBD4-8}$--;

In Claim 10, Column 90, Line 24: please replace "$VL_{hB-B13}$" with --$VL_{hB-B13}$--;

In Claim 10, Column 90, Line 36: please replace "$VL_{hBD4-8}$" with --$VL_{hBD4-8}$--;

In Claim 10, Column 90, Line 47: please replace "$VH_{hB-B13}$" with --$VH_{hB-B13}$--;

In Claim 10, Column 90, Line 48: please replace "amino acid sequences" with --amino acid sequences and--;

In Claim 10, Column 90, Line 60: please replace "$VH_{hBD4-8}$" with --$VH_{hBD4-8}$--;

In Claim 11, Column 91, Line 7: please replace "$VL_{hB-B13}$" with --$VL_{hB-B13}$--;

In Claim 11, Column 91, Line 9: please replace "$VL_{hBD4-8}$" with --$VL_{hBD4-8}$--;

In Claim 11, Column 91, Line 11: please replace "$VH_{hB-B13}$" with --$VH_{hB-B13}$--;

In Claim 11, Column 91, Line 14: please replace "$VH_{hBD4-8}$" with --$VH_{hBD4-8}$--;

Signed and Sealed this
Twenty-first Day of May, 2024

*Katherine Kelly Vidal*
Katherine Kelly Vidal
*Director of the United States Patent and Trademark Office*

CERTIFICATE OF CORRECTION (continued)
U.S. Pat. No. 11,827,671 B2

In Claim 12, Column 91, Line 17: please replace "VL$_{hB\text{-}B13}$" with --VL$_{hB\text{-}B13}$--;

In Claim 12, Column 91, Line 19: please replace "VL$_{hBD4\text{-}8}$" with --VL$_{hBD4\text{-}8}$--;

In Claim 12, Column 91, Line 21: please replace "VH$_{hB\text{-}B13}$" with --VH$_{hB\text{-}B13}$--;

In Claim 12, Column 91, Line 23: please replace "VH$_{hBD4\text{-}8}$" with --VH$_{hBD4\text{-}8}$--;

In Claim 13, Column 91, Lines 26-27: please replace "N-VL$_{hB\text{-}B13}$-linker-VL$_{hBD4\text{-}8}$-CL-C" with --N-VL$_{hB\text{-}B13}$-linker-VL$_{hBD4\text{-}8}$-CL-C--;

In Claim 13, Column 91, Line 28: please replace "N-VH$_{hB\text{-}B13}$-linker-VH$_{hBD4\text{-}8}$-CH1-C" with --N-VH$_{hB\text{-}B13}$-linker-VH$_{hBD4\text{-}8}$-CH1-C--;

In Claim 14, Column 91, Line 30: please replace "N-VL$_{hB\text{-}B13}$-linker-VL$_{hBD4\text{-}8}$-CL-C" with --N-VL$_{hB\text{-}B13}$-linker-VL$_{hBD4\text{-}8}$-CL-C--; and In Claim 14, Column 92, Lines 1-2: please replace "N-VH$_{hB\text{-}B13}$-linker-VH$_{hBD4\text{-}8}$-CH1-CH2-CH3-C" with --N-VH$_{hB\text{-}B13}$-linker-VH$_{hBD4\text{-}8}$-CH1-CH2-CH3-C--.